US009845361B2

(12) United States Patent
Goletz et al.

(10) Patent No.: US 9,845,361 B2
(45) Date of Patent: Dec. 19, 2017

(54) RECOGNITION MOLECULES FOR THE TREATMENT AND DETECTION OF TUMORS

(71) Applicant: Glycotope GmbH, Berlin (DE)

(72) Inventors: Steffen Goletz, Glienicke-Nordbahn (DE); Antje Danielczyk, Kolberg (DE); Renate Stahn, Berlin (DE); Uwe Karsten, Panketal (DE)

(73) Assignee: GLYCOTOPE GmbH, Berlin (DE)

( * ) Notice: Subject to any disclaimer, the term of this patent is extended or adjusted under 35 U.S.C. 154(b) by 72 days.

(21) Appl. No.: 14/316,389

(22) Filed: Jun. 26, 2014

(65) Prior Publication Data

US 2015/0005474 A1 Jan. 1, 2015

Related U.S. Application Data

(63) Continuation of application No. 10/540,479, filed as application No. PCT/DE2004/000132 on Jan. 23, 2004, now Pat. No. 8,779,102.

(30) Foreign Application Priority Data

Jan. 23, 2003 (DE) .................................. 103 03 664

(51) Int. Cl.
| | | |
|---|---|---|
| C07K 16/00 | (2006.01) | |
| C07K 16/30 | (2006.01) | |
| A61K 51/08 | (2006.01) | |
| A61K 39/00 | (2006.01) | |

(52) U.S. Cl.
CPC .......... *C07K 16/3092* (2013.01); *A61K 51/08* (2013.01); *A61K 51/088* (2013.01); *A61K 2039/505* (2013.01); *C07K 2317/24* (2013.01); *C07K 2317/34* (2013.01); *C07K 2317/56* (2013.01); *C07K 2317/565* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,506,343 A | 4/1996 | Kufe | |
| 5,683,674 A | 11/1997 | Taylor-Papadimitriou et al. | |
| 5,739,277 A | 4/1998 | Presta et al. | |
| 5,804,187 A | 9/1998 | do Couto | |
| 6,315,997 B1 | 11/2001 | do Couto et al. | |
| 2002/0132771 A1 | 9/2002 | Madiyalakan | |
| 2006/0292643 A1* | 12/2006 | Goletz ................... | A61K 51/08 435/7.23 |

FOREIGN PATENT DOCUMENTS

| | | |
|---|---|---|
| DE | 4329004 A1 | 3/1995 |
| WO | 93/20841 A1 | 10/1993 |
| WO | 01/12217 A1 | 2/2001 |
| WO | WO 0175110 A2 * | 10/2001 ....... A61K 47/48538 |
| WO | 02/44217 A2 | 6/2002 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
Ko et al (PLOS ONE, 20(7):e0134600, p. 1-16, 2015).*
Jackson et al (JI, 154:3310-3319, 1995).*
Abstract of Euhus, et al., "Appraisal of Anti-Idiotypic Antibodies in the Treatment of Solid Tumors in Humans", *Surgery, Gynecology and Obstetrics*, 1992, vol. 175(1), pp. 89-96.
Abstract of Linardou et al., "Deoxyribonuclease I (DNAse I). A Novel Approach for Targeted Cancer Therapy," *Cell Biophys.* 24-25:243-248, 1994.
Bagshawe et al., "Antibody-Directed Enzyme Prodrug Therapy (ADEPT) for Cancer," *Expert Opin. Biol. Ther.* 4:1777-1789, 2004.
Boel et al., "Functional human monoclonal antibodies of all isotypes constructed from phage display library-derived single-chain Fv antibody fragments," *Journal of Immunological Methods* 239:153-166, 2000.
Brechbiel et al., "Synthesis on 1-(p-Isothiocyanatobenzyl) derivatives of DTPA and EDTA: Antibody labelling and tumor-imaging studies," *Inorg. Chem.* 25:2772-2781, 1986.
Burgess et al., "Possible dissociation of the heparin-binding and mitogenic activities of the heparin-binding (acidic fibroblast) growth factor-1 from its receptor binding activities by site directed mutagenesis of a single lysine residue," *Journal of Cell Biology* 111:2129-2138, 1990.
Casset et al., "A peptide mimetic of an anti-CD4 monoclonal antibody by rational design," *Biochemical and Biophysical Research Communications* 307:198-205, 2003.
Chen et al., "Selection and analysis of an optimized anti-VEGF antibody: crystal structure of an affinity-matured Fab in complex with antigen," *Journal of Molecular Biology* 293:865-881, 1999.
Chothia et al., "Canonical structures for the hypervariable regions of immunoglobulins," *Journal of Molecular Biology* 196:901-917, 1987.
Chothia et al., "Conformations of immunoglobulin hypervariable regions," *Nature* 342:877-883, Dec. 1989.
Chothia et al., "Structural repertoire of the human VH segments," *Journal of Molecular Biology* 227:799-817, 1992.
Chothia et al., "The predicated structure of immunoglobulin D1.3 and its comparison with the crystal structure," *Science Reports* 233:755-758, Aug. 15, 1986.
Dai et al., "Effect of desialylation on binding, affinity, and specificity of 56 monoclonal antibodies against MUC1 mucin," *Tumor Biology* 19(S1):100-110, 1998.
De Pascalis et al., "Grafting of "abbreviated" complementarity-determining regions containing specificity-determining residues essential for ligand contact to engineer a less immunogenic humanized monoclonal antibody," *Journal of Immunology* 169:3076-3084, 2002.

(Continued)

*Primary Examiner* — Brad Duffy
(74) *Attorney, Agent, or Firm* — Seed IP Law Group LLP

(57) ABSTRACT

The invention relates to recognition molecules directed towards tumors, and it also relates to pharmaceutical compositions comprising said recognition molecules, methods for the production of said recognition molecules, and to the use of said recognition molecules in the diagnosis and therapy of tumor diseases.

7 Claims, 21 Drawing Sheets

(56) References Cited

OTHER PUBLICATIONS

Dermer, "Another anniversary for the war on cancer," *Bio/technology* 12, 1994, p. 320.
Dixon, "Evaluation of the CASP2 docking section," *Proteins* 1997; Suppl 1: 198-204.
F. Schneider, et al., "Overexpression of Sialyltransferase CMP-Sialic Acid: Galbetal, 3Galnac-R Alpha6-Sialyltransferase is Related to Poor Patient Survival in Human Colorectal Carcinomas", *Cancer Research, American Association of Cancer Research*, Baltimore, MD, US, vol. 61, No. 11, Jun. 1, 2001, pp. 4605-4611, XP002232470.
Fiebig et al., "Clonogenic assay with established human tumor xenografts: correlation of in vitro to in vivo activity as a basis for anticancer drug discovery," *European Journal of Cancer* 40:802-820, 2004.
Freshney, *Cultures of Animal Cells, A Manual of Basic Technique*, New York, Alan R. Liss Inc., 1983, p. 4.
Goletz et al., "Binding Patterns of 33 TD-4(MUC1) Antibodies Towards Single-Chain Fragments and Peptides Mimicking the Conformation of the MUC1 PDTRP Epitope," *Tumor Biology* 21(S1), Sep. 2000, p. 142, XP008034905.
Green, et al., "Activation-Induced Cell Death in T Cells", *Immunological Reviews*, 2003, vol. 193, pp. 70-81.
Gura, "Systems for identifying new drugs are often faulty," *Science* 278:1041-1042, 1997.
Gussow et al. "Humanisation of monoclonal antibodies," *Methods in Enzymology*. 1991; 203: 99-121.
Herrera et al., "Efficiency of erthropoietin's signal peptide for HIVmn-1 gp 120 expression," *Biochemical and Biophysical Research Communications* 273:557-559, 2000.
Hinoda et al., "Circulating tumor-associated antigens detected by monoclonal antibodies against the polypeptide core of mucin: comparison of antigen MUSE11 with CA15-3," *Gastroenterologia Japonica* 27(3):390-395, 1992.
Holm et al., "Functional mapping and single chain construction of the anti-cytokeratin 8 monoclonal antibody TS1," *Molecular Immunology* 44:1075-1084, 2007.
Hosse et al., "A new generation of protein display scaffolds for molecular recognition," *Protein Science* 15:14-27, 2006.
Hsieh et al., "Controlling Chemical Reactivity with Antibodies," *Science* 260:337-339, 1993.
Hu et al., "Humanization of a murine monoclonal antibody by simultaneous optimization of framework and CDR residues," *Journal of Molecular Biology* 294:151-162, 1999.
Hufton et al., "Development and application of cytotoxic T lymphocyte-associated antigen 4 as a protein scaffold for the generation of novel binding ligands," *FEBS Letters* 475(3):225-231, 2000.
Jensen et al., "Functional improvement of antibody fragments using a novel phage coat protein III fusion system," *Biochemical and Biophysical Research Communications* 298:566-573, 2002.
Karsten et al., "A New Monolonal Antibody (A78-G/A7) to the Tomsen-Friedenreich Pan-Tumor Antigen," *Hybridoma* 14(1):37-44, 1995, XP009034408.
Kozak et al., "Nature of the Bifunctional chelating agent used for radioimmunotherapy with Yttrium-90 monoclonal antibodies: Critical factors in determining 'in vivo' survival and organ toxicity," *Cancer Research* 49:2639-2644, May 15, 1989.
Lazar et al., "Transforming growth factor alpha: mutation of aspartic acid 47 and leucine 48 results in different biological activities," *Molecular and Cellular Biology* 8:1247-1252, 1988.
Lensink et al., "Docking and scoring protein complexes: CAPRI 3rd Edition," *Proteins* 2007; 69:704-718.
Liao et al., "Design of transgenes for efficient expression of active chimeric proteins on mammalian cells," *Biotechnol. Bioeng.* 73:313-323, 2000.
Libyh, et al., "A Recombinant Human scFv Anti-RH(D) Antibody with Multiple Valences Using a CTerminal Fragment of C4-Binding Protein", *Blood*, 90(10), pp. 3978-3983, 1997.

MacCallum et al., "Antibody-antigen interactions: contact analysis and binding site topography," *Journal of Molecular Biology* 262:732-745, 1996.
Mariuzza et al., "The structural basis of antigen-antibody recognition," *Annu. Rev. Biophys. Biophys. Chem.* 1987; 16:139-159.
Martin et al., "Structural families in loops of homologous proteins: Automatic classification modeling and application to antibodies," *Journal of Molecular Biology* 263:800-815, 1996.
Matzinger, "Tolerance, Danger, and the Extended Family," *Annual Review in Immunology* 12:991-1045, 1994.
Morrison et al., "Complement Activation and Fc Receptor Binding by IgG," *Protein Engineering of Antibody Molecules for Prophylactic and Therapeutic Applications in Man*, Mike Clark, Ed., pp. 101-113, 1993.
MSNBC News Services, "Mixed results on new cancer drug," Nov. 9, 2000.
Nicaise et al., "Affinity transfer by CDR grafting on a nonimmunoglobulin scaffold," *Protein Science* 13:1882-1891, 2004.
Nuttall et al., "Design and expression of soluble CTLA-4 variable domain as a scaffold for the display of functional polypeptides," *Proteins: Structure, Function, and Genetics* 36:217-227, 1999.
Nygren et al., "Scaffolds for engineering novel binding sites in proteins," *Curr. Opin. Struct. Biol.* 7:463-469, 1997.
Panka et al., "Variable Region Framework Differences result in Decreased or Increased Affinity of Variant Anti-Digoxin Antibodies," *Proc. Natl. Acad. Sci. USA* 85:3080-3084, May 1988.
Peach et al., "Complementarity determining region 1 (CDR1)- and CDR3-analogous regions in CTLA-4 and CD28 determine the binding to B7-1," *Journal of Experimental Medicine* 180:2049-2058, 1994.
Price et al., "Summary Report on the ISOBM TD-4 Workshop: Analysis of 56 Monoclonal Antibodies Against the MUC1 Mucin," *Tumor Biology* 19(1):1-20, Dec. 1998, XP002112482.
Rooman et al., "Amino acid sequence templates derived from recurrent turn motifs in proteins: critical evaluation of their predictive power," *Protein Engineering* 3(1):23-27, 1989.
Rudikoff et al., "Single amino acid substitution altering antigen-binding specificity," *Proceedings of the National Academy of Sciences* 79:1979-1983, 1996.
Saerens et al., "Identification of a Universal VHH Framework to Graft Non-canonical Antigen-binding Loops of Camel Single-domain Antibodies," *Journal of Molecular Biology* 352(3):597-607, Sep. 23, 2005.
Scheibel et al., "Contribution of N- and C-terminal domains to the function of Hsp90 in *Saccharomyces cerevisiae*," *Molecular Microbiology* 34:701-713, 1999.
Schlom, "Monoclonal Antibodies: They're More and Less Than You Think," *Molecular Foundations of Oncology*, 1991, Samuel Broder, Ed., pp. 95-134.
Schneider et al., "Thermostability of Membrane Protein Helix-Helix Interaction Elucidated by Statistical Analysis," *FEBS Lett.* 532:231-236, 2002.
Skerra et al., "Alternative non-antibody scaffolds for molecular recognition," *Current Opinion in Biotechnology* 18:295-303, 2007.
Skerra, "Engineered protein scaffolds for molecular recognition," *Journal of Molecular Recognition* 13:167-187, 2000.
Stimmel et al., "Yttrium-90 chelation properties of tetraazatetraacetic acid macrocyles, diethylenetriaminepentaacetic acid analogues, and a novel terpyridine acyclic chelator," *Bioconjugate Chemistry* 6:219-225, 1995.
Tame, "Scoring functions: a view from the bench," *J. Comput. Aided Mol. Des.* Mar. 1999; 13(2):99-108.
Tonye et al., "A recombinant human scFv anti-Rh(D) antibody with multiple valences using a C-terminal fragment of C4-binding protein," *Blood* 90(10):3978-3983, Nov. 15, 1997.
U. Jeschke, et al., "Expression of the Thomsen-Friedenreich Antigen and of its Putative Carrier Protein Mucin 1 in the Human Placenta and in Trophoblast Cells in Vitro", *Histochemistry and Cell Biology*, vol. 117, No. 3, Mar. 2002, pp. 219-226, XP002290192.
Vajdos et al., "Comprehensive functional maps of the antigen-binding site of an anti-ErbB2 antibody obtained with shotgun scanning mutagenesis," *Journal of Molecular Biology* 320:415-428, 2002.

(56) References Cited

OTHER PUBLICATIONS

Wu et al., "Conformation of complementarity determinging region L1 loop in murine IgG λ light chain extends the repertoire of canonical forms," *Journal of Molecular Biology* 229:597-601, 1993.

Wu, et al., "Conformation of Complementarity Determining Region L1 Loop in Murine IgG A Light Chain Extends the Repertoire of Canonical Forms," *J. Mol. Biol.*, vol. 229, pp. 597-601, 1993.

\* cited by examiner

RECOGNITION MOLECULES FOR THE TREATMENT AND DETECTION OF TUMORS

CROSS REFERENCE TO RELATED APPLICATIONS

This application is a continuation of U.S. patent application Ser. No. 10/540,479 filed May 10, 2006, now issued on Jul. 15, 2014 as U.S. Pat. No. 8,779,102, which is a U.S. national stage application filed under 35 U.S.C. §371 of International Patent Application PCT/DE2004/000132 accorded an international filing date of Jan. 23, 2004, which claims the benefit of German (DE) Application No. 10303664.4 filed Jan. 23, 2003.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 400086_403C1_SEQUENCE_LISTING.txt. The text file is 96.5 KB, was created on Jun. 22, 2014, and is being submitted electronically via EFS-Web.

TECHNICAL FIELD

The invention relates to recognition molecules directed towards tumors, and it also relates to pharmaceutical compositions comprising said recognition molecules, methods for the production of said recognition molecules, and to the use of said recognition molecules in the diagnosis and therapy of tumor diseases.

DETAILED DESCRIPTION

Tumor diseases belong to the most frequent diseases of organisms, especially of mammals such as humans. In particular, successful treatment of a tumor disease depends on the stage of tumor development where therapy is begun. It is advantageous when therapy can be begun at a point in time where the tumor has minimum expansion and diffusion within the body, with expansion being understood to be the individual size of a tumor tissue, and diffusion being understood to be possible metastasization or infiltration into surrounding organs. An organism suffering from a tumor disease secretes particular, quite complex substances or fairly simple molecules which can be utilized in the diagnosis of tumors at an early stage of the disease, i.e., of tumors fairly small in size. The best-known amongst these structures are tumor markers. In general, tumor markers are chemical substances being more or less specific for a particular type of tumor or showing increased presence in association with a tumor. For example, tumor markers can be cellular in nature, such as oncogenes, certain hormone receptors or membrane antigens such as CA 2, CA 3, CA 19-19 and others. However, tumor markers can also be humoral markers being either produced by a tumor or induced by a tumor. More specifically, the group of tumor-produced tumor markers includes tumor-associated antigens, hormones, enzymes and other compounds. For example, tumor-induced humoral tumor markers are enzymes such as alkaline phosphatase or e.g. the acute phase protein (e.g. ferritin). In the prior art, tumor markers are preferably detected using immunologic methods, which is why the synonym "tumor antigen" is frequently used to denote tumor markers. Well-known tumor antigens are oncofetal antigens, blood type-associated antigens, organ-specific antigens and other antigens, such as CA 15-3, for example.

Cancer diagnostics using tumor markers involves several disadvantages. Thus, certain tumor markers may also be present in non-cancerogenic diseases, so that the recognition molecules employed indicate a positive reaction. Furthermore, non-interaction of recognition molecules does not indicate the absence of a tumor disease. Another drawback is that well-known recognition molecules are normally non-specific. That is, positive detection rarely indicates a specific type of tumor disease. In addition, another and crucial drawback of well-known recognition molecules is their limited usability in monitoring the development of tumors, e.g. subsequent to surgery. As a rule, the use of well-known tumor markers therefore is not possible in early recognition or in aftercare, especially in prophylaxis.

In addition to the above general disadvantages, there are some specific drawbacks in recognition molecules directed towards tumor antigens differing only in their glycosylation from a corresponding antigen in normal tissue. The antibodies are required to be glycosylation-dependent and must reflect the change in the state of glycosylation of the antigen in a tumor. Thus, for example, the glycosylation of MUC1 on breast tumor cells is changed. There is massive reduction in the chain length of O-glycans and a reduction of sialic acid O-acetylation.

Another disadvantage of well-known recognition molecules towards tumor markers is that they do not make the tumor recognizable until it has already reached a critical size. That is to say, early stages of tumor growth cannot be determined with well-known recognition molecules directed towards tumor markers.

The polymorphic epithelial mucin MUC1, in the form of the overall molecule, is a well-established tumor marker. As a result of the complexity of the molecule, which is very large, highly glycosylated, essentially consists of a large number of polymorphic tandem repeats of 20 amino acid residues in the extracellular state, and has heterogeneous glycosylation with respect to the tandem repeats, MUC1 has a variety of epitopes. One existing disadvantage is the fact that it is not known which epitope on MUC1 has optimum suitability as a target structure for tumor therapy and diagnosis. Another drawback is that conventional MUC1-specific antibodies (providing relatively good recognition of MUC1 on particular tumors) also give high levels of recognition of such MUC1 released into the serum by tumor cells (shedding). Obviously, such high levels of binding of MUC1 present in the serum in tumor patients is disadvantageous in the therapy of tumor diseases using such MUC1 specific antibodies. Another drawback is that most of the MUC1-specific antibodies exhibit binding to several normal tissues as well.

The object of the invention is therefore to provide recognition molecules which, on the one hand, allow easy, reliable and efficient detection of tumors and, in addition, can be used in the prophylaxis, therapy and/or aftercare of tumors and give no or only low levels of binding to MUC1 released into the serum and no or low levels of binding to normal tissue.

The invention solves the above technical problem by providing recognition molecules comprising an amino acid sequence which contains the amino acid sequence SEQ ID No. 1 or 2 and the amino acid sequence SEQ ID No. 3 or 4 and the amino acid sequence SEQ ID No. 5 or 6, said recognition molecules specifically binding the glycosylated MUC1 tumor epitope.

Mutatis mutandis, the definitions of terms given below also apply to statements given above, those given here and hereinafter.

According to the invention, the term recognition molecule is understood to concern a molecule which, especially under stringent conditions, specifically binds the glycosylated MUC1 tumor epitope. For example, stringent conditions are high salt concentrations and excessive washing using mild detergents such as NP-40 or Tween.

According to the invention, "glycosylated MUC1 tumor epitope" is understood to be an epitope which comprises at least one PDTRP sequence of the MUC1 tandem repeat and is glycosylated with GalNAc or Gal-GalNAc on the PDTRP threonine.

According to the invention, specific binding of the glycosylated MUC1 tumor epitope is understood to be binding of the recognition molecules of the invention, comprising a combination of the following binding properties:

a) Binding in test methods as described in Example 5 to the glycosylated PDTRP region within a MUC1 tandem repeat sequence which consists of 1 to 1.5 tandem repeats (molecule comprised of 30 amino acids, see Example 5) and is glycosylated with GalNAcalphal-O-Thr (referred to as GalNAc hereinbelow) or Galbetal-3GalNAcalfal-O-Thr (referred to as Gal-GalNAc hereinbelow) on the threonine, the binding strength being increased many times over compared to the non-glycosylated peptide of same length and peptide sequence. As defined herein, "increased many times over" means that the binding ratio of the PDTRP-glycosylated MUC1 glycopeptide to nonglycosylated peptide reaches a factor of >4.5 in a test as described in Example 5.1 (using the MUC1 peptide or glycopeptide described therein, having a length of 30 amino acids which corresponds to 1.5 tandem repeats).

b) Binding in test methods as described in Example 5.2 to multiple non-glycosylated MUC1 tandem repeats consisting of at least 3 tandem repeats, preferably 5 tandem repeats.

c) Statistically significantly reduced binding to tumor cell-released MUC1 present in the serum of colon carcinoma patients compared to antibodies of the CA15-3 test (Example 11) and of HMFG-1 (likewise cf. Example 11). The test method used to this end is illustrated in more detail in Example 11.

d) As described in Example 6, the interaction between antigen and recognition molecule is either increased or not influenced by neuraminidase treatment.

e) There is no or barely detectable binding to colon normal tissue and specific strong binding to colon tumor tissue (see Example 6).

Owing to the amino acid sequences being included according to the invention, specified above and hereinbelow, the recognition molecules of the invention have a structure which causes specific interaction of the recognition molecules with MUC1 in the form of specific binding of the glycosylated MUC1 tumor epitope with binding properties as described.

In a preferred embodiment of the invention the recognition molecule comprises an amino acid sequence which contains the amino acid sequence SEQ ID NO. 1, the amino acid sequence SEQ ID NO. 3 and the amino acid sequence SEQ ID NO. 5, said recognition molecule specifically binding the glycosylated MUC1 tumor epitope.

In another preferred embodiment of the invention the recognition molecule comprises an amino acid sequence which contains the amino acid sequence SEQ ID NO. 2, the amino acid sequence SEQ ID NO. 4 and the amino acid sequence SEQ ID NO. 6, said recognition molecule specifically binding the glycosylated MUC1 tumor epitope. Advantageously, said recognition molecules also have at least one of the following properties:

f) An increase in binding by a factor of >20 according to a).

g) Binding to non-glycosylated multiple tandem repeats as under b) with a factor of the ratio of binding to a non-glycosylated MUC1 tandem repeat with 5 tandem repeats to a non-glycosylated MUC1 peptide with one tandem repeat of >8 (sequence of peptides and test method see Example 5). The test method for the determination of said factor is illustrated in more detail in Example 5.2.

h) An increase of binding strength by increasing the number of glycosylated tandem repeats (multiple glycosylated PDTR region) (see Example 5.3).

Advantageously, other preferred recognition molecules possess all of the binding properties a) through h).

The recognition molecules according to the invention combine the properties described above, thus being advantageous in tumor diagnosis and therapy. They differ from well-known antibodies not only as a result of their new sequences, but also as a result of their fine specificity to MUC1 by specifically binding the glycosylated MUC1 tumor epitope, exhibiting minor binding to MUC1 in the serum of colon carcinoma patients, virtually no binding to normal colon tissue and strong binding to colon tumor tissue. Moreover, the recognition molecules of the invention recognize colon tumors already as in situ carcinomas, but fail to recognize mild dysplasias, thereby differentiating between dangerous tumors and benign diseases. Given such properties and their high affinity, they are particularly suitable for therapeutic as well as diagnostic use, thereby offering advantages over well-known MUC1 antibodies.

Amongst the wide variety of well-known MUC1 antibodies, there has been no antibody having corresponding properties as yet, which is why the combination of properties of the recognition molecules according to the invention is surprising.

As can be seen from the above, the recognition molecules according to the invention are superior to conventional MUC1 antibodies.

Consequently, conventional antibodies have significant disadvantages compared to the recognition molecules of the invention, as will be briefly exemplified below.

Examples of differences in fine specificity: in the investigations set forth in Example 5.1, HMFG-1 (U.S. Pat. No. 5,804,187, U.S. Pat. No. 6,315,997) and C595 (WO 02/44217) bind to MUC1 peptides independently of any glycosylation and therefore do not bind to the glycosylated MUC1 tumor epitope. For example, HMFG-1 also binds to normal colon tissue. As can be seen, they do not exhibit the advantageous binding of the recognition molecules according to the invention. According to the test in Example 5.1, SM3 (U.S. Pat. No. 5,683,674) obtained by immunization with MUC1 derived from human non-tumor material (milk fat droplets) binds glycosylated and non-glycosylated MUC1-derived peptides to virtually the same extent, with a slight increase by a factor of about 1.5, thus failing to exhibit such advantageous binding to the tumor epitope. In addition, SM3 fails to show any pronounced dependence on the number of MUC1 tandem repeats, neither non-glycosylated nor glycosylated ones (Examples 5.2 and 5.3). DF3 has been described as an MUC1-specific antibody binding to MUC1-derived peptides preferably in a glycosylation-independent fashion (WO 93/20841, U.S. Pat. No. 5,506,343). Furthermore, binding of DF3 to MUC1 or MUC1-bearing tumor cells is dramatically reduced or entirely inhibited by neuraminidase treatment (Dai J. et al., 1998; Hinoda et al., 1992). In addition, HMFG-1 and DF3 give strong binding to tumor MUC1 in serum, especially in mammary carcinoma patients, but also in colon carcinoma patients (see Example 11). Thus, they fail to exhibit the advantageous binding properties of the recognition molecules according to the invention.

The recognition molecules are characterized according to the foregoing definition, essentially via their binding properties with respect to colon normal and tumor tissues. As can be seen, said recognition molecules are advantageous in therapy and diagnostics of colon tumors and metastases thereof when compared to conventional anti-MUC1 antibodies. However, said recognition molecules are advantageous not only in the treatment and diagnosis of colon carcinomas and other gastrointestinal tumors, but also in other tumor diseases and metastases, preferably MUC1-positive tumor diseases and metastases, e.g. mammary carcinomas, gastrointestinal tumors, including colon carcinomas, stomach carcinomas, large intestine cancer and small intestine cancer, pancreas carcinomas, ovarian carcinomas, lung cancer, renal cell carcinomas, multiple myeloma and/or metastases thereof. This is substantiated by the data of Example 6, demonstrating specific binding of the recognition molecules to tumor cells in various tumor diseases. The detailed description of the binding properties with respect to colon carcinomas is to substantiate the advantages and establish suitable parameters for the binding characteristics of the recognition molecules according to the invention.

In a preferred embodiment a recognition molecule of the invention specifically binding the glycosylated MUC1 tumor epitope comprises:

a) a first amino acid sequence which contains the amino acid sequence SEQ ID No. 1 or 2 and the amino acid sequence SEQ ID No. 3 or 4 and the amino acid sequence SEQ ID No. 5 or 6; and b) a second amino acid sequence which contains the amino acid sequence SEQ ID No. 7 or 8 and the amino acid sequence SEQ ID No. 9 or 10 and the amino acid sequence SEQ ID No. 11 or 12.

The first and the second amino acid sequence can be present on one or more and preferably on two polypeptides.

For the sake of simplicity, the recognition molecules of the invention specifically binding the glycosylated MUC1 tumor epitope in the meaning of the invention will also be referred to as MUC1-binding or specific recognition molecules hereinbelow.

The preferred MUC1-binding recognition molecules according to the invention are characterized in that a defined set of single amino acid sequences is included therein. The combination of amino acid sequences results in a structure of said recognition molecules which—as a property—exhibits the above-described combination of binding properties with respect to the glycosylated MUC1 tumor epitope. The amino acid sequence of said recognition molecules includes one or two triplets of defined sequences. These sequences represent the binding domains and define the specificity of the recognition molecules. The 1-triplet recognition molecule comprises the amino acid sequence SEQ ID NO. 1 or 2, the amino acid sequence SEQ ID NO. 3 or 4 and the amino acid sequence SEQ ID NO. 5 or 6. MUC1-specific recognition molecules defined by two triplets comprise the amino acid sequence SEQ ID NO. 1 or 2, the amino acid sequence SEQ ID NO. 3 or 4 and the amino acid sequence SEQ ID NO. 5 or 6 for the first triplet, and the amino acid sequence SEQ ID NO. 7 or 8, the amino acid sequence SEQ ID NO. 9 or 10 and the amino acid sequence SEQ ID NO. 11 or 12 for the second triplet. The first and the second triplet can be present either on one or on more polypeptide chains which, in the latter case, together form the binding recognition molecule. Further, in the meaning of the invention, these triplets are referred to as triplet sequence 1 for the first amino acid sequence being included and as triplet sequence 2 for the second amino acid sequence being included; see definition a) and b) of the description above. According to the invention, the recognition molecule can be an antibody, particularly a murine, chimeric or human IgG or IgM, an scFv structure or another antibody-derived fragment such as Fab, F(ab)$_2$, Fv or F(v)$_2$ fragments.

In a preferred embodiment the MUC1-binding recognition molecules of the invention comprise the amino acid sequence SEQ ID NO. 1, the amino acid sequence SEQ ID NO. 3 and the amino acid sequence SEQ ID NO. 5 as triplet sequence 1.

In another preferred embodiment the MUC1-binding recognition molecules of the invention comprise the amino acid sequence SEQ ID NO. 2, the amino acid sequence SEQ ID NO. 4 and the amino acid sequence SEQ ID NO. 6 as triplet sequence 1.

In a preferred embodiment the MUC1-binding recognition molecules of the invention comprise the amino acid sequence SEQ ID NO. 1, the amino acid sequence SEQ ID NO. 3 and the amino acid sequence SEQ ID NO. 5 as triplet sequence 1, and the amino acid sequence SEQ ID NO. 7, the amino acid sequence SEQ ID NO. 9 and the amino acid sequence SEQ ID NO. 11 as triplet sequence 2.

In another preferred embodiment the MUC1-binding recognition molecules of the invention comprise the amino acid sequence SEQ ID NO. 2, the amino acid sequence SEQ ID NO. 4 and the amino acid sequence SEQ ID NO. 6 as triplet sequence 1, and the amino acid sequence SEQ ID NO. 8, the amino acid sequence SEQ ID NO. 10 and the amino acid sequence SEQ ID NO. 12 as triplet sequence 2.

Another embodiment of the invention relates to recognition molecules wherein at least one amino acid sequence of SEQ ID Nos. 1 to 12 has been modified by mutation, deletion and/or insertion, but wherein the property of binding specificity towards the glycosylated MUC1 tumor epitope continues to exist. Advantageously, this is utilized to improve the recognition molecules, e.g. with respect to affinity, solubility and/or producibility.

In a preferred embodiment, modification of a recognition molecule is effected by one or more mutations in one or more amino acid sequences selected from SEQ ID Nos. 1 to 12, wherein single amino acids are replaced by amino acids having analogous physicochemical properties which, advantageously, do not fundamentally change the three-dimensional structure of the binding domain in the recognition molecules, so that the MUC1 specificity of the recognition molecules is retained. Amino acids having analogous physicochemical properties in the meaning of the invention can be summarized into 6 separate groups and are illustrated in Table 1.

TABLE 1

| Amino acids with analogous physicochemical properties regardless of molecular size | |
|---|---|
| Property or functional group | Amino acid |
| aliphatic | glycine |
| | alanine |
| | valine |
| | leucine |
| | isoleucine |

TABLE 1-continued

Amino acids with analogous physicochemical
properties regardless of molecular size

| Property or functional group | Amino acid |
| --- | --- |
| hydroxy group | serine |
| | threonine |
| carboxyl group | aspartic acid |
| | glutamic acid |
| amide group | asparagine |
| | glutamine |
| amino group | lysine |
| | arginine |
| aromatic | phenylalanine |
| | tyrosine |
| | tryptophane |

In another preferred embodiment of the recognition molecules of the invention specifically binding MUC1, at least one amino acid sequence of amino acid sequences SEQ ID Nos. 1, 2, 3, 4, 7, 8, 11 and/or 12 is replaced by canonical structure variants or equivalent structures having the amino acid sequences SEQ ID Nos. 13 to 31, with SEQ ID NO. 1 or 2 being replaced by a sequence of sequences SEQ ID Nos. 13 to 20 (CDRH1), SEQ ID NO. 3 or 4 by a sequence of sequences SEQ ID Nos. 21 to 23 (CDRH2), SEQ ID NO. 7 or 8 by a sequence of sequences SEQ ID Nos. 24 to 29 (CDRL1), and SEQ ID NO. 11 or 12 by a sequence of sequences SEQ ID Nos. 30 to 31 (CDRL3).

The general relationship between an amino acid sequence and the tertiary structure of loops formed by these sequences is well-known to those skilled in the art and has been investigated in detail [Rooman et al., 1989; Martin, Thornton, 1996]. Immunoglobulins represent a unique example. By analyzing the loop conformations of the hypervariable regions (complementarity determining regions, CDRs) in the light and heavy chains of antibody molecules, so-called canonical classes have been defined [Chothia, Lesk, 1987; Chothia et al., 1986, 1989, 1992; Wu, Cygler, 1993]. On this basis, the canonical structure variants SEQ ID Nos. 13 to 31 of SEQ ID Nos. 1, 2, 3, 4, 7, 8, 11 and 12 have been derived. According to the invention, equivalent canonical structure variants are understood to be amino acid sequences differing from the initial sequences to such an extent that at least one amino acid is replaced in well-defined positions without changing the canonical class.

The amino acid sequences SEQ ID Nos. 1 to 12 or their modifications in a MUC1-specific recognition molecule in the meaning of the invention form spatial structures, e.g. so-called loops which are characterized by possessing a definable tertiary structure and/or quaternary structure. The binding region of a recognition molecule with the MUC1 antigen is formed by amino acid residues which are provided by up to six variable loops on the surface of the molecule and specifically interact with MUC1.

In another embodiment of the invention, recognition molecules specifically binding MUC1 are provided, wherein at least one sequence of the triplet sequences not immediately involved in the interaction with the MUC1 antigen is omitted.

In another embodiment the recognition molecules comprise at least one of the amino acid sequences SEQ ID Nos. 1 to 12 or the above-described variants thereof in duplicate or multiplicity, and such doubles may also be present in the form of variants of the same amino acid sequence. All recognition molecules described in this section advantageously recognize the MUC1 antigen in a specific manner.

For easier comprehension, the above recognition molecules as well, which, strictly speaking, do not bear any triplet sequences as a result of omitting or multiplying sequences, will nevertheless be referred to as triplet sequence 1 or triplet sequence 2 hereinafter.

In another embodiment the recognition molecules of the invention specifically binding the glycosylated MUC1 tumor epitope comprise amino acid sequences having a homology of at least 60%, preferably 70%, more preferably 80%, especially preferably 90%, with respect to the sequences SEQ ID Nos. 1 to 12.

Furthermore, the recognition molecules in the meaning of the invention may comprise framework sequences which separate the comprising amino acid sequences, i.e. amino acid sequence SEQ ID NO. 1 or 2 and amino acid sequence SEQ ID NO. 3 or 4 and amino acid sequence SEQ ID No. 5 or 6, or the above-described variants thereof, and framework sequences which separate the amino acid sequence SEQ ID No. 7 or 8 and the amino acid sequence SEQ ID No. 9 or 10 and the amino acid sequence SEQ ID No. 11 or 12, or the above-described variants thereof. The first and the second amino acid sequence can be present on one or more and preferably two polypeptide chains. In the meaning of the invention, such framework sequences are also referred to as spacers and may vary in length and sequence. This expressly includes those recognition molecules wherein not all of the amino acid sequences SEQ ID Nos. 1 to 12 or the above-described variants thereof are separated by spacers. Moreover, the recognition molecules preferably have additional flanking amino acid sequences likewise referred to as framework sequences in the meaning of the invention.

More specifically, the framework sequences have the function of forming the above-described amino acid sequences responsible for or involved in MUC1-specific binding of the recognition molecules into a suitable configuration and spatial structure so as to allow binding to MUC1. It can be envisaged that the amino acid sequences SEQ ID NO. 1 to NO. 12 without at least one additional amino acid sequence as framework sequence are incapable of binding the MUC1 antigen in a specific fashion in the meaning of the invention. Moreover, the framework sequences may provide the recognition molecules with e.g. the required biological and chemical stability, so that the spatial structure can be built up effectively and maintained for function and use in a suitable functional form which includes MUC1 binding.

In a preferred embodiment the triplet sequences are introduced in existing proteins by replacement of amino acid sequences and/or by addition, the existing protein sequences serving as framework sequences in the meaning of the invention, or framework sequences being taken from suitable proteins. For example, such framework sequences can be modified by means of mutations, deletions or insertions. Methods of molecular biology, biochemistry and protein engineering per se known to those skilled in the art can be employed for this purpose. Preferred proteins for this purpose are proteins of the immunoglobulin superfamily, protease inhibitors, lectins, helix bundle proteins and lipocalins, such as disclosed in: Nygren and Uhlen, 1997; Nuttall S D et al., 1999; and Skerra, 2000.

In another preferred embodiment the framework sequences are antibody framework sequences from one or various species or amino acid sequences mimicking the consensus sequence of framework sequences of murine, human antibodies and/or antibodies of other mammals. A consensus sequence is an idealized sequence wherein the most frequently occurring amino acid is representative in each position when comparing a large number of existing sequences, e.g. from antibody data bases. The recognition molecules preferred herein are characterized in that the framework sequences for the first triplet sequence 1 comprising the amino acid sequence SEQ ID NO. 1 or 2, the amino acid sequence SEQ ID NO. 3 or 4 and the amino acid sequence SEQ ID NO. 5 or 6, or the above-described variants, are antibody framework sequences of the variable heavy chain, $V_H$, in the literature also referred to as framework sequences, and the framework sequences for the triplet sequence 2 comprising the amino acid sequence SEQ ID NO. 7 or 8, the amino acid sequence SEQ ID NO. 9 or 10 and the amino acid sequence SEQ ID NO. 11 or 12, or the above-described variants thereof, are antibody framework sequences of the variable light chain, $V_L$.

Also preferred are antibody framework sequences of antibodies from mammals, with antibody framework sequences of human and/or murine origin being particularly preferred. The framework sequences can be combined from antibody framework sequences of various species. Such antibody framework sequences are well-known to those skilled in the art and can be obtained from various data bases such as the Kabat data base (immuno.bme.nwu.edu) or the National Center for Biotechnology Information data base (www.ncbi.nlm.nih.gov). Likewise, these antibody framework structures can be extended by additional amino acids and/or modified by one or more mutations, e.g. deletions and/or insertions, with specific binding to the glycosylated MUC1 tumor epitope being retained.

When combining the triplet sequences with antibody framework sequences in a preferred variant of the invention, the recognition molecule represents a variable chain of an antibody or a structure derived therefrom.

Particularly preferred antibody framework sequences as framework sequences in the meaning of the invention are the amino acid sequences corresponding to FRH1, FRH2, FRH3 and FHR4 in Table 2 for the variable heavy chain and the amino acid sequences corresponding to FRL1, FRL2, FRL3 and FRL4 in Table 2 for the variable light chain, the amino acid sequences of the triplet sequences 1 and 2 with SEQ ID Nos. 1 to 12 corresponding to the corresponding CDR regions of the antibodies. The variable heavy (VH) and light (VL) antibody chains, respectively, are composed as follows: $V_H$: FRH1-CDRH1-FRH2-CDRH2-FRH3-CDRH3-FRH4, and $V_L$: FRL1-CDRL1-FRL2-CDRL2-FRL3-CDRL3-FRL4. Table 2 illustrates the positions in detail. The positions of the individual amino acids or amino acid sequences correspond to the numbering of amino acids in antibody molecules according to Kabat.

TABLE 2

| Name | Position range | Pos. | Amino acid or amino acid sequence |
|---|---|---|---|
| FRH1 | 1 to 30 | 1 | E |
| | | 2 | V |
| | | 3 | K |
| | | 4 | L |
| | | 5 | V |
| | | 6 | E |
| | | 7 | S |
| | | 8 | G |
| | | 9 | G |
| | | 10 | G |
| | | 11 | L |
| | | 12 | V |
| | | 13 | Q |
| | | 14 | P |
| | | 15 | G |
| | | 16 | G |
| | | 17 | S |
| | | 18 | M |
| | | 19 | K |
| | | 20 | L |
| | | 21 | S |
| | | 22 | C |
| | | 23 | A or V |
| | | 24 | A, V, S or T |
| | | 25 | S |
| | | 26 | G |
| | | 27 | Y, F, S or D |
| | | 28 | T |
| | | 29 | F, L or I |
| | | 30 | S |
| CDRH1 | 31 to 35 | | SEQ ID NO. 1 or 2 and variants |
| FRH2 | 36 to 49 | 36 | W |
| | | 37 | V |
| | | 38 | R |
| | | 39 | Q |
| | | 40 | S |
| | | 41 | P |
| | | 42 | E |
| | | 43 | K |
| | | 44 | G |
| | | 45 | L |
| | | 46 | E |
| | | 47 | W |
| | | 48 | V |
| | | 49 | A |
| CDRH2 | 50 to 65, with positions 52a, 52b and 52c introduced in addition | | SEQ ID NO. 3 or 4 and variants |
| FRH3 | 66 to 94 | 66 | R |
| | | 67 | F |
| | | 68 | T |
| | | 69 | I |
| | | 70 | S |
| | | 71 | R |
| | | 72 | D |
| | | 73 | D or V |
| | | 74 | S |
| | | 75 | K |
| | | 76 | S |
| | | 77 | S |
| | | 78 | V |
| | | 79 | Y or S |
| | | 80 | L |
| | | 81 | Q |
| | | 82 | M |
| | | 82a | N |
| | | 82b | N |
| | | 82c | L |
| | | 83 | R |
| | | 84 | A or V |
| | | 85 | E |
| | | 86 | D |
| | | 87 | T |
| | | 88 | G |
| | | 89 | I |
| | | 90 | Y |
| | | 91 | Y |
| | | 92 | C |
| | | 93 | T |
| | | 94 | R, G, N, K or S |
| CDRH3 | 95 to 102; pos. 100 non-existent and pos. 99 partially nonexistent | | SEQ ID NO. 5 or 6 and variants |
| FRH4 | 103 to 113 | 103 | W |
| | | 104 | G |
| | | 105 | Q |
| | | 106 | G |

TABLE 2-continued

| Name | Position range | Pos. | Amino acid or amino acid sequence |
|---|---|---|---|
| | | 107 | T |
| | | 108 | T |
| | | 109 | L |
| | | 110 | T |
| | | 111 | V |
| | | 112 | S |
| | | 113 | S or A |
| FRL1 | 1 to 23 | 1 | D |
| | | 2 | I, V or L |
| | | 3 | V |
| | | 4 | M or L |
| | | 5 | T |
| | | 6 | Q |
| | | 7 | T or A |
| | | 8 | P or A |
| | | 9 | L or F |
| | | 10 | S |
| | | 11 | L or N |
| | | 12 | P |
| | | 13 | V |
| | | 14 | S or T |
| | | 15 | L |
| | | 16 | G |
| | | 17 | D or T |
| | | 18 | Q or S |
| | | 19 | A |
| | | 20 | S |
| | | 21 | I |
| | | 22 | S |
| | | 23 | C |
| CDRL1 | 24 to 34, with positions 27a, 27b, 27c, 27d and 27e introduced in addition | | SEQ ID NO. 7 or 8 and variants |
| FRL2 | 35 to 49 | 35 | W |
| | | 36 | Y |
| | | 37 | L |
| | | 38 | Q |
| | | 39 | K |
| | | 40 | P |
| | | 41 | G |
| | | 42 | Q or L |
| | | 43 | S |
| | | 44 | P |
| | | 45 | K or Q |
| | | 46 | L |
| | | 47 | L |
| | | 48 | I or V |
| | | 49 | Y |
| CDRL2 | 50 to 56 | | SEQ ID NO. 9 or 10 and variants |
| FRL3 | 57 to 88 | 57 | G |
| | | 58 | V |
| | | 59 | P |
| | | 60 | D |
| | | 61 | R |
| | | 62 | F |
| | | 63 | S |
| | | 64 | G or S |
| | | 65 | S |
| | | 66 | G |
| | | 67 | S |
| | | 68 | G |
| | | 69 | T |
| | | 70 | D |
| | | 71 | F |
| | | 72 | T |
| | | 73 | L |
| | | 74 | K or R |
| | | 75 | I |
| | | 76 | S |
| | | 77 | R |
| | | 78 | V |
| | | 79 | E |
| | | 80 | A |
| | | 81 | E |
| | | 82 | D |
| | | 83 | L or V |
| | | 84 | G |
| | | 85 | V |
| | | 86 | Y |
| | | 87 | Y |
| | | 88 | C |
| CDRL3 | 89 to 97 | | SEQ ID NO. 11 or 12 and variants |
| FRL4 | 98 to 108 | 98 | F |
| | | 99 | G |
| | | 100 | G or D |
| | | 101 | G |
| | | 102 | T |
| | | 103 | K |
| | | 104 | L |
| | | 105 | E |
| | | 106 | I or L |
| | | 106a | K |
| | | 107 | R |
| | | 108 | A |

The amino acid sequences SEQ ID Nos. 32 and 33 correspond to amino acid sequences with preferred framework sequences for the variable heavy chain. The amino acid sequences SEQ ID Nos. 34 and 35 correspond to amino acid sequences with preferred framework sequences for the variable light chain. Preferred is the combination SEQ ID NO. 32 and 34. Also preferred is the combination SEQ ID NO. 33 and 35.

The techniques and methods to be used in the production of these sequences are well-known to those skilled in the art, and a person skilled in the art will be able to select suitable framework sequences and/or mutations.

In the meaning of the invention, MUC1-specific recognition molecules can be present in different formats. The basic structure of the recognition molecule is one (or more) polypeptide chain(s) comprising the above-described inventive triplet sequence 1 or triplet sequences 1 and 2 and framework sequences. For example, the amino acid sequence of the variable heavy chain is linked with the framework sequences and triplet sequences 1, and the amino acid sequence of the variable light chain is linked with the framework sequences and the triplet sequences 2 in a non-covalent or covalent fashion and can be situated on one or more polypeptide chains. A plurality of polypeptide chains can be present in covalently linked—e.g. via disulfide bridges—or non-covalently linked form as recognition molecule.

In particular, the various inventive formats of recognition molecules include linking of said triplet sequences with amino acid sequences beyond the framework sequences described above. In a preferred variant the recognition molecules according to the invention therefore comprise further accessory sequences apart from the triplet sequences and framework sequences. More specifically, accessory sequences are amino acid sequences which primarily are not involved in the spatial configuration of the triplet sequences, such as in the form of framework sequences, but may have an advantageous influence thereon as a result of secondary or tertiary interactions. For example, accessory sequences in the form of constant domains of an antibody will stabilize the antibody, causing dimerization, thereby effecting improved binding of the antibody, or, for instance, fusion of an scFv with a domain of a bacteriophage coat protein causes an activity increase of scFv binding as disclosed in Jensen K B et al., 2002, for example.

In a preferred embodiment the recognition molecules comprise amino acid sequences with framework sequences on an antibody basis and further accessory sequences in addition to the triplet sequences. In particular, the accessory sequences assume at least one of the following functions:

a) linking a triplet sequence with its correspondingly suited framework sequences with at least one other triplet sequence with its correspondingly suited framework sequences in order to create or improve binding capability;

b) stabilization of domains, e.g. by means of a linker between two protein domains or amino acid sequences which undergo interaction with others in the same or in a second chain;

c) effector functions for immunological purposes, e.g. by fusion with the Fc portion of antibodies, chemokines, cytokines, growth factors or portions thereof, or antibodies having a different specificity, or fragments thereof, for the recruitment of cells of the immune system, e.g. macrophages or components of the complement system;

d) fusion with tags, e.g. multimerization sequences—for example, μ-tail sequence from IgM or association domain from p53 or MBL—for multimerization of the MUC1-binding portions for multivalent binding or for purification of recognition molecules, e.g. His-tag, or for detection, e.g. myc-tag, or for labelling or chelating of recognition molecules e.g. by high-lysine sequences. Suitable structures are well-known to those skilled in the art or can be derived from the prior art by logical deduction.

Further preferred embodiments are recognition molecules according to the invention comprising the following formats: single-chain antibody fragment (scFv), Fv fragment, Fab fragment, $F(ab)_2$ fragment, multibody (dia-, tria-, tetrabody), immunoglobulin of the IgG, IgM, IgA, IgE, IgD isotypes or subclasses thereof, e.g. IgG1, or immunoglobulin derived recognition molecules comprising at least one constant domain.

According to the invention, “multibody” is understood to be a single-chain antibody fragment, with the variable heavy chain and the variable light chain being linked directly or via a linker in such a way that association of the $V_H$ and $V_L$ takes place in an intermolecular fashion only, rather than intramolecular, thereby forming dia-, tria- and/or tetrabodies.

According to the invention, a “linker” is understood to be an amino acid or an amino acid sequence having up to 20 amino acids which links the variable heavy chain and the variable light chain in a single-chain antibody fragment.

In a preferred embodiment the recognition molecules of the invention are composed of a heavy and a light polypeptide chain, each of the amino acid sequences of the heavy and light chains comprising one of the above-described triplet structures representing the CDR regions of the antibody, the corresponding antibody framework sequences representing the framework sequences of the antibody, and accessory sequences comprising at least one of the constant domains of the antibody isotype. The two chains can form covalent bonds with each other. The constant regions and variable regions may include sequences of antibodies from one or more species. Portions of constant domains or complete constant domains can be deleted or mutated in order to e.g. modify the effector function of accessory sequences, e.g. to prevent or improve binding to Fc receptors. In a preferred embodiment the recognition molecule is a murine, chimerized, humanized or human antibody or antibody fragment. For example, chimerization is effected by linking the variable antibody domains with constant antibody domains or fragments of a constant domain of antibodies from different species. Preferred are sequences of constant domains of human antibodies. Examples of murine antibodies are mIgG-Panko1 consisting of the sequences SEQ ID Nos. 60 and 62, and mIgG-Panko2 consisting of the sequences SEQ ID NO. 61 and 63. Examples of chimeric antibodies are the recognition molecules cIgG-Panko1 consisting of the sequences SEQ ID Nos. 64 and 68, and cIgG-Panko2 consisting of the sequences SEQ ID Nos. 65 and 69.

The antibody framework sequences can be selected in such a way that the sequences are largely homologous to human antibody sequences. Selection as to the species origin of the framework sequences will also depend on the use. Thus, for therapeutic use in particular fields, highest possible levels of human framework sequences are preferred, particularly in those cases where human anti-mouse antibody response (HAMA) is to be avoided. In other therapeutic fields, a xeno-component is advantageous because it effects additional stimulation of the immune system. A combination of both is particularly suitable in some cases, especially in those cases where a xeno-component is advantageous in initial immunization and a species-compatible, i.e. a human component, is advantageous in later uses.

Homology to human consensus sequences is preferred, with HuHIII being preferred for the variable heavy chain, and HuKII being preferred for the variable light chain. Particularly preferred is homology to human germ line sequences which are known to those skilled in the art and can be obtained from the V BASE data base (www.mrccpe-.cam.ac.uk) or from the data base of the National Center for Biotechnology Information (www.ncbi.nlm.nih.gov).

The techniques and methods to be used in the production of these sequences are well-known to those skilled in the art, and a person skilled in the art will also be able to select suitable human sequences and/or perform possibly required mutations of said sequences.

In another embodiment the triplet sequences generally corresponding to the binding loops (CDR regions) and preferably having high homologies to the corresponding sequence regions in the human germ line sequence are additionally adapted thereto step by step, using simple mutations, without impairing the specific binding to the glycosylated MUC1 tumor epitope. Recognition molecules having these sequences will be referred to as partially human antibodies or antibody fragments herein.

In another preferred embodiment, specific amino acids of antibody framework sequences of a species are replaced by others in order to generate less immunogenic regions in general. This involves technologies per se known to those skilled in the art, e.g. technologies of humanization, e.g. CDR grafting, resurfacing, chain shuffling with mutations and deimmunization by mutation or deletion of human MHC epitopes.

In a preferred embodiment, this involves an IgM-derived recognition molecule having the corresponding constant domains of an IgM, preferably human sequences. In the meaning of the invention, immunoglobulins are composed of a heavy chain and a light chain of an antibody, and 2 light chains and 2 heavy chains preferably represent a unit. Immunoglobulins of the IgM type usually consist of 5 such units additionally linked via the J chain to form disulfide bridges.

In a particularly preferred embodiment the J chain is absent, with multimerization of the subunits likewise taking place, in which case hexa- and pentameric structures can be present. Examples of chimeric IgM antibodies are the recognition molecules cIgM-Panko1 consisting of the sequences SEQ ID Nos. 66 and 68, and cIgM-Panko2 consisting of the sequences SEQ ID Nos. 67 and 69.

In a preferred embodiment of such recognition molecules, single-chain antibody fragments are involved, comprising a triplet structure 1 with the corresponding antibody framework sequences described above, which represent the CDR regions of the antibody and framework sequences of the variable domain of the heavy chain of antibodies, and a triplet structure 2 with the corresponding antibody framework sequences described above, which represent the CDR regions of the antibody and framework sequences of the variable domain of the light chain of antibodies, which are covalently linked in the form of a fusion protein. Here, the sequences are linked directly or via a linker.

Preferred in this case are scFv formats with no linker or with a linker 1 to 9 amino acids in length. The scFv antibodies form multimeric structures (for example, dia-, tria-, tetrabodies) which, in the meaning of the invention, are also referred to as multibodies and exhibit higher avidity to the glycosylated MUC1 tumor epitope as a result of multivalence. As set forth in Example 8, the multibody having the sequence SEQ ID NO. 45 binds many times better to the breast tumor cell line T47D in a radioactive cell binding test than the scFv antibody having the sequence SEQ ID NO. 36. These multivalent constructs in a dia-/triabody format are particularly preferred embodiments of the invention, being advantageous in tumor therapy as a result of improved pharmacokinetic properties. Preferred sequences are the sequences SEQ ID Nos. 36 to 47. Particularly preferred are the sequences SEQ ID Nos. 48 to 59.

Particularly preferred embodiments of the recognition molecules according to the invention are recognition molecules comprising the sequences SEQ ID Nos. 48 to 59, SEQ ID Nos. 61, 63, 65 or 69, because they combine all of the binding properties a) to h), as will be described in more detail in the examples.

In another preferred embodiment the recognition molecules are fused, chemically coupled, covalently or non-covalently associated with (i) immunoglobulin domains of various species, (ii) enzyme molecules, (iii) interaction domains, (iv) signal sequences, (v) fluorescent dyes, (vi) toxins, (vii) catalytic antibodies, (viii) one or more antibodies or antibody fragments with different specificity, (ix) cytolytic components, (x) immunomodulators, (xi) immunoeffectors, (xii) MHC class I or class II antigens, (xiii) chelating agents for radioactive labelling, (xiv) radioisotopes, (xv) liposomes, (xvi) transmembrane domains, (xvii) viruses and/or cells. Cells can be bacterial, yeast, plant, insect and/or mammal cells. Mammal cells are preferred, e.g. murine, human or hamster cells. Effector cells are particularly preferred. "Effector cells" in the meaning of the invention are cells, preferably human cells, which mediate immune reactions, such as macrophages, dendritic cells, lymphocytes and NK cells. In particular, the recognition molecules can also be fused with a tag allowing detection of the recognition molecule and purification thereof, such as myc-tag or His-tag. In the meaning of the invention, such combined molecules will be referred to as "constructs." Technologies for the production of such constructs are well-known to those skilled in the art, and a person skilled in the art will be able to select suitable sequences and components and link them with the recognition molecules of the invention in a suitable manner.

In another preferred embodiment the above-described recognition molecules based on antibodies or antibody fragments are fused with peptides or proteins not derived from immunoglobulins. For example, the multimerization domain of a non-immunoglobulin molecule is fused with an scFv, especially the C-terminal end of the $\alpha$-chain of the C4 binding protein, as described in Tonye Libyh M. et al., 1997, thereby constructing a multivalent recognition molecule.

In another embodiment, an scFv is fused with a transmembrane domain of a non-immunoglobulin molecule, e.g. with the transmembrane domain of c-erb B2, h-PDGFR, human transferrin receptor, or human asialoglycoprotein receptor (Liao et al., 2000), thereby enabling expression of binding molecules on the surface of cells.

Another preferred embodiment of the invention comprises recognition molecules according to the invention, additionally comprising amino acid sequences specifically binding to macrophages or other immunoeffector cells. For example, the recognition molecules of the invention further comprise an antibody binding site against CD64, and, in the form of a bispecific antibody or antibody fragment (diabodies), binding of macrophages to MUC1-positive tumor cells takes place, resulting in combatting and/or destruction thereof.

A preferred embodiment of the invention relates to radiolabelled MUC1-specific recognition molecules. One preferred form involves recognition molecules based on antibodies or antibody fragments. Another preferred embodiment involves radiolabelled recognition molecules of the invention in single-chain format (including the form of dia-, tria-, tetrabodies). Other preferred forms are radiolabelled single-chain antibody fragments and complete immunoglobulins, e.g. inventive murine, chimeric or humanized IgG or IgM antibodies or humanized antibody fragments. It goes without saying that the invention is not restricted to these antibodies, said radioactive labels and said formats of antibodies.

In a preferred embodiment, radiolabelled or toxin-labelled recognition molecules are concerned, which have xenogenic components, e.g. murine components, in the Fc portion of the antibody, so that the radioactive antibodies have a shorter residence time in the blood of a human, being eliminated more rapidly. Examples of such recognition molecules are mIgG-Panko1 consisting of the sequences SEQ ID Nos. 60 and 62, and mIgG-Panko2 consisting of the sequences SEQ ID Nos. 61 and 63. Another preferred variant are antibody-based recognition molecules, wherein the murine components are minimized, but have those murine components included that are responsible for removal from the blood (clearance). Ways of determining the appropriate components are well-known to those skilled in the art.

Antibody fragments such as the preferred multivalent scFv fragments, especially with no or very short linker, offer an advantage in the targeting of solid tumors compared to intact monoclonal antibodies. With intact antibodies exhibiting specific accumulation within the tumor area in biodistribution studies, an inhomogeneous antibody distribution with primary accumulation in the peripheral regions is noted when precisely investigating the tumor. Due to tumor necroses, inhomogeneous antigen distribution and increased interstitial tissue pressure, it is not possible to reach central portions of the tumor with such antibody constructs. In contrast, smaller antibody fragments show rapid tumor labelling, penetrate deeper into the tumor, and also, are removed relatively rapidly from the bloodstream. However, the dissociation constant of monovalent antibody fragments such as Fabs or scFv frequently is excessively low, resulting in a short residence time on the tumor cells. For this reason, multivalent antibody constructs such as multibodies (diabodies, tria-/tetrabodies), F(ab')$_2$ and other minibodies (multivalent antibody constructs consisting of binding domain and multimerization sequence, e.g. scFv and CH3 domain of an IgG) offer many advantages in tumor therapy. Multivalent constructs in a dia-/triabody format (multibodies) are preferred embodiments of the invention, they are advantageous in tumor therapy as a result of improved pharmacokinetic properties and have been further developed for use in tumor therapy. They can be used as vehicles for specific accumulation of e.g. cytotoxic substances such as chemotherapeutic agents or radionuclides in a tumor. By suitably selecting the radionuclides, it is possible to destroy tumor cells over a distance of several cell diameters, so that even antigen-negative tumor cells in a tumor area can be covered and poor penetration of antibodies into solid tumors can be compensated at least in part.

A particularly preferred embodiment of the invention involves radiolabelled multibodies which combine particularly advantageous pharmacokinetic properties and, in combination, have improved tumor retention, tumor penetration, serum half-life and serum to tumor distribution ratio compared to complete immunoglobulins and scFv. Further advantages are high avidity and bacterial expression, allowing low-cost production of such recognition molecules. Advantageously, this specific format of recognition molecules according to the invention is therefore suitable for use preferably in the treatment of small primary tumors, metastases and minimal residual diseases.

A preferred embodiment of the invention involves non-radiolabelled recognition molecules. One preferred form involves recognition molecules based on antibodies or antibody fragments.

Other preferred embodiments are toxin- or cytostatic agent-coupled chimerized or humanized IgG- and IgM-based recognition molecules of the invention and, in particular, multi-bodies (dia-, tria-, tetrabodies) having particularly advantageous pharmacokinetic properties as set forth above.

Another preferred embodiment involves liposomes which are loaded with e.g. toxins or cytostatic agents and bear recognition molecules of the invention on the surface thereof.

A person skilled in the art will be able to select suitable radioisotopes, toxins and cytostatic agents. Suitable techniques, methods, dosages and formulations are well-known to those skilled in the art.

Another preferred embodiment of the invention involves effector cells of the immune system having recognition molecules of the invention bound on the surface thereof, which direct/address the effector cells to MUC1-bearing tumor cells, thereby mediating control and/or destruction thereof. Preferred effector cells are macrophages, dendritic cells and NK cells obtained from the patient and coupled ex vivo with the recognition molecules. Also preferred are cell lines of these types of cells. Linking is effected e.g. by means of bispecific recognition molecules which, in addition to MUC1-specific components, comprise amino acids which mediate binding to the effector cells. For example, these are bispecific antibodies, complement components or constant domains of antibodies.

Another preferred embodiment involves macrophages from a patient which, following collection, are coupled with a bispecific antibody, e.g. in the form of a complete antibody, preferably chemically coupled Fab fragments or, more preferably, diabodies which, on the one hand, recognize CD64 and, on the other hand, are MUC1-specific according to the invention. These macrophages, which bear the bispecific recognition molecules via CD64 specificity, are re-administered to the patient in a suitable formulation in order to combat the MUC1-positive tumor. The techniques used to this end, as well as suitable methods, dosages and formulations are well-known to those skilled in the art. Another preferred embodiment involves macrophages from a patient which, following collection, are coupled with a MUC1-specific antibody or antibody fragment of the invention comprising the constant portion of an antibody which binds to macrophages via the per se known Fc receptors. The recognition molecules can bind to the macrophages either as complete antibodies, preferably chimeric or humanized IgG or IgM, or as antibody fragment, e.g. scFv, Fab or multibodies in the form of a fusion protein or chemically coupled with a portion of the constant domain of antibodies, which portion is well-known to those skilled in the art. The macrophages bearing the recognition molecules are re-administered to the patient in a suitable formulation in order to combat the MUC1-positive tumor. The techniques used to this end, as well as suitable methods, dosages and formulations are well-known to those skilled in the art.

Another preferred embodiment involves cell lines or cells from the body, such as the above-described effector cells which are transfected with molecules comprising the MUC1-specific recognition molecules of the invention and additional elements causing expression and anchoring in the membrane, e.g. transmembrane domain, and mediating activation of the effector cells upon contact with a MUC1-bearing tumor cell. The appropriate elements are well-known to those skilled in the art. For example, a dendritic cell line is transfected with a vector comprising a recognition molecule which comprises an inventive scFv or multibody and a transmembrane domain and an activating domain. In another example, macrophages are virally transfected to this end. The effector cells bearing the recognition molecules are re-administered to the patient in a suitable formulation in order to combat the MUC1-positive tumor. The techniques used to this end, as well as suitable methods, dosages and formulations are well-known to those skilled in the art.

The invention also relates to nucleic acid molecules comprising one or more genetic sequences which encode at least one of the above-described recognition molecules and/or constructs according to the invention. Owing to the degenerate genetic code, said nucleic acid molecules may have highly varying sequences. The selection of the codon also depends on the cell used to produce the recognition molecules, because different codons frequently are preferred in different cells from different organisms, and there may be a strong influence on the expression rate; for example, the arginine codons AGA and AGG preferably utilized in eukaryotic genes are rarely seen in bacteria where the codons CGC and CGU are clearly more frequent. In preferred embodiments the nucleic acid molecule of the invention is a genomic DNA, a cDNA and/or an RNA. The criteria of selecting suitable codons and the production of a suitable nucleic acid molecule are well-known to those skilled in the art.

Furthermore, the invention relates to vectors for the expression of recognition molecules, specifically in cells. In the meaning of the invention, a vector is understood to be a nucleic acid molecule according to the invention, which serves to express the recognition molecule and comprises a nucleic acid sequence which includes one or more genetic sequences encoding at least one of the above-described recognition molecules and which, in particular, includes at least one promoter effecting expression of the recognition molecule. Of course, vectors may comprise additional elements well-known to those skilled in the art, which are used e.g. in the propagation of vectors for the production in suitable cells and in cloning. The nucleic acid sequences can be present on one or more vectors; in a preferred embodiment, for example, the heavy chain of an immunoglobulin of the invention is encoded by one and the light chain by another vector. In another preferred embodiment of the invention the variable domain of the light chain and the variable domain of the heavy chain are encoded as fusion protein on the same vector under one promoter. Furthermore, in the meaning of the invention, nucleic acid sequences encoding portions of a recognition molecule can be expressed by different promoters well-known to those skilled in the art. In another embodiment, said different nucleic acid sequences can be present on one common vector. Each sequence can be expressed by its own—same or different—promoter, or the sequences can be present in a bicistronic vector under a promoter. In a preferred fashion, different expression rates of the components of recognition molecules are achieved by said different promoters, improving formation of the overall recognition molecule as compared to equal expression rate of different components. It is also preferred to use promoters which can be induced so as to improve expression of the recognition molecule. In a particularly preferred fashion the vectors also comprise the regulatory elements well-known to those skilled in the art, e.g. enhancers increasing expression of the recognition molecule or components thereof, e.g. the CMV enhancer or immunoglobulin enhancer sequences. The nucleic acid molecules and vectors preferably comprise additional nucleic acid sequences which are used as signal sequences for the secretion of recognition molecules or components thereof and are per se known to those skilled in the art, e.g. PelB, OmpA or MalE for prokaryotic cell systems, or the signal peptide of the T cell receptor, of immunoglobulin chains, oft-PA or EPO for eukaryotic cell systems [Boel et al., 2000; Herrera et al., 2000]. In an advantageous fashion, this facilitates the purification and/or improves the yield of recognition molecules. The methods for the production of the above-described nucleic acids and vectors, suitable promoters, enhancers and vector constructs, as well as the criteria for the selection thereof are well-known to those skilled in the art and will be explained in detail in the examples.

In a specific embodiment of the invention the vector according to the invention also comprises nucleic acid sequences encoding viral proteins. The virus itself will be referred to as one particular form of a vector, the genetic material of which comprises a nucleic acid sequence encoding a recognition molecule according to the invention. In a preferred form the recognition molecule is a fusion protein with a virus coat protein or components thereof, making it possible that not only the genetic material comprises the nucleic acid sequence of the recognition molecule, but also that the recognition molecule itself is present on the surface of the virus in a binding-active state, e.g. an scFv recognition molecule of the invention as a fusion protein with a coat protein of adenoviruses, poxviruses or vaccinia viruses suitable for gene-therapeutic uses. This mediates addressing the virus to a MUC1-expressing tumor cell, so that expression of the recognition molecule in the tumor cell takes place. This can be utilized in the expression of the recognition molecule in vivo in the organism or in vitro in a cell culture. In a preferred fashion, well-known systems are employed which use a helper virus for replication so as to ensure the safety of a gene-therapeutic method comprising said vector. Methods for the production of the above-described viral vectors, for the infection and expression of recognition molecules are well-known to those skilled in the art.

In another specific embodiment the vector of the invention comprises a fusion protein of a recognition molecule according to the invention and a protein or peptide specifically binding to a virus. Advantageously, the recognition molecules obtained can be used to address the virus to a MUC1-expressing cell. Thus, for example, transfer of the genetic material can be mediated via infections, thereby allowing expression of specific molecules—encoded by the genetic material of the virus—in cells in vivo in the organism in the form of a gene therapy or in vitro in a cell culture.

Furthermore, the invention relates to a method of obtaining said recognition molecules, comprising the incorporation of one or more vectors of the invention, which include one or more nucleic acid molecules of the invention, in a suitable host cell, culturing said host cell under suitable conditions, and providing one or more recognition molecules from the cells or from the culture medium. In the meaning of the invention, the term "incorporation of vectors" is understood to represent technologies per se known to those skilled in the art, by means of which said vector is introduced in a host cell, e.g. electroporation, transfection using cationic lipids, or infection, remaining therein in a transient or stable fashion. In the meaning of the invention, the term "providing one or more recognition molecules" is understood to represent technologies per se known to those skilled in the art, by means of which the recognition molecules expressed during the culturing process are obtained from the culture supernatant and/or from the cells, e.g. various protein-chemical purification steps, e.g. fractionating, concentrating, precipitating and/or chromatography. The techniques and procedures to be used in this method are well-known to those skilled in the art, and a person skilled in the art will also be able to select suitable host cells and culturing conditions, as well as methods for the provision from cells and/or culture supernatants. For example, as set forth above, a person skilled in the art will select nucleic acid sequences with suitable codons and promoter sequences adapted to the host cell so as to obtain highest possible expression of active recognition molecules. In a preferred embodiment a person skilled in the art will use e.g. affinity-chromatographic steps, e.g. chromatography on protein A or protein G or protein L, or e.g. metal ion affinity chromatography via an additionally introduced His-tag. This will be illustrated in more detail in the examples.

Apart from the steps explicitly mentioned above, the term "obtaining" also comprises additional steps such as pretreatment of the starting material or further treatments of the final product. Pretreatment procedures are per se known to those skilled in the art. In addition to the provision procedures described above, procedures of further treatment also comprise e.g. final composing and/or formulating the recognition molecule obtained by means of the production procedure into suitable forms of use and/or administration. The type of said forms of use and/or administration, e.g. solution, lyophilizate or tablet, will depend on the intended application. It is well-known to those skilled in the art which administration form is suitable for which purpose. Depending on the administration form, the recognition molecule produced using the method according to the invention can be present together with auxiliary agents, carriers or other active substances. Auxiliary agents are preferably adjuvants, other active substances, preferably immunostimulatory molecules such as interleukins. The recognition molecule produced using the method of the invention can also be chemically modified in further treatment steps. Preferably, the recognition molecule is suitably linked with one or more additional molecules, i.e. by chemical or physical interaction. As additional molecules in the meaning of the invention, other proteins or peptides are preferably used, which are covalently or non-covalently linked with the recognition molecule produced by means of the method according to the invention, e.g. in order to produce bispecific recognition molecules by linking a recognition molecule of the invention which specifically recognizes the MUC1 antigen with a second molecule which e.g. specifically binds an immunoeffector cell (for example, macrophage, NK cells, dendritic cells), or e.g. a linkage with interleukins (for example, IL-2, IL-7, IL-12, IL-15), chemokines or growth factors, and by virtue of the effect of these molecules via binding of the recognition molecule of the invention, immunoeffectors are directed to the core 1-positive tumor cells, combatting and/or destroying same, for example. As described above, said additional molecules or components thereof can also be part of the recognition molecule itself, in which case they would not be linked by means of the herein-described chemical or physical methods following expression of the recognition molecule. In the meaning of the invention, "immunoeffectors" are understood to be those components of the invention capable of directly or indirectly effecting control and/or destruction of MUC1-positive tumor cells, e.g. immunoeffector cells such as macrophages, NK cells, dendritic cells, or effector molecules such as proteins or peptides of the complement system. Suitable as additional molecules within the scope of the method according to the invention are, in particular, substances developing a therapeutic or diagnostic effect, e.g. radioisotopes or toxins. These substances are linked with the recognition molecules using per se known procedures; for example, radioisotopes are either directly incorporated (for example, iodine) or bound via a covalently coupled chelating agent (for example, yttrium, indium, bismuth). The steps of the procedure of further treatment are well-known to those skilled in the art.

The cells used according to the invention to express the recognition molecules can be prokaryotic or eukaryotic cells, e.g. bacterial, yeast (preferably *S. cerevisiae* or *P. pastoris*), insect (*D. melanogaster*), plant, mammal cells (preferably hamster, mouse or human cell lines) or organisms such as transgenic animals and plants. Preferably, *E. coli* is used for expression of the recognition molecules of the invention in a prokaryotic system, and the mammal cell lines NS0, SP2/0, CHO-K, CHOdhfr-, COS-1, COS-7, HEK293, K562, Namalwa or Percy 6 for expression in a eukaryotic system.

Furthermore, the present invention relates to host cells produced using the method described above, by means of which host cells recognition molecules of the invention can be produced. Of course, the host cells can be part of a clone or represent the clone themselves. The invention also relates to organisms comprising the host cells of the invention. Techniques to be used and methods of producing such organisms are well-known to those skilled in the art.

The invention also relates to compositions for therapeutic, prophylactic or diagnostic purposes, comprising at least one recognition molecule of the invention in a suitable, especially pharmaceutically suitable form or composition. More specifically, the pharmaceutical composition comprises additional materials and substances, e.g. medical and/or pharmaceutical-technical adjuvants. In the meaning of the invention, pharmaceutical compositions used for therapeutic and prophylactic purposes, as well as pharmaceutical compositions used as in vivo diagnostic agent will be regarded as drugs. In another preferred embodiment, compositions for ex vivo diagnostics are concerned, which may contain additional materials and substances. This embodiment will be illustrated in more detail in the description of diagnostic agents.

According to the invention, "drugs or pharmaceutical compositions"—used in a synonymous fashion herein—are substances and formulations of substances intended to cure, alleviate or avoid diseases, illness, physical defects or pathological affection by application on or in the human body. According to the invention, medical adjuvants are substances used as active ingredients in the production of drugs. Pharmaceutical-technical adjuvants serve to suitably formulate the drug or pharmaceutical composition and, if required during the production process only, can even be removed thereafter, or they can be part of the pharmaceutical composition as pharmaceutically tolerable carriers. Examples of pharmaceutically tolerable carriers will be given below. Drug formulation or formulation of the pharmaceutical composition is optionally effected in combination with a pharmaceutically tolerable carrier and/or diluent. Examples of suitable pharmaceutically tolerable carriers are well-known to those skilled in the art and comprise e.g. phosphate-buffered saline, water, emulsions such as oil/water emulsions, various types of detergents, sterile solutions, and so forth. Drugs or pharmaceutical compositions comprising such carriers can be formulated by means of well-known conventional methods. These drugs or pharmaceutical compositions can be administered to an individual at a suitable dose, e.g. in a range of from 1 μm to 10 g of recognition molecules per day and patient. Doses of from 1 mg to 1 g are preferred. Preferred is administration of doses as small in number and as low as possible, preferably a single dose e.g. of a radiolabelled recognition molecule. Administration can be effected on various routes, e.g. intravenous, intraperitoneal, intrarectal, intragastrointestinal, intranodal, intramuscular, local, e.g. intratumoral, but also subcutaneous, intradermal or on the skin or via mucosa. Administration of nucleic acids can also be effected in the form of a gene therapy, e.g. by means of viral vectors described above. The kind of dosage and route of administration can be determined by the attending physician according to clinical factors. As is familiar to those skilled in the art, the kind of dosage will depend on various factors, such as size, body surface, age, sex, or general health condition of the patient, but also on the particular agent being administered, the time period and type of administration, and on other medications possibly administered in parallel.

A "vaccine composition" is a pharmaceutical composition for the prophylactic or therapeutic active immunization of patients, so as to provoke a specific immune response against the glycosylated MUC1 tumor epitope in the patient via the immunologic network.

More specifically, the pharmaceutical compositions or drugs comprise a pharmacological substance which includes one or more recognition molecules of the invention or/and nucleic acid molecules encoding same, in a suitable solution or administration form. Administration thereof can be effected either alone or together with appropriate adjuvants described in connection with drugs or pharmaceutical compositions, or in combination with one or more adjuvants, e.g. QS-21, GPI-0100 or other saponines, water-oil emulsions such as Montanide adjuvants, polylysine, polyarginine compounds, DNA compounds such as CpG, Detox, bacterial vaccines such as typhoid vaccines or BCG vaccines, salts such as calcium phosphates, and/or other suitable materials enhancing the effect, preferably immunostimulatory molecules such as interleukins, e.g. IL-2, IL-12, IL-4 and/or growth factors such as GM-CSF. They are mixed with the recognition molecules of the invention according to well-known methods and administered in suitable formulations and dosages. Formulations, dosages and suitable components are well-known to those skilled in the art.

Obviously, the pharmaceutical composition or drug can also be a combination of two or more of the inventive pharmaceutical compositions or drugs, as well as a combination with other drugs, tumor vaccines or tumor treatments, such as antibody therapies, chemotherapies or radiotherapies, suitably administered or applied at the same time or separately in time. The production of the drugs or pharmaceutical compositions proceeds according to per se known methods.

The drugs or pharmaceutical compositions are used in the prophylaxis or treatment of tumor diseases and/or metastases, especially in the treatment of MUC1-positive tumor diseases and metastases, such as mammary carcinomas, gastrointestinal tumors, including colon carcinomas, stomach carcinomas, large intestine cancer and small intestine cancer, pancreas carcinomas, ovarian carcinomas, liver carcinomas, lung cancer, renal cell carcinomas, multiple myeloma. For example, the treatment is directed against primary tumors, minimal residual tumor diseases, relapses and/or metastases. The treatment of the tumors can also be effected as an adjuvant treatment. The drugs can also be used in the prophylaxis of MUC1-positive tumor diseases. For example, prophylactic use is directed to the prophylaxis of tumors and metastases. The tumor agents are administered in a suitable form according to well-known methods. A preferred variant is injection or administration of the drugs intravenously, locally in body cavities, e.g. intraperitoneal, intrarectal, intragastrointestinal routes, locally, e.g. directly in a tumor, in organs or lymphatic vessels (intranodal), but also subcutaneously, intradermally or on the skin, and intramuscularly. In a preferred fashion, types of administration can also be combined, in which case administration can be effected on different days of treatment or on one day of treatment. According to the invention, it is also possible to combine two or more of the inventive drugs or pharmaceutical compositions or one or more drugs of the invention with one or more drugs or tumor treatments, such as antibody therapies, chemotherapies or radiotherapies, suitably administered or applied at the same time or separately in time. Suitable formulations, dosages and combinations of components are well-known to those skilled in the art or can be determined according to well-known methods.

The present invention also relates to a method for the production of a drug or a pharmaceutical composition, comprising the steps of producing recognition molecules and further comprising the step of formulating the recognition molecules of the invention into a pharmaceutically tolerable form. The inventive recognition molecules preferred to this end are described above as embodiments of the treatment of tumor diseases and prophylaxis, as well as under in vivo diagnostic agents below.

Hence, the recognition molecules of the invention and the substances and compositions produced using the method according to the invention can preferably be used in prophylaxis, diagnosis, follow-up and/or treatment of tumor diseases. Furthermore, it is preferred to use the recognition molecules, vectors and/or the drug or pharmaceutical composition in the prophylaxis and/or treatment of cancer diseases, including tumors and metastases.

In a preferred embodiment the cancerous disease or tumor being treated or prophylactically prevented, or whose reappearance is prevented, is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatases, immunosuppression-related malignancies and/or tumor metastases.

More specifically, the tumors may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, choriomblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Ley-dig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phylloides; hemangiosarcoma; lymphangiosarcoma; myxosarcoma, ovarian carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

In another preferred embodiment the cancerous disease or tumor being treated or prophylactically prevented, or whose reappearance is prevented, is selected from the group of cancerous diseases or tumor diseases comprising cells including the MUC1 in the definition according to the invention, selected from the group of: tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs, comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarian carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, Hodgkin's disease, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancies such as Kaposi sarcoma, AIDS-associated lymphomas, AIDS-associated lymphomas of the central nervous system, AIDS-associated Hodgkin disease, and AIDS-associated anogenital tumors, transplantation-related malignancy, metastasized tumors comprising brain metastases, lung metastases, liver metastases, bone metastases, pleural and pericardial metastases, and malignant ascites.

In another preferred embodiment the cancerous disease or tumor being treated or prophylactically prevented, or whose reappearance is prevented, is selected from the group comprising cancerous diseases or tumor diseases such as mammary carcinomas, gastrointestinal tumors, including colon carcinomas, stomach carcinomas, large intestine cancer and small intestine cancer, pancreas carcinomas, ovarian carcinomas, liver carcinomas, lung cancer, renal cell carcinomas, multiple myelomas.

In another preferred embodiment the recognition molecules according to the invention are used in the prophylaxis of mammary or ovarian carcinomas in females having an increased risk of breast cancer.

In another preferred embodiment the cancerous disease or tumor or metastasization being treated or prophylactically prevented, or whose reappearance is prevented, is specifically selected from the group of gastrointestinal tumors and preferably colon carcinomas, stomach carcinomas and rectal carcinomas.

The recognition molecules of the invention can be directly employed in the treatment or prophylaxis of tumor diseases or coupled with additional effector structures. According to the invention, "effector structures" are understood to be chemical or biochemical compounds, molecules or atoms which directly or indirectly cause destruction or damage, including e.g. growth reduction or growth inhibition, of tumor cells. For example, these include radioisotopes, toxins, cytostatic agents and other effector molecules such as cytokines and chemokines or other structures representing effectors themselves or being coupled to said effector molecules, e.g. liposomes loaded with toxins or cytostatic agents, which bear the recognition molecules according to the invention. In the latter example of liposomes, particularly those effector structures are concerned which, in addition to the recognition molecule for tumor specificity, bear molecules responsible for reception of effector structures or components thereof in cells, such as antibodies against receptors causing receptor-mediated endocytosis. In such cases, the recognition molecules preferably comprise a transmembrane domain allowing their insertion in the liposomal membrane, or, in another preferred embodiment the recognition molecules are chemically coupled on the liposome surface. The techniques used to this end are well-known to those skilled in the art, including production of the liposomes. Linking of the recognition molecules with other effector structures also proceeds according to per se known methods. As already set forth above, linking can be effected e.g. directly by covalent or non-covalent loading, by chemical coupling, which may require an additional chemical or biological molecule, e.g. a chelating agent or linker, or in the form of fusion proteins or peptides via fusion. The recognition molecules are employed in the treatment of tumor diseases with MUC1-bearing tumors or in prophylaxis which, for example, prevents formation of primary tumors or metastases. One preferred objective is treatment of minimal residual disease and of metastases. The recognition molecules according to the invention are administered in a suitable formulation, in one go or repeatedly, at suitable intervals and with suitable doses.

In a preferred embodiment the above-described radioactive recognition molecules according to the invention are combined with an application of non-labelled MUC1-specific recognition molecules according to the invention. This helps towards an improvement of the background and more specific binding to the tumor by saturating small amounts of MUC1-bearing molecules in the blood. To this end, IgG molecules and more preferably IgM-derived recognition molecules are preferably used, e.g. a cIgMG or a humanized form thereof, because they primarily bind to MUC1 antigen in blood, thereby reducing the background and serum radioactivity load and increasing the relative tumor targeting, while limiting penetration into tissues and tumors by virtue of the size of the molecules. The procedures and technologies used to this end are well-known to those skilled in the art, and a person skilled in the art will also be able to devise a suitable dose, formulations, route of application, and time of administering said non-labelled recognition molecules.

Also preferred is the use of viral vectors in gene-therapeutic applications wherein specifically the surface of the viruses bears recognition molecules according to the invention.

The present invention also relates to methods of producing a diagnostic agent, comprising the steps of the inventive method for the production of MUC1-specific recognition molecules according to the invention and, in addition, comprising the step of formulating the recognition molecules in a diagnostically usable form.

According to the invention, the term "diagnostic agent" defines substances and preparations of substances intended to recognize diseases, illness, physical defects or pathological affection by application on or in the human body. Preferably, parts of the human body are understood to be body fluids such as blood, blood serum, lymph, urine, spinal fluid, or sperm, or tissue biopsies or samples.

Formulating the diagnostic agent preferably comprises modification of the produced recognition molecules with substances allowing detection of the MUC1 antigen. Suitable substances are well-known in the art. Based on the selection of a substance, a person skilled in the art will be able to take suitable measures in order to formulate a diagnostic agent.

According to the invention, it is also possible for diagnostic purposes to couple substances to the recognition molecules according to per se known methods, which facilitate detection of MUC1 antigens and/or carrier cells thereof, e.g. by biotinylation, fluorescence labelling, radioactive labelling or enzyme linking of recognition molecules.

Another method of tumor diagnostics and prognosis uses recognition molecules of the invention which recognize MUC1 antigens in the serum of humans. Also, against the background of the recognition molecules' property of binding much less MUC1 in serum compared to the well-known antibodies HMFG-1 and DF-3 (CA15-3 test), this is possible and advantageous because the recognition molecules according to the invention are capable of distinguishing clearly between normal serum and tumor serum, even in those cases where binding in serum of colon carcinoma patients is low. Determination is preferably qualitative, quantitative and/or in time-dependent relative quantities according to per se known methods. According to the invention, the same methods are also used in the follow-up of tumor diseases and to control the course of treatment, including monitoring of immune responses, and for control and dosage of tumor treatments. The techniques used in such methods are per se well-known, e.g. ELISA, Western blot, FACS (fluorescence-activated cell sorting), MACS (magnetic-activated cell sorting), ADCC (antibody-dependent cell cytotoxicity), CDC (complement-dependent cytotoxicity), immunocytochemistry and immunohistochemistry.

The preferred inventive methods of tumor diagnostics and prognosis use MUC1-specific recognition molecules of the invention in per se well-known methods to detect the glycosylated MUC1 tumor epitope antigen in serum or in tissue preparations. In these methods, MUC1 antigen, MUC1 present in immune complexes and/or MUC1 bound on cells is detected, and the presence of the MUC1 antigen is determined qualitatively, quantitatively and/or in relative quantities according to per se known methods. According to the invention, the same methods are employed in the follow-up of tumor diseases and to control the course of treatments. The techniques used in such methods are per se well-known, e.g. ELISA, Western blot, FACS (fluorescence-activated cell sorting), MACS (magnetic-activated cell sorting), ADCC (antibody-dependent cell cytotoxicity), CDC (complement-dependent cytotoxicity), immunocytochemistry and immunohistochemistry.

One preferred embodiment is a tissue rapid test wherein the tissue samples are stained with fluorescence-labelled recognition molecules of the invention in a immunohistological method. In another preferred method the recognition molecule according to the invention, preferably an isotype IgG antibody, is combined with another antibody specifically recognizing the core 1 antigen, preferably isotype IgM. The advantage is that, e.g. in gastrointestinal carcinoma diagnostics (e.g. colorectal carcinomas and stomach carcinomas), recognition at an early stage and, at the same time, prognosis with respect to the course of disease and/or risk of liver metastasization is possible, higher levels of core 1 and MUC1 antigen indicating a more unfavorable prognosis as to the course, and higher levels of core 1 indicating a probability of liver metastasization increased by several times. In another preferred embodiment the antibodies and recognition molecules are directly labelled with various fluorescent dyes, e.g. Cy3 and Cy5 or Cy3 and FITC. In one embodiment, wherein signal intensification is advantageous, the antibodies and/or recognition molecules are enhanced by labelled secondary antibodies or biotin-streptavidin. Advantageously, different isotypes and/or sequences of species in the constant region of antibodies are used. The techniques and methods used to this end, e.g. of labelling and immunohistology, as well as the selection of suitable formats of recognition molecules are well-known to those skilled in the art. The diagnostic method described above is not restricted to gastrointestinal tumors, but can be used in any tumor disease involving the MUC1 antigen.

For a serological tumor test, another preferred embodiment of the invention combines the determination of MUC1, as described above, with the determination of other serological tumor markers, e.g. PSA, CEA or AFP. One embodiment preferred in this case is determination of MUC1 and core 1 antigen. In a preferred embodiment, MUC1 is immobilized from the serum on a solid phase, using an MUC1-specific antibody, and detected with a recognition molecule of the invention as detection antibody, which specifically binds the glycosylated MUC1 tumor epitope, and the core 1 antigen is detected on MUC1 immobilized by means of an anti-MUC1 scavenger antibody, such as the MUC1-specific recognition molecules of the invention, using a specific anti-core 1 antibody. This diagnostic test combines early recognition with a prognostic statement as to the course of disease and/or the probability of liver metastasization. The techniques used to this end, e.g. labelling and serology, including the detection methods, are well-known to those skilled in the art. The diagnostic methods described above are not restricted to gastrointestinal tumors, but can be used in any tumor bearing the MUC1 antigen. The serological tests described above are used in diagnosis, monitoring the course of a tumor disease, and in the prognosis of MUC1-positive tumors.

In another method according to the invention, the MUC1-specific recognition molecules of the invention are used in in vivo diagnostics. To this end, the recognition molecules are labelled using suitable, per se known methods and thus made available for per se known imaging methods in humans, e.g. radioimmunodiagnostics, PET scanning methods or immunofluorescence endoscopy, e.g. by coupling and/or loading with appropriate molecules, e.g. radioactive isotopes such as indium, or fluorescent dyes such as Cy3, Cy2, Cy5 or FITC. In a preferred embodiment, multibodies according to the invention are covalently coupled with a suitable chelating agent (for example, DOTA or DTPA) and, loaded with indium-111, used in in vivo diagnostics. In a preferred embodiment, they are administered intravenously at a dose appropriate to the individual, and the location of the MUC1 antigen and of a potential tumor is measured according to per se known methods. The methods and technologies used to this end, including imaging methods, are well-known to those skilled in the art, and a person skilled in the art will also be able to devise a suitable dose and formulations.

In another preferred embodiment, immunoglobulins, preferably IgG, are radiolabelled as described above and illustrated in more detail in the examples, e.g. with indium-111, and administered locally into the tumor or blood vessels supplying or evacuating the tumor. In one embodiment, this is used to determine the size of the tumor, and in another embodiment, to determine affected lymphatic nodes. The methods and technologies used to this end are well-known to those skilled in the art, and a person skilled in the art will also be able to devise a suitable dose and formulations.

In another embodiment the radioactively labelled recognition molecules of the invention are also administered via other routes of application. Preferred routes are intraperitoneal, intranodal or intrarectal and intragastrointestinal, respectively. Intraperitoneal is particularly advantageous in the determination of tumors accessible through the peritoneum and/or metastasizing therein, e.g. ovarian carcinomas and certain gastrointestinal carcinomas. Intrarectal or intragastrointestinal administration is advantageous in some gastrointestinal tumors and in localization and size determination thereof. In some cases, intranodal can be used for direct infiltration of single lymphatic nodes.

In a preferred embodiment the above-described radioactive recognition molecules of the invention are combined with an application of non-labelled MUC1-specific recognition molecules of the invention for in vivo diagnostic agents. This is to improve the background. The methods and technologies used to this end are well-known to those skilled in the art, and a person skilled in the art will also be able to devise a suitable dose, formulations, route of application, and time of administering said non-labelled recognition molecules.

In another preferred embodiment, recognition molecules of the invention, preferably immunoglobulins, multibodies or antibody fragments, more preferably IgG, Fab and multibodies, are labelled with a fluorescent dye and administered in vivo. Preferred routes of application are intrarectal, intragastrointestinal, intraperitoneal, intravenous and into supplying or evacuating blood vessels. A particularly preferred embodiment is used to localize gastrointestinal carcinomas by means of fluorescence endoscopy following application of fluorescence-labelled recognition molecules. In another preferred embodiment a recognition molecule of the invention is combined with at least one antibody to another tumor antigen, preferably anti-core 1 antibody. In a preferred fashion, different fluorescent dyes are used, allowing differentiation of the recognition molecules and antibodies, thereby combining a prognostic statement with early recognition and a greater number of cases. Preferred fluorescent dyes are those having lower background fluorescence, which are well-known to those skilled in the art. The methods and technologies used to this end, including imaging methods, e.g. fluorescence endoscopy, are well-known to those skilled in the art, and a person skilled in the art will also be able to devise a suitable dose, formulations, route of application, and time of administering said non-labelled recognition molecules.

The invention has several advantages: The MUC1-specific recognition molecules of the invention recognize the types of carcinomas in a specific fashion, which is why they can be used with advantage in diagnosis and/or therapy of a large number of tumor patients with different indication. Moreover, the recognition molecules advantageously bind to a very low extent in areas in normal tissue inaccessible in vivo. Compared to well-known tumor markers, this is a particular advantage and an outstanding property of the recognition molecules according to the invention. One particular advantage of the recognition molecules of the invention is their high specificity for tumor tissue. In particular, this is due to the high specificity for a defined glycosylated MUC1 tumor epitope. The polymorphic epithelial mucin MUC1, in the form of the overall molecule, is a well-established tumor marker. As a result of the complexity of the molecule, which is very large, highly glycosylated, essentially consists of a large number of polymorphic tandem repeats of 20 amino acid residues in the extracellular state, and has heterogeneous glycosylation with respect to the tandem repeats, MUC1 has a variety of epitopes. The recognition molecules of the invention binding the glycosylated MUC1 tumor epitope specifically in the meaning of the invention detect a defined epitope in MUC1, resulting in high specificity of the recognition molecules for tumor tissue. Furthermore, one particular advantage is that the recognition molecules of the invention have low levels of recognition of such MUC1 released into the serum by tumor cells (shedding). Such reduced binding to MUC1 present in the serum in a tumor patient is a great advantage in the therapy of tumor diseases using the recognition molecules according to the invention. Furthermore, the recognition molecules of the invention exhibit high affinity. In particular, this presents a way of constructing lower-valent fragments such as scFv and multibodies. The option of having these different formats available is advantageous in the development of therapeutic agents.

Without intending to be limiting, the invention will be explained in more detail with reference to the examples.

EXAMPLES

1. Preparation of scFv with Varying Linker Lengths, which Specifically Recognize the Glycosylated MUC1 Tumor Epitope MUC1-specific scFv with the sequences SEQ ID Nos. 36 to 59 were produced by PCR amplification and subsequent cloning of the variable chains into a bacterial expression vector. This vector includes the lacZ promoter, a ribosome binding site (RBS), the M13 origin, the pelB signal sequence for secretion into the periplasm, an ampicillin resistance gene, and a cloning cassette to couple a hexahistidine tag for efficient purification and a c-myc-tag to the C-terminal end of the scFv (FIG. 1). For varying linker lengths, $V_H$ and $V_L$ were amplified with specific primers in such a way that 22 nucleotides at the 3' end of $V_H$ and at the 5' end of $V_L$ formed a complementary region (FIG. 2, PCR I and PCR II), Subsequently, following purification, the two PCR fragments were linked in an SOE-PCR (FIG. 2, PCR III), and the PCR fragment was cloned into the above-described vector via NcoI/NotI.

2. Bacterial Expression and Purification of scFv Specifically Recognizing the Glycosylated MUC1 Tumor Epitope The antibody fragments from Example 1 were expressed in *Escherichia coli* and purified. To this end, the corresponding plasmid was transformed in electrocompetent *E. coli* by means of electroporation and cultured in 2×TY medium (10 g of yeast extract, 16 g of tryptone, 5 g of NaCl per liter) with 100 µg/ml ampicillin overnight. This culture was diluted 1:100 with 2×TY medium added with 100 µg/ml ampicillin and 0.5% glucose and incubated at 37° C. until an $OD_{600\ nm}$ of about 0.6 was reached. Thereafter, the culture was added with 1 mM IPTG for induction and incubated at 25° C. for another 5 hours. The bacteria were harvested by centrifugation at 4000×g for 20 min, the cell pellet was resuspended in TES buffer (30 mM Tris-HCl, pH 8.0, 20% saccharose, 1 mM EDTA) and incubated on ice for 20 min.

Subsequently, 5 mM MgSO4 was added, and the suspension was incubated on ice for another 20 min. The periplasm fraction was obtained by centrifugation at 4000×g for 60 min and dialyzed against binding buffer (50 mM phosphate buffer, pH 8.0, 300 mM NaCl, 10 mM imidazole) at 4° C. overnight. The antibody fragments contained in the periplasm fraction were purified by metal ion affinity chromatography (HiTrap Chelating HP, Amersham Pharmacia Biotech) using the C-terminal His-tag. To this end, the dialyzed fraction was loaded on a column previously equilibrated with binding buffer, and the non-binding proteins were washed from the column with washing buffer (50 mM phosphate buffer, pH 8.0, 300 mM NaCl, 30 mM imidazole). Subsequently, the antibody fragments were eluted with elution buffer (50 mM phosphate buffer, pH 8.0, 300 mM NaCl, 300 mM imidazole).

3. Cloning of Vectors to Express Chimeric IgG and IgM Antibodies Specifically Recognizing the Glycosylated MUC1 Tumor Epitope The NcoI/XhoI DNA fragment from the scFv vector, which encodes $V_H$ (FIG. 1), was cloned into the NcoI/SalI-cut BS Leader vector (FIG. 3). The BS Leader vector includes a cloning cassette to introduce the T cell receptor signal peptide sequence at the 5' end and a splice donor sequence at the 3' end of the sequences of the variable domains (FIG. 3). The $V_L$ sequence of the corresponding antibody was amplified with specific primers to introduce the NcoI restriction site at the 5' end and the NheI restriction site at the 3' end in the PCR using the scFv sequence as template and, following NcoI/NheI digestion, cloned into the likewise digested BS Leader vector. Thereafter, each HindIII/BamHI fragment from the BS Leader vector was cloned into the corresponding eukaryotic expression vector. These vectors (pEFpuroCγIV$_H$, pEFpuroCμV$_H$ and pEFneoCκV$_L$) include EF-1α-promoter and HCMV enhancer, SV40 origin, BGH polyadenylation signal, puromycin resistance gene in the vector for the heavy chain and neomycin resistance gene in the vector for the light chain, as well as the genomic sequences of the human constant γ1 region or μ region for the heavy chain or of the human constant κ region for the light chain (primers for amplification from genomic human DNA and vector map see FIG. 3).

4. Eukaryotic Expression of Chimeric IgG and IgM Antibodies, which Specifically Recognize the Glycosylated MUC1 Tumor Epitope, in CHO Cells and Purification Thereof To express the chimeric antibodies cIgG-Panko1 consisting of the sequences SEQ ID Nos. 64 and 68, cIgG-Panko2 consisting of the sequences SEQ ID Nos. 65 and 69, cIgM-Panko1 consisting of the sequences SEQ ID Nos. 66 and 68, and cIgM-Panko2 consisting of the sequences SEQ ID NO. 67 and 69, CHOdhfr-cells (ATCC No. CRL-9096) were co-transfected with a mixture of vectors for the heavy and light chains (1:3) by means of electroporation ($10^6$ cells/ml, 500 V, 50 μs) and cultured in selection medium (CHO-S-SFM II medium (Life Technologies), HT supplement (Biochrom), 400 μg/ml G418, 5 μg/ml puromycin) for 2 weeks. Following single-cell cloning in a 96-well plate, the supernatants were tested in an ELISA (glycosylated MUC1 peptide (30mer, see below) as antigen, anti-human Fcγ1-POD-coupled or antihuman Fc5μ-POD-coupled (Dianova) as secondary antibody), and the clone with the highest antibody production rate was selected (about 0.5 μg/$10^6$ cells/24 h).

For antibody production, the stably transfected CHO cells secreting the chimeric IgG and IgM, respectively, were cultured in spinner flasks or in flask culture in CHO-S-SFM II medium, supplemented with HT supplement, until a cell density of about 1×$10^6$ cells/ml was reached. Following removal of the cells from the cell culture supernatant by centrifugation (400×g, 15 min), the chimeric antibody was purified using a protein A column (HiTrap r-protein A FF, Amersham Pharmacia Biotech) for chimeric IgG or an antihuman Fc5μ antibody affinity column for chimeric IgM. The purified antibody fraction eluted by sudden pH change was re-buffered in PBS and concentrated using Centriprep centrifuge tubes (cut-off 50 kDa, Millipore).

5. Analysis of scFv and Antibodies, which Specifically Recognize the Glycosylated MUC1 Tumor Epitope, in an ELISA Various synthetic peptides and glycopeptides were used as antigens: a non-glycosylated 30mer with the sequence APPAHGVTSAPDTRPAPGSTAPPAHGVTSA (SEQ ID NO: 70); a glycosylated 30mer with the sequence APPAH-GVTSAPDT[GalNAcα]R PAPGSTAPPAHGVTSA (SEQ ID NO: 71), a series of non-glycosylated MUC1 peptides of varying length with the sequence [VTSAPDTRPAPG-STAPPAHG]$_n$ wherein n=1 (SEQ ID NO: 72), 3 (SEQ ID NO: 73) and 5 (SEQ ID NO: 74) (TR1, TR3 and TR5), and a series of glycosylated MUC1 peptides of varying length with the sequence A[HGVTSAPDT(GalNAcα)RPAPG-STAPPA]$_n$ wherein n=1 (SEQ ID NO: 75), 3 (SEQ ID NO: 76) and 5 (SEQ ID NO: 77) (TR1g, TR3g and TR5g).

Using the respective stock solutions (1 mg in 1 ml of bidist. H$_2$O) stored in portions at −20° C., a dilution of 10 μg/ml in PBS or 10 μg/ml in bidist. H$_2$O was produced. 50 μl/well of the above was pipetted in a microtiter plate, and the test plate was incubated overnight (using NUNC—Immuno plate F96 MAXISORP and incubation at 4° C. for peptides in PBS; using Nunclon TC plates and slight drying of the peptides at 37° C. for peptides in bidist. H$_2$O). On the next day, the test plate was washed 3 times with PBS/0.2% Tween. Subsequently, non-specific binding sites were blocked with 2% BSA in PBS, and 50 μl of the first antibody was applied (murine antibodies: 10-10000 ng/ml PBS/1% BSA; chimeric IgG: 1-100 ng/ml in PBS/1% BSA; scFv: 50-500 ng/ml in PBS/1% BSA). After three wash steps with PBS/0.2% Tween, the corresponding peroxidase-coupled secondary antibodies were employed to detect the specifically bound antibody constructs (an anti-mouse or anti-human Fcγ1 for the complete antibody, an anti-His-tag antibody for scFv). To detect the bound secondary antibody, a color reaction with TMB (3,3',5,5'-tetramethylbenzidine) was performed. After 15 minutes the reaction was quenched by adding 2.5 N H$_2$SO$_4$. Measurement was performed using a microtiter plate photometer with 450 nm filter in dual mode versus 630 nm reference filter. Representative results are illustrated in FIGS. 4 to 8.

5.1. Binding to the Glycosylated PDTRP Region within an MUC1 Tandem Repeat Sequence FIG. 4 shows preferred binding of the recognition molecules of the invention to the glycosylated MUC1 peptide. Two recognition molecules with varying loop sequences in IgG format are compared. The antibody constructs mIgG- Panko1 (SEQ ID NO. 60 and SEQ ID NO. 62) and mIgG-Panko2 (SEQ ID NO. 61 and SEQ ID NO. 63) bind to the 30mer in a highly specific fashion, preferably to the glycosylated peptide, and only slightly, or not at all, to the nonglycosylated peptide sequence. In comparison to mIgG-Panko1 and mIgG-Panko2, FIG. 5 illustrates binding of the MUC1-specific antibodies HMFG-1, C595 and SM3 to the nonglycosylated and to the glycosylated 30mer (representative example). The three antibodies HMFG-1, C595 and SM3 showed no or only slight glycosylation dependence with a factor (ratio of glycosylated/non-glycosylated peptide) of <1.2 for all three antibodies. The antibodies are used for differentiation and are not part of the recognition molecules according to the invention. In contrast, a factor of >4.5 (in FIG. 5: 5.1) results for mIgG-Panko1 and a factor of >20 (in FIG. 5: 22.1) for mIgG-Panko2 under the same conditions.

FIG. 6 illustrates different formats of the recognition molecules of the invention in their preferred specific binding to the glycosylated MUC1 peptide.

5.2. Binding to Multiple Non-Glycosylated MUC1 Tandem Repeats

As a representative example, FIG. 7 shows the binding dependence of the recognition molecules of the invention, mIgG-Panko1 and mIgG-Panko2, on the number of nonglycosylated tandem repeats compared to the MUC1-specific antibodies C595 and SM3. The ratio of the signal with TR5 peptide to that with TR1 peptide represents a factor reflecting the degree of binding dependence on the number of repeats. Factors of >3 (in FIG. 7: 3.9) and >8 (in FIG. 7: 12.7), result for mIgG-Panko1 and mIgG-Panko2, respectively, whereas the MUC1-specific antibodies C595 (factor 1.1) and SM3 (factor 2.1) show no or only slight dependence under the same conditions.

5.3. Binding to Multiple Glycosylated MUC1 Tandem Repeats

As a representative example, FIG. 8 shows the binding dependence of the inventive recognition molecule mIgG-Panko2 on the number of tandem repeats (multiple glycosylated PDTR regions) compared to the MUC1-specific antibodies C595 and SM3. The mIgG-Panko2 shows additional dependence on the number of glycosylated tandem repeats, whereas binding of the MUC1-specific antibodies C595 and SM3 is independent of any increase in the number of repeats.

6. Immunohistologic and Immunocytologic Staining with Recognition Molecules Specifically Recognizing the Glycosylated MUC1 Tumor Epitope For immunohistologic staining, frozen sections of appropriate tissue samples were air-dried and fixed with 10% formaldehyde in PBS for 15 min. To reduce the endogenic peroxidase activity, the sections were treated with 3% hydrogen peroxide in PBS and, following blocking of non-specific binding sites with rabbit serum, incubated with an MUC1-specific recognition molecule in the form of a primary antibody. Subsequently, the preparations were incubated with an appropriate secondary antibody (anti-mouse IgG, POD-coupled). The staining reaction was performed using the peroxidase substrate diaminobenzidine, and counterstaining with hematoxylin.

The exemplary recognition molecule mIgM-Panko2 according to the invention undergoes reaction with only a small number of structures in normal tissue. These are mainly found in immune-privileged regions of the body, e.g. on the apical surface of cells of certain glandular ducts and are therefore located in areas inaccessible or barely accessible to an antibody in vivo (Table 3). Moreover, staining in breast normal tissue is weak compared to tumor tissue and is found on the apical membrane only.

TABLE 3

Reaction of human normal tissue with the MUC1-specific antibody mIgG-Panko2.

| Type of tissue | Reactivity |
| --- | --- |
| epidermis | |
| stratum basale | +/− |
| stratum spinosum | − |
| stratum granulosum | − |
| stratum corneum | − |
| non-epidermal cells | − |
| stomach | |
| foveola epithelium | − |
| fundus glands | − |
| corpus glands | − |
| small intestine | |
| mucosa | − |
| colon | |
| mucosa | − |
| breast | |
| glandular ducts | + |
| acini | + |
| myoepithelial cells | − |
| spleen | |
| trabeculae lienis | − |
| reticular cells | − |
| lymphocytes | − |
| macrophages | − |
| endothelium | |
| prostate | + |
| liver | |
| hepatocytes | − |
| biliary ducts | + |
| kidneys | |
| glomerules | − |
| capsular epithelium | − |
| tubuli proximalis | − |
| tubuli distalis | −/+ |
| collecting tubule | −/+ |
| lymphatic nodes | |
| lymphocytes | − |
| macrophages | − |
| reticular cells | − |
| gall bladder | |
| mucosa | + |
| brain | |
| neurons | − |
| glial cells | − |
| meninges | − |
| ependymal cells | − |
| adrenal gland | |
| adrenal cortex | − |
| adrenal medulla | − |

TABLE 3-continued

Reaction of human normal tissue with the MUC1-specific antibody mIgG-Panko2.

| Type of tissue | Reactivity |
|---|---|
| thymus | |
| epithelial reticular cells | − |
| Hassall's corpuscles | −/+ |
| lymphocytes | − |
| macrophages | − |
| bladder | |
| urothelium | + |
| heart | |
| endocardium | − |
| myocardium | − |
| mesothelium | − |
| pancreas | |
| glandular ducts | + |
| acini | + |
| islets of Langerhans | − |
| connective tissue | − |
| synovial tissue | − |
| muscle tissue | |
| smooth muscle | − |
| skeletal muscle | − |

The recognition molecules as claimed give positive reaction with a variety of tumors. The data in Table 4 show that MUC1-specific recognition molecules recognize a high percentage of tumor patients of a single indication, which differs from one indication to the other. In large intestine adenomas, staining correlates with the degree of dysplasia. Colon adenomas do not react with mIgG-Panko2 or only very slightly, whereas colon carcinomas are positive. Normal pancreas tissue is only slightly positive, whereas pancreas carcinomas show a very strong reaction with the recognition molecule mIgG-Panko2 according to the invention.

TABLE 4

Reaction of human tumor tissue with mIgG-Panko2.

| Type of tissue | % positive cases |
|---|---|
| colon | |
| adenomas | |
| tubular | 25 |
| tubular-villous | 25 |
| villous | 33 |
| transitory mucosa | 30 |
| carcinomas | |
| adenocarcinoma | 90 |
| papillary adenocarcinoma | 67 |
| mucous adenocarcinoma | 67 |
| mucin-producing adenocarcinoma | 100 |
| signet-ring cell carcinoma | 100 |
| liver metastases | 81 |
| stomach carcinomas | 90 |
| liver carcinomas | |
| well-differentiated | 14 |
| moderately differentiated | 42 |
| slightly differentiated | 50 |
| pancreas carcinomas | 100 |
| mammary carcinomas | |
| primary carcinomas | 87 |
| metastases | 91 |
| renal cell carcinomas | 100 |

Immunofluorescence was used for the immunocytologic stainings. To this end, appropriate cells were slightly dried on microscope slides and fixed with 5% formaldehyde for 10 min. Following blocking of non-specific binding sites with BSA (1% in PBS), the cells were incubated with the recognition molecules of the invention in the form of primary antibodies. This was followed by washing 3 times with PBS and incubation with the appropriate fluorescence-labelled secondary antibody (anti-mouse IgG-FITC or anti-human Fab-Cy2, Dianova). After repeated washing with PBS, the cells were embedded in Mowiol.

Various cell lines were tested with MUC1-specific recognition molecules in immunofluorescence. A number of tumor cell lines gave positive reaction (Table 5 and FIGS. 9 and 10).

TABLE 5

Reactivity of various cell lines with the MUC1-specific antibody mIgG-Panko2.

| Cell lines | Reactivity |
|---|---|
| ZR-75-1 | positive |
| T47D | positive |
| U266 | (positive) |
| LN78 | positive |
| HT29 | negative |
| HCT15 | (positive) |
| HepG2 | negative |
| K562 | positive |
| MCF-7 | positive |
| HEK293 | (positive) |

FIG. 9 exemplifies fluorescence labelling of T47D cells, a mammary carcinoma cell line, with mIgG-Panko2. FIG. 10 exemplifies fluorescence labelling of K562 cells with cIgG-Panko1.

Using immunohistology and immunofluorescence labelling, the neuraminidase dependence of the glycosylated MUC1 tumor epitope was investigated as well. To this end, sections or cells were pre-incubated with neuraminidase (0.02 U/ml PBS+0.01 M $Ca^{2+}$) for one hour at room temperature, subsequently washed with PBS and then labelled as above. As illustrated in Tables 6 and 7, binding of the recognition molecules of the invention to the glycosylated MUC1 tumor epitope is neuraminidase-independent in the meaning of the invention or is enhanced by neuraminidase treatment.

TABLE 6

Immunohistologic staining of human tissue with mIgG-Panko2 before and after neuraminidase treatment.

| | Reactivity untreated | Reactivity after neuraminidase treatment |
|---|---|---|
| normal colon tissue | − | − |
| colon adenomas | + | + |
| colon carcinomas | ++ | ++ |
| mammary carcinomas | ++ | +++ |

TABLE 7

Immunofluorescence labelling of two tumor cell lines with mIgG-Panko2 before and after neuraminidase treatment.

| | Reactivity untreated | Reactivity after neuraminidase treatment |
|---|---|---|
| K562 | + | ++ |
| ZR-75-1 | +++ | ++++ |

7. Chelating and Radioactive Labelling of Antibodies and Antibody Fragments Specifically Recognizing the Glycosylated MUC1 Tumor Epitope Using conjugation, a chelating agent allowing binding of a radioactive metal was covalently bound to the antibodies mIgG-Panko2 and cIgG-Panko1 or to the scFv formats with the sequences SEQ ID Nos. 36 and 45. Commercial products from Macrocyclics (Dallas, USA), p-isothiocyanatobenzyl-diethylenetriaminepentaacetic acid (p-SCN-Bz-DTPA) and p-isothiocyanatobenzyl-1,4,7,10-tetraazacyclododecane-1,4,7,10-tetraacetic acid (p-SCN-Bz-DOTA) were employed as chelating agents. Both chelating agents are suitable for linking to antibodies for radiolabelling thereof [Brechbiel et al., 1986; Kozak et al., 1989; Stimmel et al., 1995].

Conjugation proceeds via reaction of the isothiocyanate group in the chelating agent with a free $\epsilon$-amino group of the amino acid lysine on the antibody, thus forming a covalent N—C bond between chelating agent and antibody.

Initially, the purified antibody or the purified antibody fragment must be re-buffered in coupling buffer, pH 8.7. To this end, ultrafiltration in a filtration cartridge (CENTRIPREP YM-50 or YM-10; Millipore) was performed. This was done by repeated dilution with a 10-fold volume and filtration through a membrane of defined pore size using centrifugation. In this way, PBS was replaced by alkaline coupling buffer (0.05 M sodium carbonate, 0.15 M sodium chloride, pH 8.7).

Chelating was performed using the bifunctional chelating agents p-SCN-Bz-DTPA and p-SCN-Bz-DOTA, respectively. For the chelating reaction, the protein (1 to 10 mg/ml) in coupling buffer and a solution of chelating agent of 1 mg/ml in 2% DMSO/water were mixed such that a molar excess of chelating agent was ensured. This was followed by incubation of the mixture at 37° C. for 1 hour. Subsequently, non-bound chelating agent was removed by ultrafiltration in the same vessel (CENTRIPREP YM50 or YM-10; Millipore) and, as described above, this was re-buffered to pH 4.2 in a loading buffer (0.15 M sodium acetate, 0.15 M sodium chloride, pH 4.2) required for radioactive labelling. The protein concentration during and after this step was re-adjusted to 1-10 mg/ml using UV measurement at 280 nm.

Conditions for the chelating reaction had to be found, which would allow radiolabelling of the antibody without substantially reducing the bioactivity thereof.

The chelated antibody was loaded with a radioactive metal, thereby producing the radioantibody. The isotopes $^{111}$indium and $^{90}$yttrium were used for loading. Both have comparable chemical and physicochemical properties, being bound as trivalent ions ($^{111}$In$^{3+}$, $^{90}$Y$^{3+}$) by the chelating agent. The antibody labelled with $^{111}$indium is a γ-emitter and is used clinically to find the individual dose for a patient, while $^{90}$yttrium is a β-emitter which is used therapeutically. The half-lives are 67 hours for $^{111}$In and 64 hours for $^{90}$Y. $^{111}$Indium chloride from the company NEN (Perkin Elmer, Belgium) was used for loading. The radioactive metal is supplied in a solution of hydrochloric acid. First of all, the $^{111}$InCl$_3$ solution was brought to an HCl concentration of 1 M. Subsequently, this was diluted with 0.05 M HCl to a specific activity of 80-320 mCi/ml, and an aliquot thereof was used for incorporation in the chelated antibody, in which case the added volume of HCl-acidic $^{111}$InCl$_3$ solution should be equal to the volume of antibody solution supplied in the coupling buffer of pH 4.2 so as to ensure pH stability. The incubation time was 1 hour at 37° C., with occasional careful mixing.

Subsequently, the filter insert was re-inserted into the filtration cartridge and re-buffered as described above in phosphate buffer, pH 7.2, including a physiological content of sodium chloride, thereby effecting separation of high-molecular weight radiolabelled antibody and unbound $^{111}$InCl$_3$. Quantification of $^{111}$In incorporation in the chelated antibody was performed using thin layer chromatography. The incorporation rate of radioactive metal was 80-99% of the radioactivity employed.

8. Cell Binding Tests and Scatchard Analysis of Radio-Labelled Recognition Molecules Specifically Recognizing the Glycosylated MUC1 Tumor Epitope Various tumor cell lines were used to test the binding capability of radiolabelled recognition molecules. In each double determination, a defined number of cells were placed in a 1.5 ml vessel and incubated with increasing amounts of antibodies. Following washing, the amount of bound antibodies was determined on the basis of the counting rate. This value was plotted in a diagram as ratio of bound/non-bound versus bound amount, the slope in the linear region of the curve was determined, and the abscissa intersection was determined (Scatchard analysis, see below). $1 \times 10^6$ cells per batch are required. Following pre-incubation of the cells for one hour on ice, the required amount of cells was placed in reaction vessels, centrifuged (5 min at 1000×g, 25° C.), and the supernatant was removed. Thereafter, this was filled up with PBS/0.1% Tween20/1% BSA to make a volume of 200 µl, subtracting the amount of recognition molecules to be added later. Subsequently, the corresponding recognition molecule was added to make a final volume of 200 µl (about 40 to 500 ng, depending on the recognition molecule), and the batches were incubated for one hour at 4-8° C. Following centrifugation (4 min, 1000×g, 25° C.), the supernatant was removed and the cell pellet carefully resuspended in 500 µl of PBST/1% BSA. After another wash, the cell pellet was measured in the vessel on a gamma counter. The specific counting rates were determined in the initial solutions of defined concentration, and the value in cpm/ng was used as a basis of relativizing the measured values of bound antibody. The abscissa values are plotted as bound molecules of antibody per cell (r). The respective ordinate value is the quotient of binding (r) and free binding, with free binding representing the difference of total amount and amount of bound antibody (values in M in FIG. 12). The abscissa intersection indicates the number of binding sites/cell. The slope of the straight line furnishes the association constant $K_{ass}$ in $M^{-1}$.

FIG. 11 exemplifies the Scatchard analyses of binding of radiolabelled recognition molecules in scFv format with the sequence SEQ ID NO. 36 (monovalent scFv, FIG. 11a) and 45 (multibody, FIG. 11b) on T47D cells, a $K_{ass}$ of $4.5 \times 10^6$ $M^{-1}$ and $5.3 \times 10^6$ binding sites/cell for the monovalent scFv and a $K_{ass}$ of $1.9\times10^7$ $M^{-1}$ and $2.6\times10^6$ binding sites/cell for the multibody being obtained under these conditions.

In Table 8, the association constants and the number of cell binding sites of various antibodies and antibody formats on K562 cells are summarized and compared with HMFG-1 used and tested under the same conditions.

TABLE 8

Cell binding test and Scatchard analysis with radiolabelled recognition molecules on K562 cells.

| Antibody | $K_{ass}$ [M−1] | Number of binding sites/cell |
|---|---|---|
| mIgG-Panko2 | $9.5 \times 10^8$ | $1.0 \times 10^5$ |
| HMFG-1 | $2.7 \times 10^8$ | $6.3 \times 10^4$ |
| cIgG-Panko1 | $1.2 \times 10^8$ | $1.9 \times 10^5$ |
| cIgG-Panko2 | $6.1 \times 10^8$ | $1.1 \times 10^5$ |
| SEQ ID NO. 36 | $1.8 \times 10^7$ | $5.5 \times 10^5$ |
| SEQ ID NO. 46 | $4.9 \times 10^7$ | $4.8 \times 10^5$ |

9. Biodistribution of Radiolabelled Recognition Molecules, which Specifically Recognize the Glycosylated MUC1 Tumor Epitope, in an In Vivo Tumor Model As tumor model, human colon carcinoma tissue (xenograft #5841) was transplanted subcutaneously on nude mice (Ncr: nu/nu, female). $10^7$ MUC1-positive ZR-75-1 breast cancer cells as another tumor model were injected subcutaneously in nude mice (Ncr: nu/nu, female). After about 3-4 weeks, the tumor is palpable under the skin. To each tumor-bearing mouse (n=5 per point in time) 5 µg—of $^{111}$In-labelled mIgG-Panko2 in 200 µl was administered into the tail vein. The mice were sacrificed after 5 min, 1 h, 4 h, 8 h, 24 h, 48 h and 72 h, and the radioactivity distribution in the tumor, in serum and in organs was determined. FIG. 12 illustrates the specific accumulation of mIgG-Panko2 in the tumor in % ID/g tumor (relative to injected dose and tumor weight) in a tissue transplant model. In contrast, there is a depletion of radioactivity in the organs and in serum over the time profile as indicated. FIG. 13 summarizes the results with the ZR-75-1 model. The specific uptake of radiolabelled mIgG-Panko2 in the tumor reaches more than 85% ID/g tumor after 72 hours, with accumulation in organs and serum being very low and comparable with healthy mice.

10. Detection of Tumor-Specific Secretory MUC1 in a Sandwich ELISA Using Recognition Molecules Specifically Recognizing the Glycosylated MUC1 Tumor Epitope Tumor-specific secretory MUC1 can be detected in a sandwich ELISA. A MUC1-specific antibody was used as scavenger antibody of MUC1, and a recognition molecule of the invention was used to detect the tumor-specific MUC1. To detect core 1-positive secretory MUC1, a recognition molecule according to the invention is used as scavenger, for example, and a core 1-specific antibody is used to detect the core 1 antigen. A third enzyme- or fluorescence-coupled antibody must be used to detect the secondary antibody.

The supernatants of three tumor cell lines (K562, ZR-75-1 and T47D) were analyzed as examples. The results are illustrated in Table 9. $10^5$ cells per ml of cell culture medium were seeded, cultured for 4 days without replacing the medium, an aliquot was subsequently drawn, and the cell culture supernatant was separated from the cell pellet by centrifugation. 50 µl of undiluted supernatants were used in the ELISA. The sandwich ELISA was carried out by coating the microtiter plate with scavenger antibody (HMFG-1 or mIgG-Panko2, 1 µg/ml) in PBS at 4° C. overnight. Three different concentrations of antibody were used for coating (1 µg/ml, 2 µg/ml and 4 µg/ml). The 1 µg/ml coating was found to be the most sensitive in the sandwich ELISA. Subsequently, the coated plates were washed twice with PBS and blocked in 5% BSA, 0.05% Tween 20 in PBS for 1.5 hours at room temperature. The blocking buffer was removed, the plates were washed once more with 0.1% Tween 20 in PBS (washing buffer), the samples were added and incubated at room temperature for 1.5 hours. Cell culture medium or 2% BSA in washing buffer (dilution buffer for secondary antibody) was used as negative control. Positive control was not available. For a MUC1-core 1 sandwich ELISA, neuraminidase treatment was performed—after washing three times in the wells intended for that purpose. To this end, a neuraminidase solution (DADE Behring, Germany) was diluted 1:5 in imidazole buffer (0.68 g of imidazole, 0.19 g of $CaCl_2$ and 0.4 g of NaCl in 100 ml of $H_2O$, pH 6.8) and incubated at 50 µl/well for 30 min at 37° C. As a control, the imidazole buffer with no neuraminidase solution was incubated in a corresponding well. Subsequently, the wells were washed three times, and the biotinylated mIgG-Panko2 (EZLink sulfo-NHS-LC-biotin, Pierce) or an anti-core 1 antibody (mIgM-Karo4) to detect MUC1 or the core 1-bearing MUC1 was added in 2% BSA in washing buffer and incubated at room temperature for another hour. Again, this was washed three times, followed by addition of peroxidase-coupled streptavidin or peroxidase-coupled anti-mouse IgM(µ) antibody (Dianova) diluted 1:300 and 1:5000, respectively, in 2% BSA in washing buffer and incubation for 1 hour at room temperature. Finally, the plates were washed twice in washing buffer and once in PBS. The staining reaction was performed in 25 mM citric acid, phosphate buffer, pH 5.0, with 0.04% $H_2O_2$ and 0.4 mg/ml o-phenylenediamine (Sigma) in the dark at room temperature. The staining reaction was quenched by adding 2.5 N sulfuric acid (final concentration 0.07 N) and measured in an ELISA Reader at 492 nm with a 620 nm reference filter.

TABLE 9

Analysis of tumor-specific secretory MUC1 in culture supernatants of two cell lines and detection of core 1 before and after neuraminidase treatment in a sandwich ELISA

| Scavenger Ab | HMFG-1 | mIgG-Panko2 | |
| Detection Ab | mIgG- | anti-core 1 (mIgM-Karo4) | |
| Cell line | Panko2 | −Neuraminidase | +Neuraminidase |
| K562 | + | − | + |
| ZR-75-1 | +++ | − | + |
| T47D | ++ | − | +++ |

11. Detection of MUC1 in Serum of Colon Carcinoma Patients by Means of Recognition Molecules Specifically Recognizing the Glycosylated MUC1 Tumor Epitope A sandwich ELISA as described above was used to detect soluble MUC1 in patient serums. The anti-MUC1 antibody 115D8 (scavenger in the commercial CA 15-3 test) or mIgG-Panko2 (1 µg/ml PBS) was used as scavenger antibody. After blocking with 2% BSA/PBS, the serums were applied. 24 different colon carcinoma serums at different dilutions (from undiluted to 1:32 diluted) were investigated. Dilutions of a defined serum from a mammary carcinoma patient (152 U/ml, Enzymun Test CA 15-3, Boehringer Mannheim) were used as standard. A limit of 23 U/ml (average value for normal serums in the literature) was established. To detect bound MUC1, the mIgG-Panko2 was compared with two other anti-MUC1 antibodies, i.e. DF3 (detection antibody in the CA 15-3 test) and HMFG-1. All three antibodies were biotinylated (EZ-Link sulfo-NHS-LC-biotin, Pierce) and, after washing three times with PBS+ 0.1% Tween 20, coupled with streptavidin-POD (1:300 in 0.2% BSA/PBS) and detected with TMB as peroxidase substrate (see above).

The data are summarized in Table 10. Soluble MUC1 in serum of colon carcinoma patients gives significantly less binding with the recognition molecule mIgG-Panko2 of the invention compared to the well-known anti-MUC1 antibodies DF3 and HMFG-1.

TABLE 10

Detection of serum MUC1 in an ELISA using various anti-MUC1 antibodies.

| Scavenger antibody | Detection antibody | Samples above limit/total samples | % |
|---|---|---|---|
| 115D8 | DF3 | 20/24 | 83 |
| 115D8 | HMFG-1 | 19/24 | 79 |
| 115D8 | mIgG-Panko2 | 8/24 | 33 |
| mIgG-Panko2 | mIgG-Panko2 | 8/24 | 33 |
|  |  | 1/12 | 8 |

12. Tumor Therapy for the Reduction of MUC1-Positive Tumors in an In Vivo Tumor Model Using Radiolabelled Recognition Molecules Specifically Recognizing the Glycosylated MUC1 Tumor Epitope The therapeutic potential of mIgG-Panko2 was investigated in the ZR-75-1 tumor model (see Example 9). To this end, the chelated recognition molecules (see Example 7) were loaded (pH 4.5, 37° C., 30 min; cf. incorporation of $^{111}$indium) with $^{90}$yttrium (a β-emitter to destroy tumor cells), and the stability was controlled using thin layer chromatography.

One week to eight weeks after subcutaneous injection of the ZR-75-1 cells (depending on the desired tumor size as model for the treatment of solid medium-sized (about 0.3 cm$^3$) or large tumors (>0.5 cm$^3$) or treatment of minimal residual disease (<0.05 cm$^3$)), the tumor-bearing mice were given 200 µl into the tail vein. The injection solution contained the $^{90}$Y-labelled mIgG-Panko2 (100 µCi per dose; specific activity: 3 mCi/mg antibody) in Ca/Mg-PBS with 4% fetal calf serum to protect from radiolysis. Control groups received the same injection with no radioactively labelled recognition molecule or with radiolabelled control antibody ($^{90}$Y-MOPC21).

Body weight and tumor size were measured twice a week and compared. The relative tumor growth was determined considering the respective tumor size at the beginning of treatment. A second injection (50 µCi per dose) was given about three weeks after the first treatment. This type of treatment resulted in a strong anti-tumor effect in all tested animals. When treating small (<0.05 cm$^3$) or medium-sized tumors (about 0.3 cm$^3$), it was possible to completely inhibit tumor growth over the entire period of observation (6 weeks; FIGS. 14a and 14b). In animals with very large tumors (>0.5 cm$^3$) at the beginning of treatment, it was possible to suppress tumor growth for about three weeks (FIG. 14c). Due to the tumor size no longer within the bounds of what is reasonable, a second injection was not possible in the control group.

Treatment with an irrelevant $^{90}$Y-labelled antibody (MOPC21) at the same dosage gives only minor reduction of tumor growth compared to untreated animals (FIG. 14d), which may be due to non-specific irradiation as a result of relatively slow depletion of the antibody in the serum.

Apart from minor myelotoxicity, treatment with the $^{90}$Y-labelled mIgG-Panko2 showed no side effects.

13. Detection of Antibody-Dependent Cellular Cytotoxicity of Recognition Molecules, which Specifically Recognize the Glycosylated MUC1 Tumor Epitope, in an In Vitro Model The antibody-dependent cellular cytotoxicity (ADCC) of the recognition molecules according to the invention was investigated in an europium release test. The target cells (ZR75-1 or MCF-7; 5×10$^6$) were incubated for 10 minutes at 4° C. in 800 µl of europium buffer (50 mM HEPES, pH 7.4, 93 mM NaCl, 5 mM KCl, 2 mM MgCl$_2$, 10 mM diethylenetriaminepentaacetic acid, 2 mM europium(III) acetate), electroporated (710 V, 1 pulse, 30 µs) in a Multiporator (Eppendorf), and subsequently incubated on ice for another 10 min. Thereafter, the cells were washed 5 times in RPMI 1640/5% FCS and seeded in a 96-well round-bottom plate (Nunc; 5×10$^3$ in 100 µl per well). Following addition of 20 µl of mIgGPanko2, HMFG-1, cIgG-Panko1 or cIgG-Panko2 at varying concentrations (0.2 to 25 µg/ml final concentration in 200 µl incubation volume) or the corresponding controls (medium, isotype control hIgG), human peripheral blood cells (80 µl/well, preparation see Example 14) were added as effector cells, using an effector cell/target cell ratio of 5 to 100:1. 80 µl RPMI/FCS with no effector cells was added to determine the spontaneous release. Maximum release was determined after complete lysis of the target cells with ethanol. Following incubation in an incubator at 37° C. for 4 to 20 hours, the plate was centrifuged at 500×g for 5 minutes, and 20 µl of sample each time was pipetted in 200 µl per well of enhancement solution (Perkin-Elmer Wallac). Following incubation for 15 minutes at room temperature, the fluorescence was determined (Victor$^2$ Fluorometer, Perkin-Elmer Wallac). The specific cytotoxicity is obtained from the equation (experimental lysis−spontaneous lysis)/(maximum lysis−spontaneous lysis).

The chimeric IgGs of Panko1 and Panko2 show high specific lysis of the MUC1-positive target cells (FIG. 15a). The murine IgG of Panko2 shows somewhat lower cytotoxicity compared to the chimeric recognition molecules, but a clearly greater effect than the murine anti-MUC1 antibody HMFG-1, with slight lysis being observed only at the highest tested concentration for the latter (FIG. 15b).

14. Analysis of Binding of Recognition Molecules, which Specifically Recognize the Glycosylated MUC1 Tumor Epitope, to Human Blood Cells Expression of MUC1 on hematopoietic cells could be detected by means of various anti-MUC1 antibodies. However, differing results with different anti-MUC1 antibodies allow the conclusion that recognition of non-epithelial MUC1 is highly dependent on the fine specificity of the respective antibody, and that varying glycosylation patterns of MUC1 are present on the cells. Binding of the recognition molecules of the invention to human blood cells was investigated using flow cytometry.

Human peripheral blood cells were obtained from the blood of healthy donors using density centrifugation (Ficoll-Hypaque). The cell layer was removed and washed 3 times with RPMI 1640/5% FCS. The cells were used either in fresh condition or cryopreserved and thawed in RPMI 1640/10% FCS prior to use in cell staining or as effector cells in the ADCC test (see Example 13). To stimulate human T cells, the isolated blood cells were incubated in RPMI/FCS+1 µg/ml PHA+60 U/ml hIL-2 in an incubator for 3 to 8 days. Stimulation was monitored in flow cytometry by detecting the activation marker CD25.

The isolated blood cells were incubated with mIgG-Panko1, mIgG-Panko2, HMFG-1 or DF3 and with an mIgG1 isotype control as a control for one hour on ice. Following washing with PBS, the cells were incubated with Cy3-conjugated goat anti-mouse Ig (Dianova) and/or with a CD marker-specific (CD3, CD14, CD19), FITC-labelled antibody (30 min, 4° C., in the dark). Following washing, the cells were analyzed using flow cytometry.

None of the tested antibodies binds to non-activated T cells. After PHA stimulation, the MUC1 expression on human T cells is upregulated. This MUC1 is detected strongly by HMFG-1 and DF3, but only to a minor extent by Panko2. Panko1 shows no binding to PHA-stimulated blood cells (FIG. 16). Panko2 and DF3 recognize MUC1 neither on monocytes nor on B cells. In contrast, HMFG-1 and Panko1 give weak binding to monocytes and HMFG-1 also binds to B cells (FIG. 16), the detected surface densities being significantly lower than those on activated T cells.

BRIEF DESCRIPTION OF THE SEVERAL VIEWS OF THE DRAWINGS

FIG. 14d shows the treatment of tumor-bearing mice with $^{90}$Y-mIgG-Panko2 compared to an irrelevant radiolabelled control antibody $^{90}$Y-MOPC21.

Figure 1:
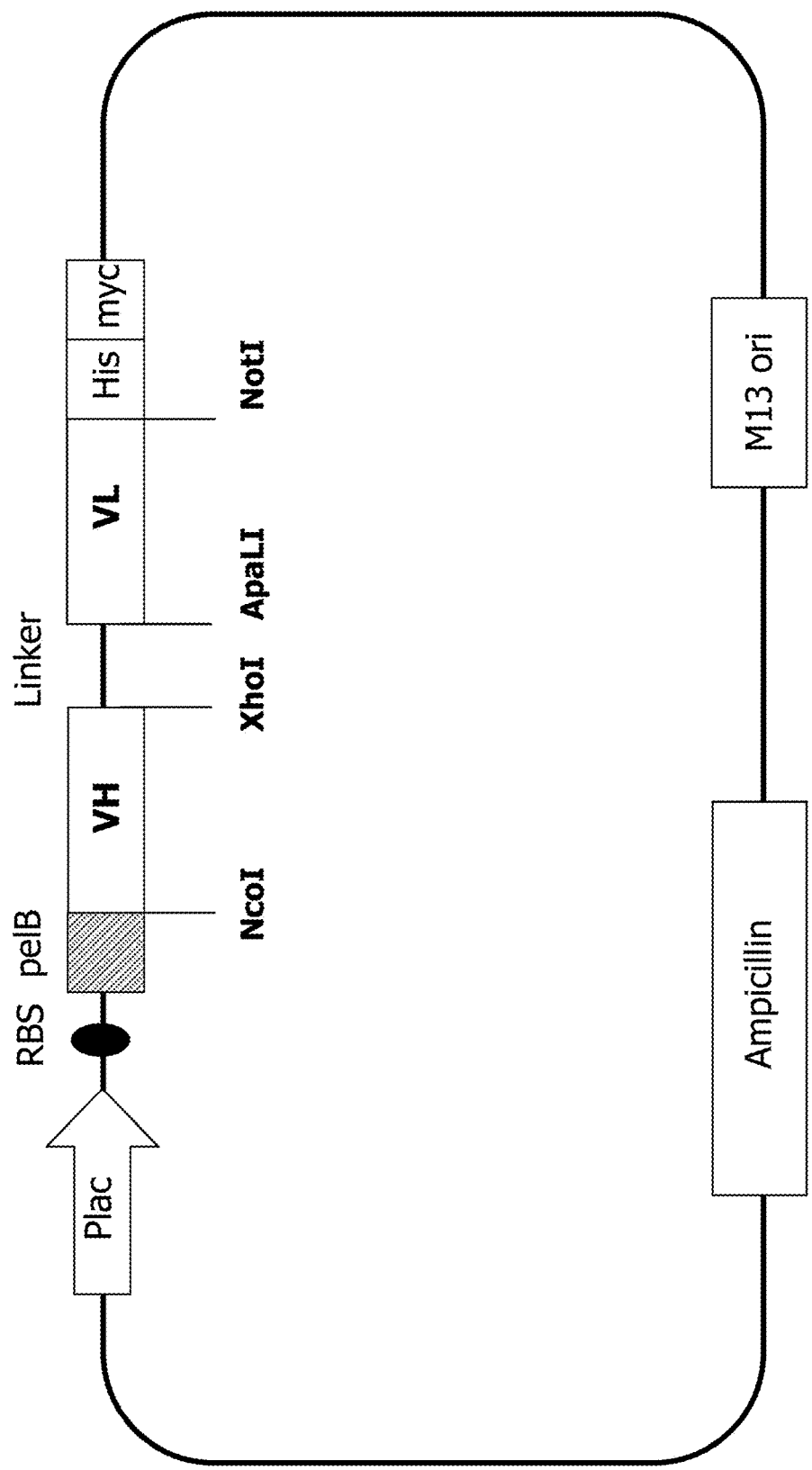
FIG. 1: Vector for cloning and bacterial expression of single-chain antibody fragments.
Figure 2:
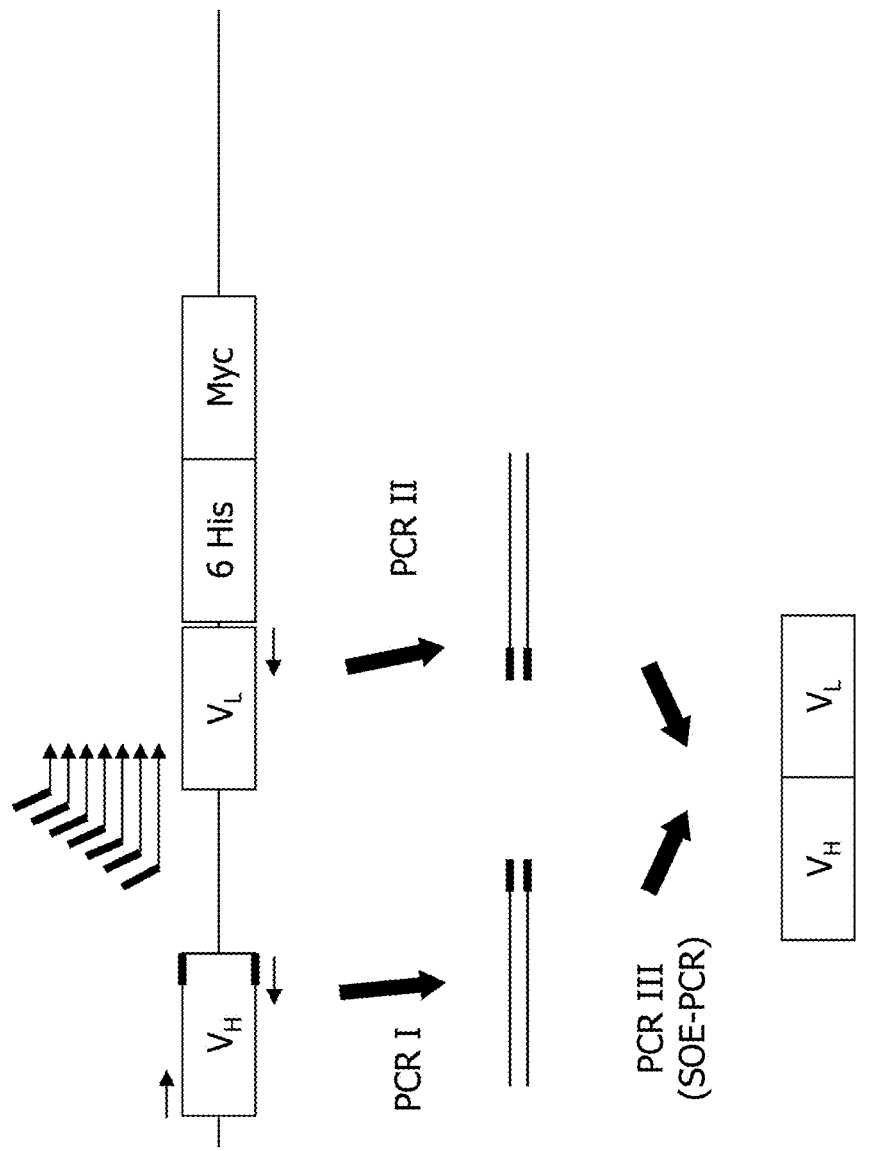
FIG. 2: Cloning diagram for the preparation of single-chain antibody fragments having different linker length.
Figure 3:
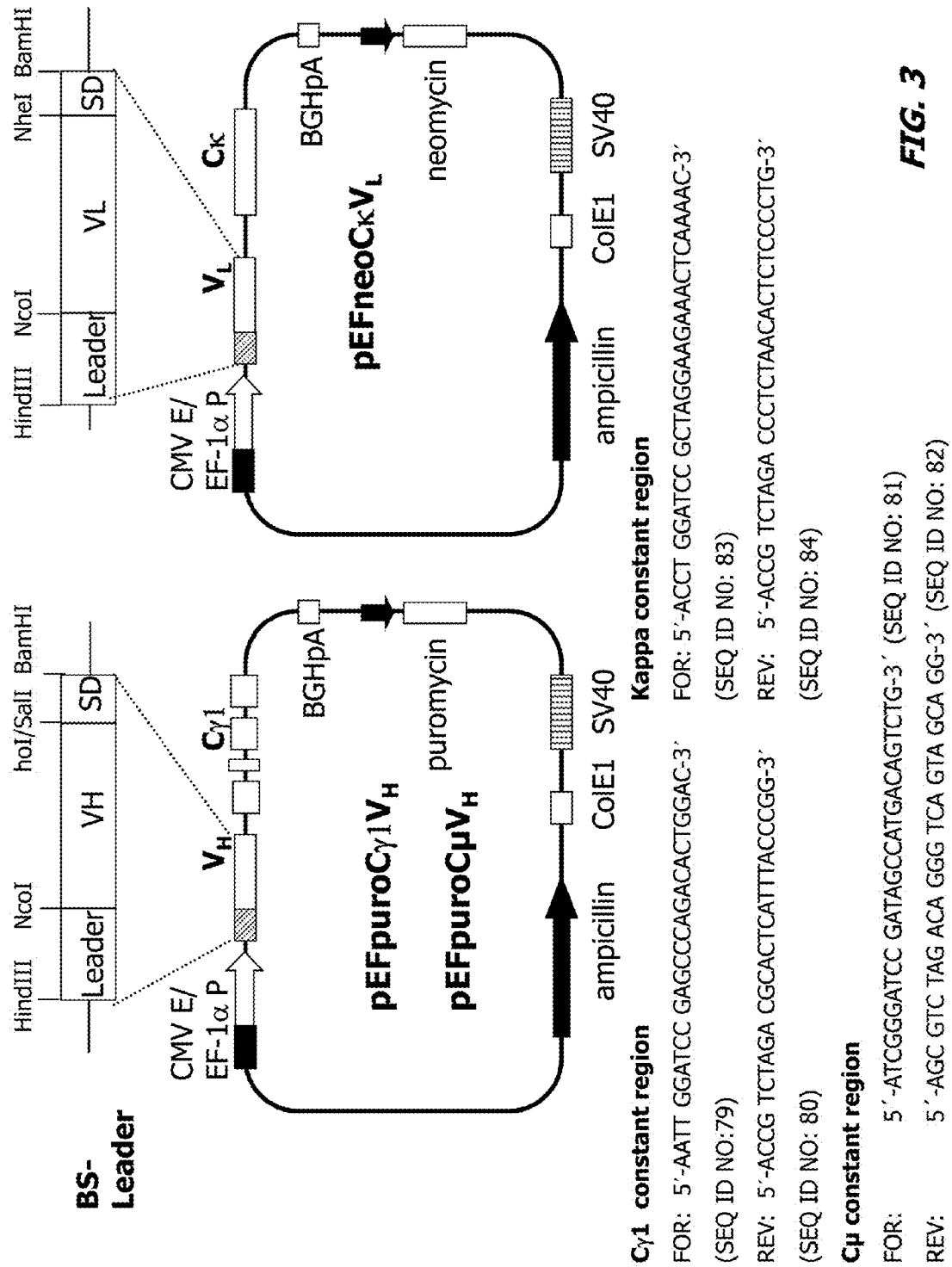
FIG. 3: Vector system for cloning and eukaryotic expression of chimeric antibodies in IgG1 or IgM format.
Figure 4:
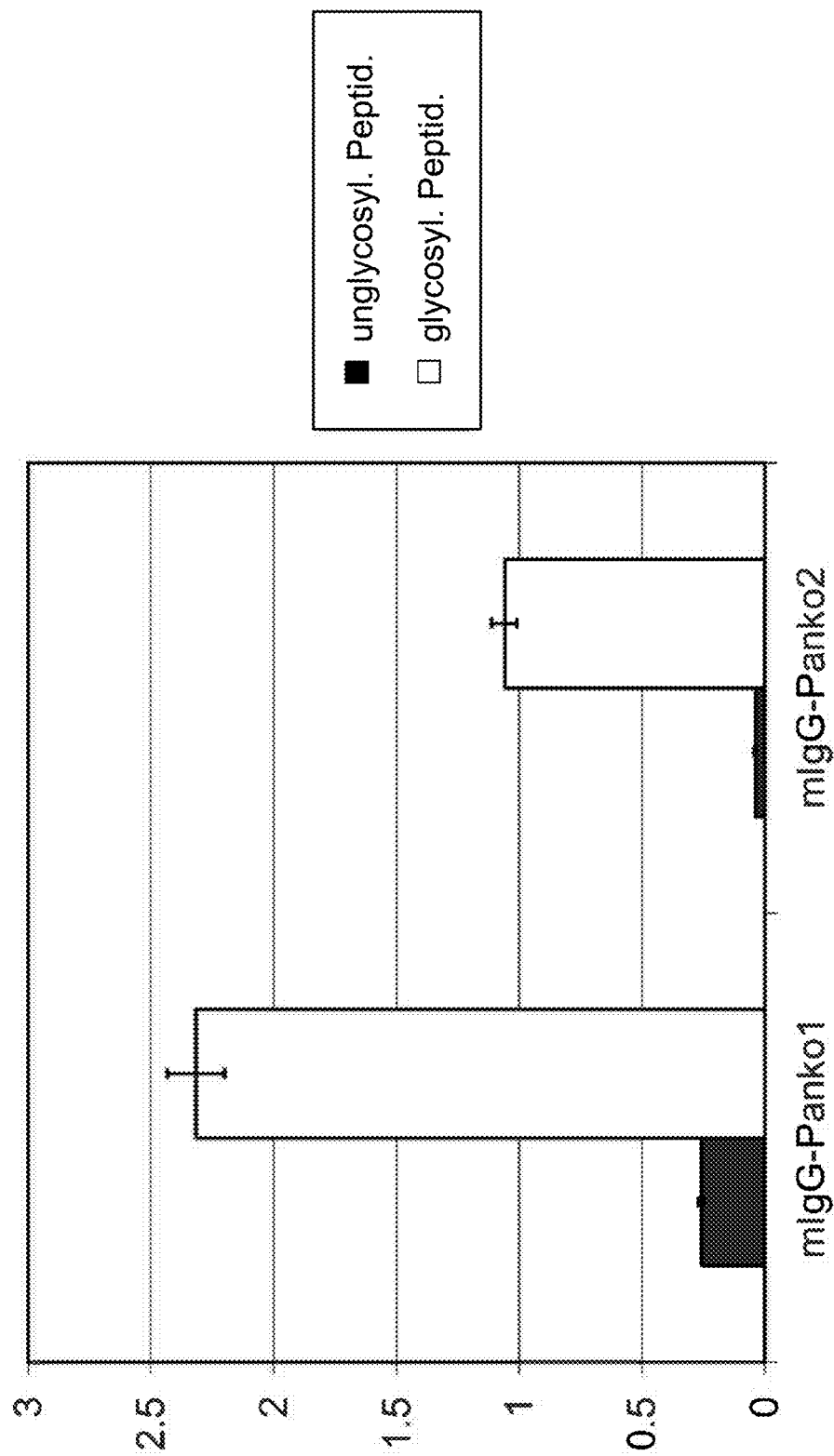
FIG. 4: Binding of the recognition molecules of the invention, mIgG-Panko1 and mIgG-Panko2, to glycosylated and non-glycosylated MUC1 peptide in an ELISA. Binding of the recognition molecules of the invention, mIgG-Panko1 and mIgG-Panko2, to glycosylated and non-glycosylated MUC1 peptide in an ELISA. The non-glycosylated 30mer with the sequence APPAHGVTSAPDTRPAPGSTAPPAHGVTS (SEQ ID NO: 78) and the glycosylated 30mer with the sequence APPAHGVTSAPDT[GalNAcα]R PAPGSTAPPAHGVTSA (SEQ ID NO: 71) were used as antigens and bound in PBS to the plate. The mIgG-Panko1 and mIgG-Panko2 antibodies were employed at a concentration of 0.5 µg/ml in the ELISA.
Figure 5:
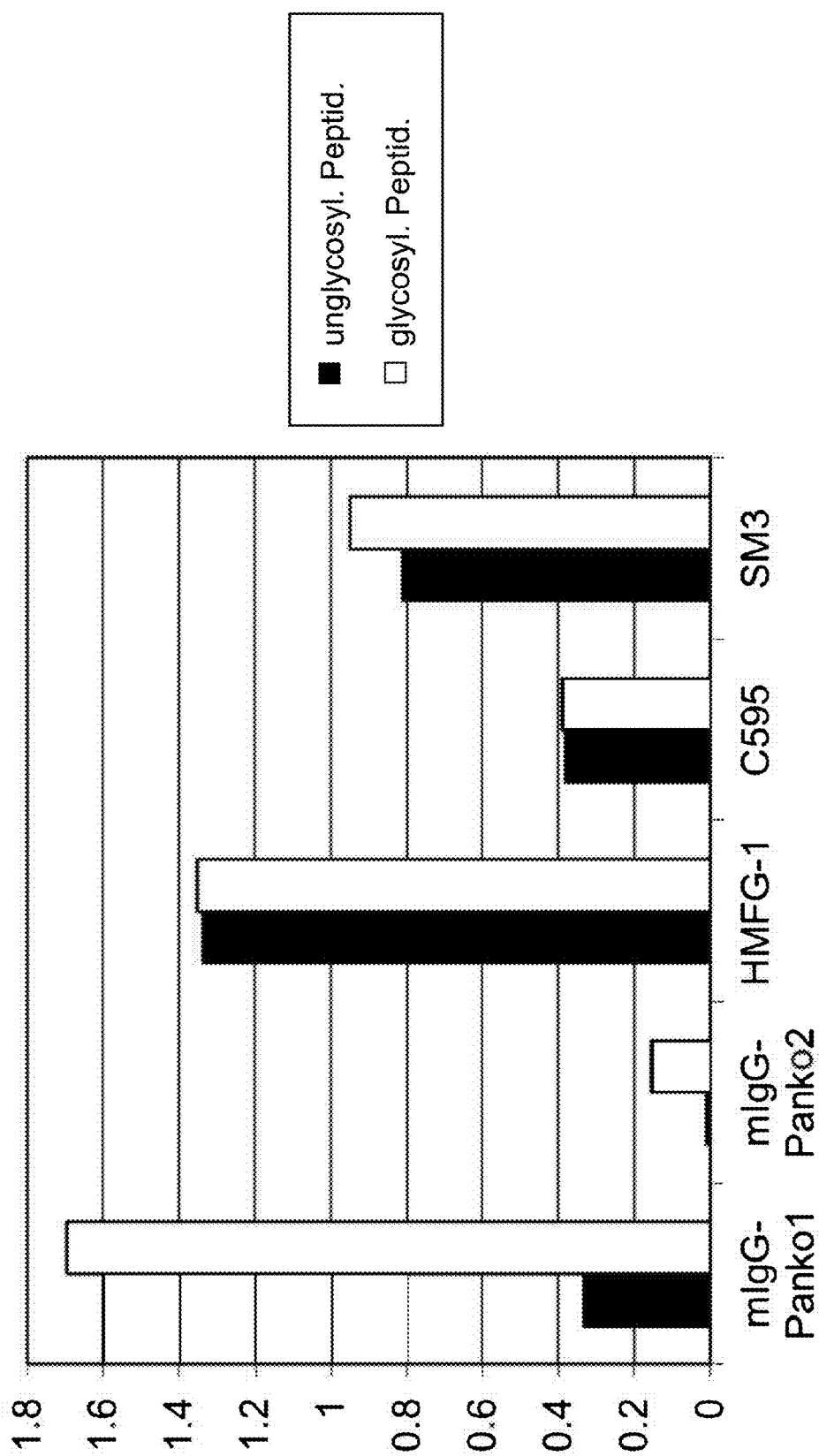
FIG. 5: Comparison of specific binding of the anti-MUC1 antibodies HMFG-1, C595 and SM3 with mIgG-Panko1 and mIgG-Panko2 to glycosylated and non-glycosylated MUC1 peptide in an ELISA. Comparison of specific binding of the anti-MUC1 antibodies HMFG-1, C595 and SM3 with mIgG-Panko1 and mIgG-Panko2 to glycosylated and non-glycosylated MUC1 peptide in an ELISA. The non-glycosylated 30mer with the sequence APPAHGVTSAPDTR-PAPGSTAPPAHGVTS (SEQ ID NO: 78) and the glycosylated 30mer with the sequence APPAHGVTSAPDT [GalNAcα]RPAPGSTAPPAHGVTSA(SEQ ID NO: 71) were used as antigens and dried slightly on the plate in $H_2O$. The antibodies were employed at a concentration of 10 µg/ml in the ELISA.
Figure 6:
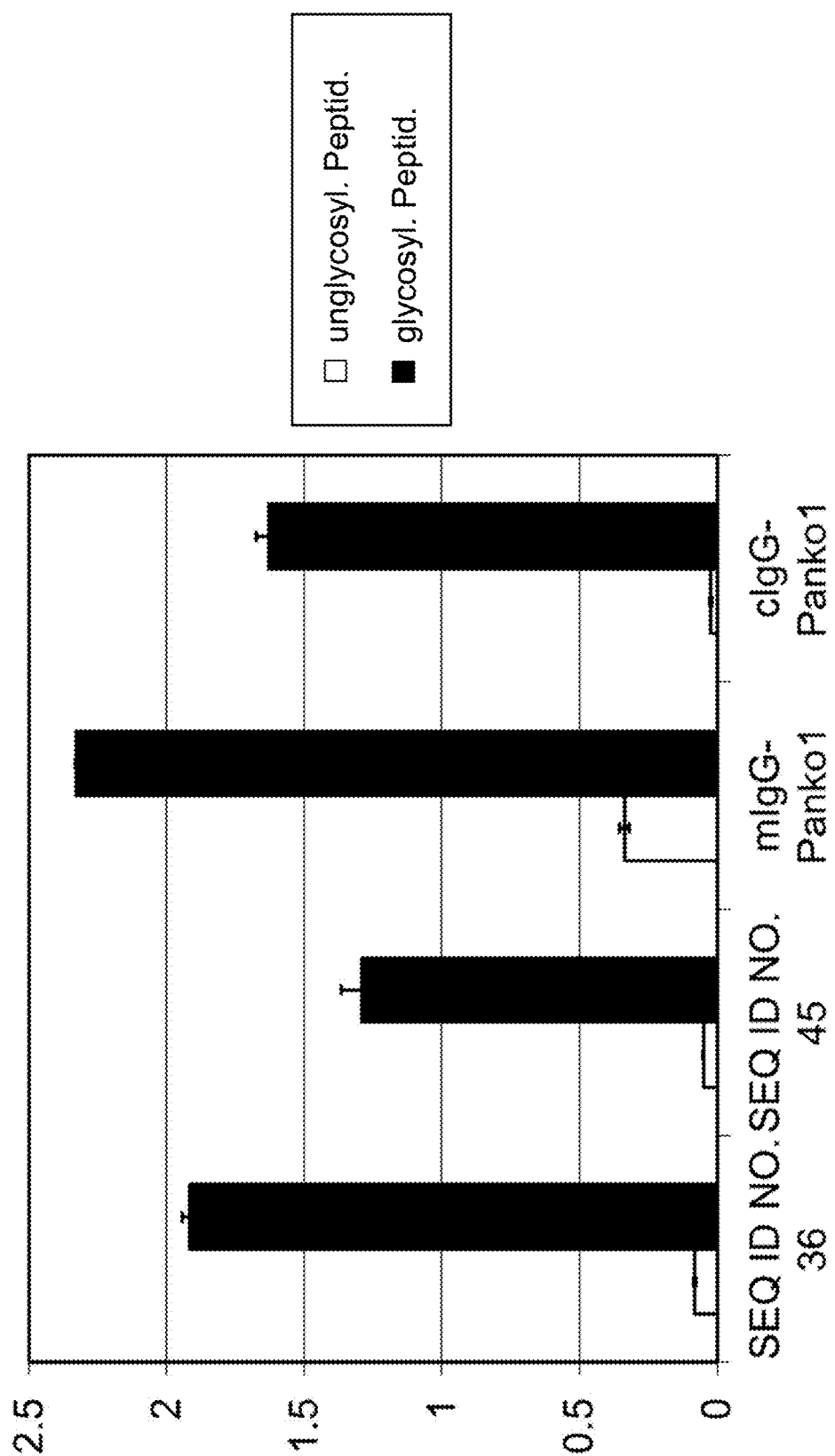
FIG. 6: Specific binding of various preferred formats of recognition molecules of the invention in an ELISA, exemplified using non-glycosylated and glycosylated 30mer MUC1 peptide. Specific binding of various preferred formats of recognition molecules of the invention in an ELISA, exemplified using non-glycosylated and glycosylated 30mer MUC1 peptide. The non-glycosylated 30mer with the sequence APPAHGVTSAPDTRPAPGSTAPPAH GVTS (SEQ ID NO: 78) and the glycosylated 30mer with the sequence APPAHGVTSAPDT [GalNAcα]RPAPG-STAPPAHGVTSA (SEQ ID NO: 71) were used as antigens and bound in PBS to the plate. The two scFv formats SEQ ID Nos. 36 and 45 were used with 0.5 µg/ml, the murine IgG with 0.1 µg/ml and the chimeric IgG with 0.01 µg/ml. As different secondary antibodies are used for these various formats, the ELISA data should be assessed merely qualitatively.
Figure 7:
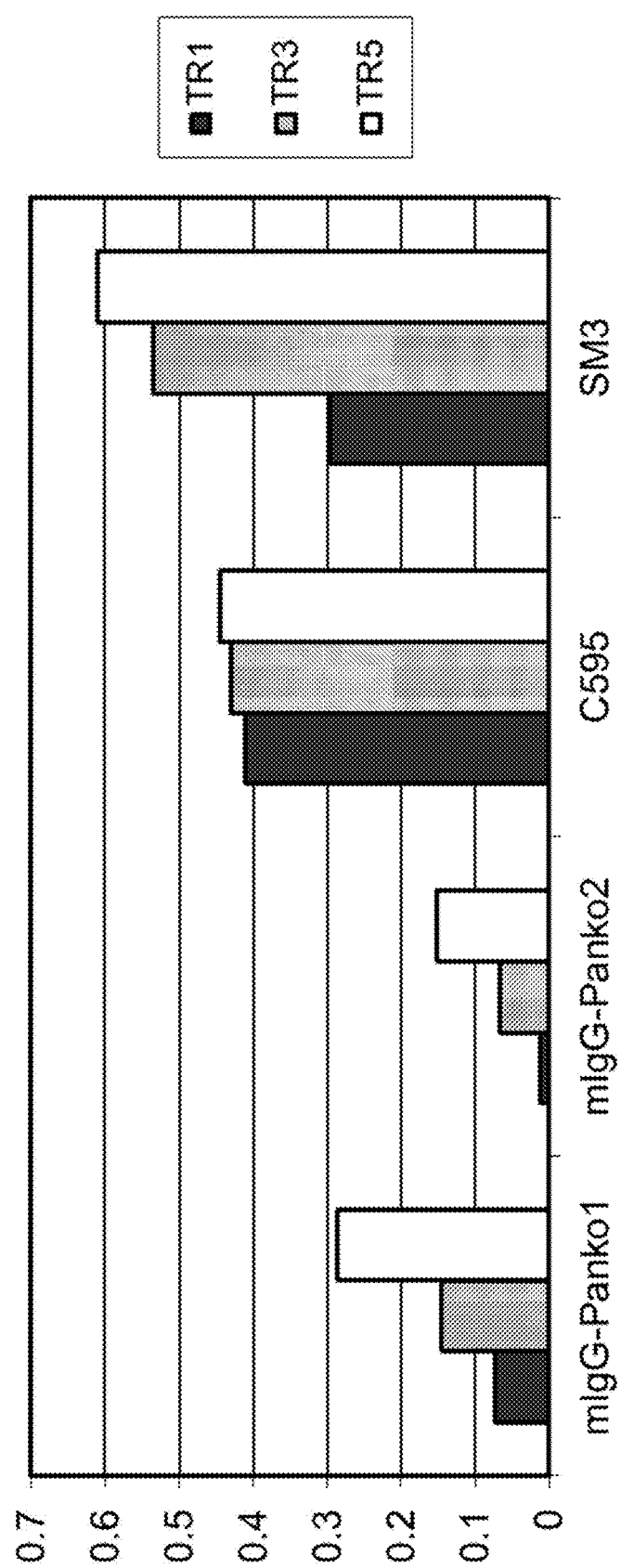
FIG. 7: Dependence of binding of the recognition molecules mIgG-Panko1 and mIgG-Panko2 of the invention on the number of tandem repeats in non-glycosylated MUC1 peptides compared to the MUC1-specific antibodies SM3 and C595 in an ELISA. Dependence of binding of the recognition molecules mIgG-Panko1 and mIgG-Panko2 of the invention on the number of tandem repeats in non-glycosylated MUC1 peptides compared to the MUC1-specific antibodies SM3 and C595 in an ELISA. A series of non-glycosylated MUC1 peptides of varying length with the sequence [VTSAPDTRPAPGSTAPPAHG]$_n$, wherein n=1 (SEQ ID NO: 72), 3 (SEQ ID NO: 73) and 5 (SEQ ID NO: 74) (TR1, TR3 and TR5), was used as antigens and dried slightly on the plate in $H_2O$. The antibodies were employed at a concentration of 10 µg/ml.
Figure 8:
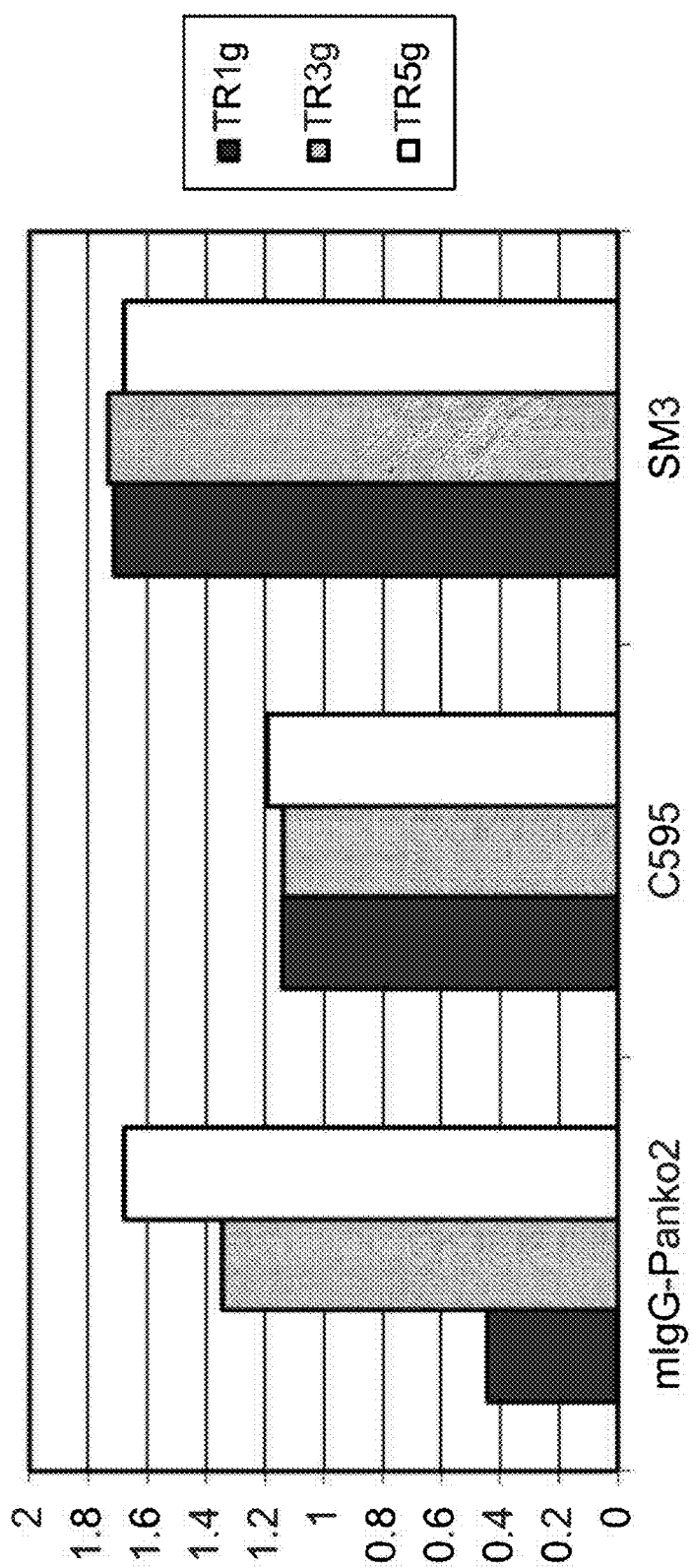
FIG. 8: Dependence of binding of the recognition molecules mIgG-Panko1 and mIgG-Panko2 of the invention on the number of tandem repeats (multiple glycosylated PDTR regions) compared to the MUC1-specific antibodies SM3 and C595 in an ELISA. A series of glycosylated MUC1 peptides of varying length with the sequence A[HGVT-SAPDT(GalNAcα)RPAPGSTAPPA]$_n$, wherein n=1 (SEQ ID NO: 75), 3 (SEQ ID NO: 76) and 5 (SEQ ID NO: 77) (TR1, TR3 and TR5), was used as antigens and dried slightly on the plate in $H_2O$. The antibodies were employed at a concentration of 10 µg/ml.
Figure 9:
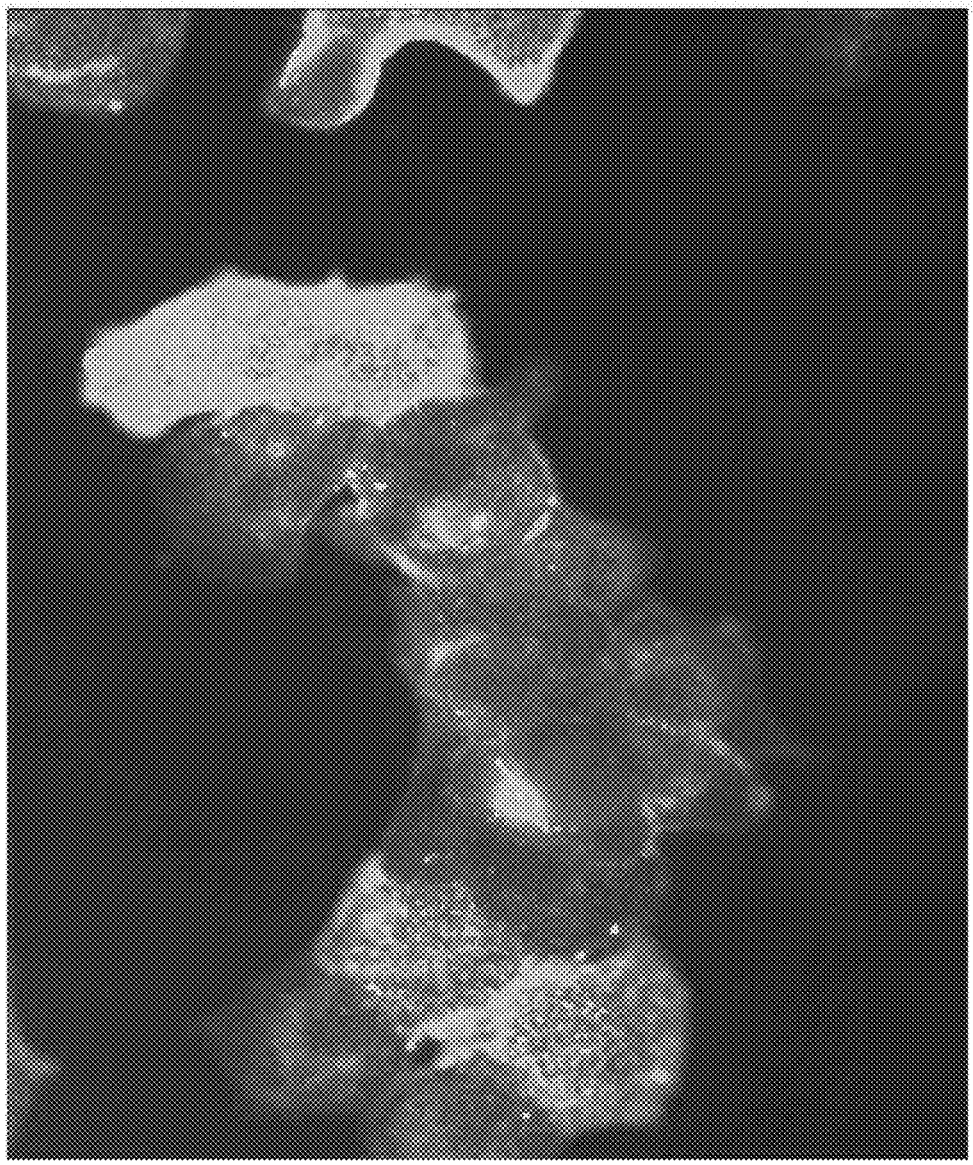
FIG. 9: Fluorescence labelling of cells of the tumor cell line T47D (mammary carcinoma) with the MUC1-specific recognition molecule mIgG-Panko2.
Figure 10:
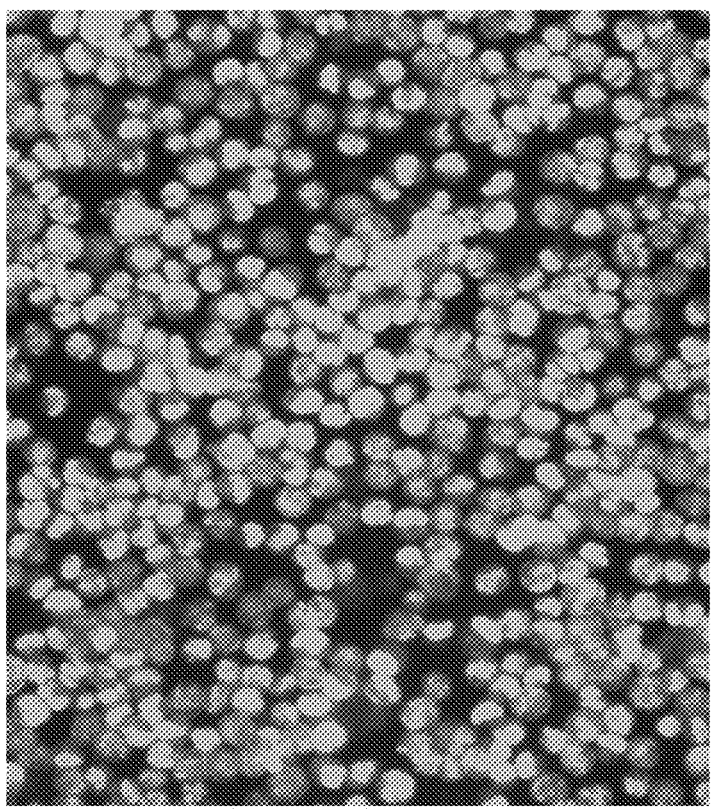
FIG. 10: Fluorescence labelling of cells of the tumor cell line K562 (erythroid leukemia) with the MUC1-specific recognition molecule cIgG-Panko1.
Figure 10:
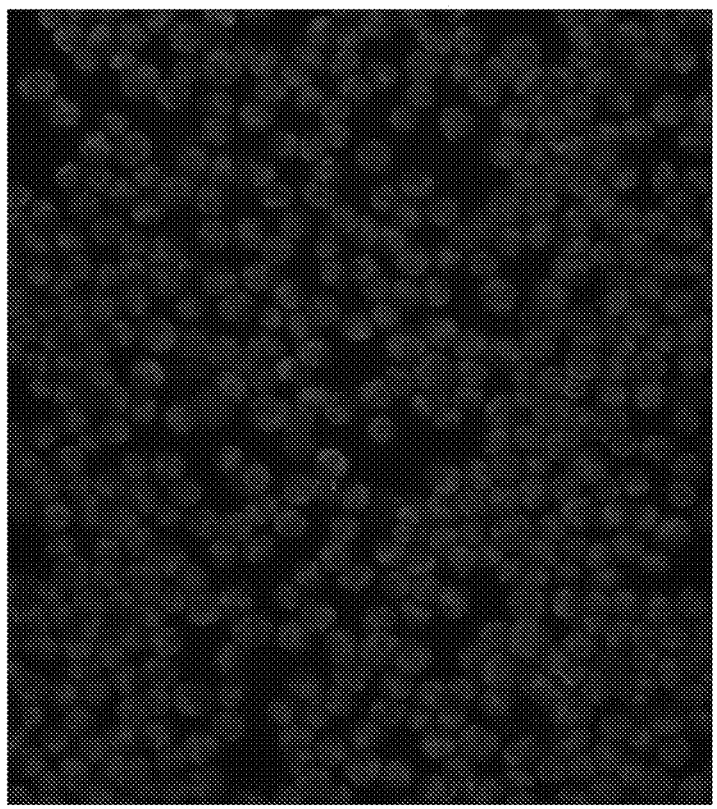
Figure 11A:
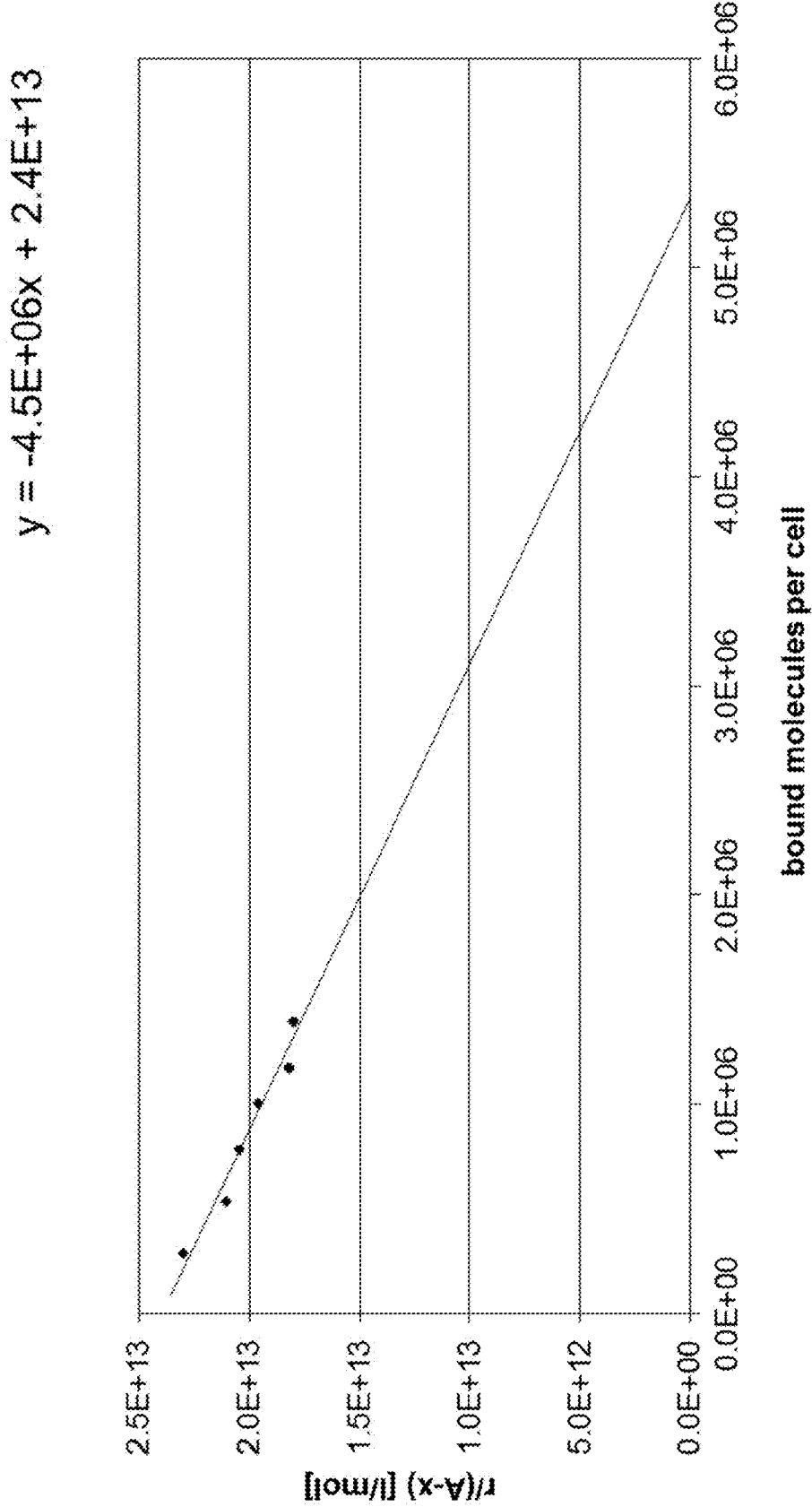
FIG. 11A-B: Scatchard diagram for the analysis of cell binding of radiolabelled MUC1-specific recognition molecules. Binding data of the two scFv formats SEQ ID NO. 36 (a) and SEQ ID NO. 45 (b) are exemplified. r: bound molecules per cell, A: employed concentration of radiolabelled recognition molecule [M], x: percentage bound to cells [M]. The difference A−x represents the concentration of free recognition molecules in the batch. The corresponding straight-line equation is given at the top, the slope of the straight-line representing the association constant.
Figure 11B:
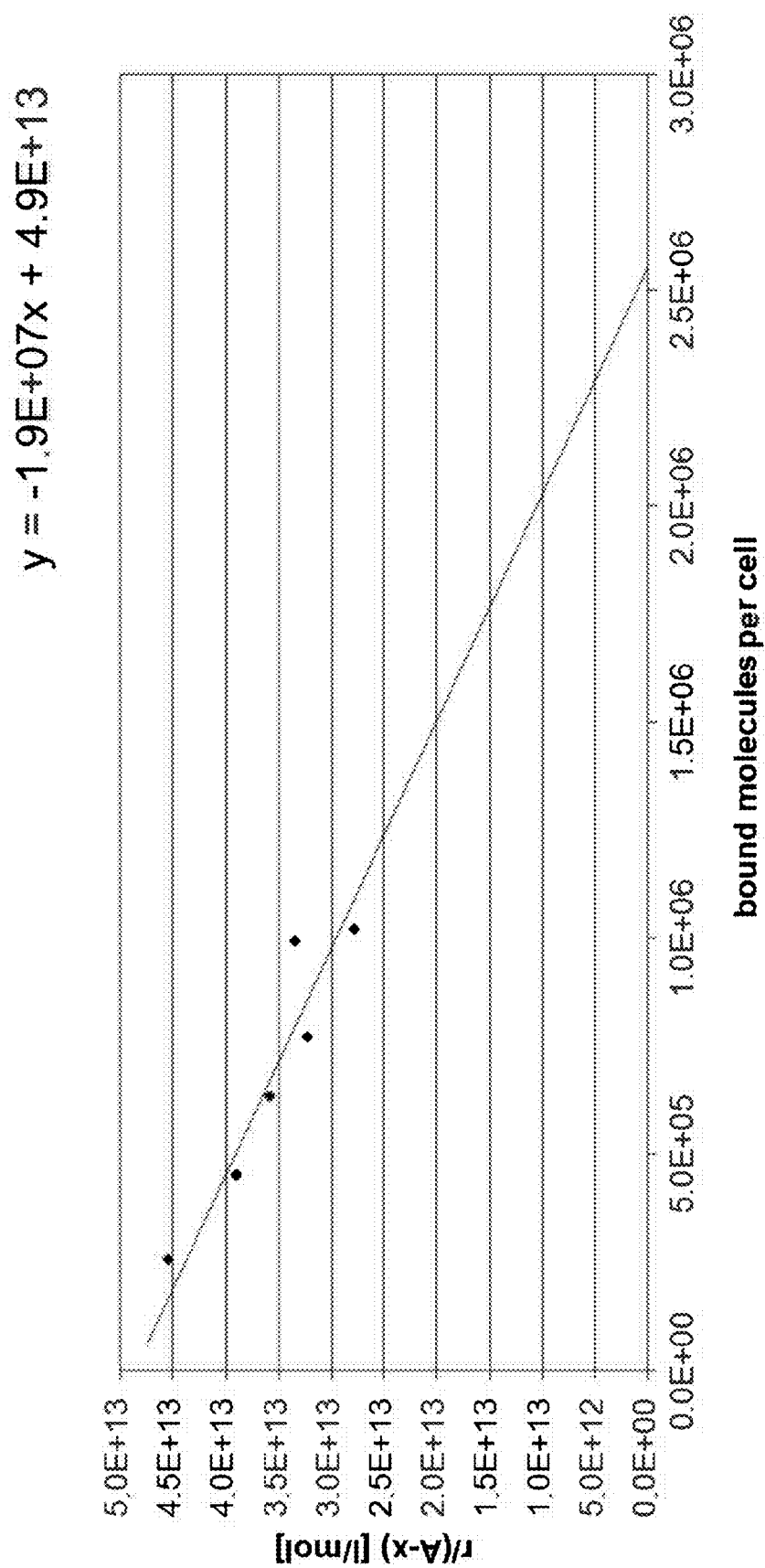
Figure 12:
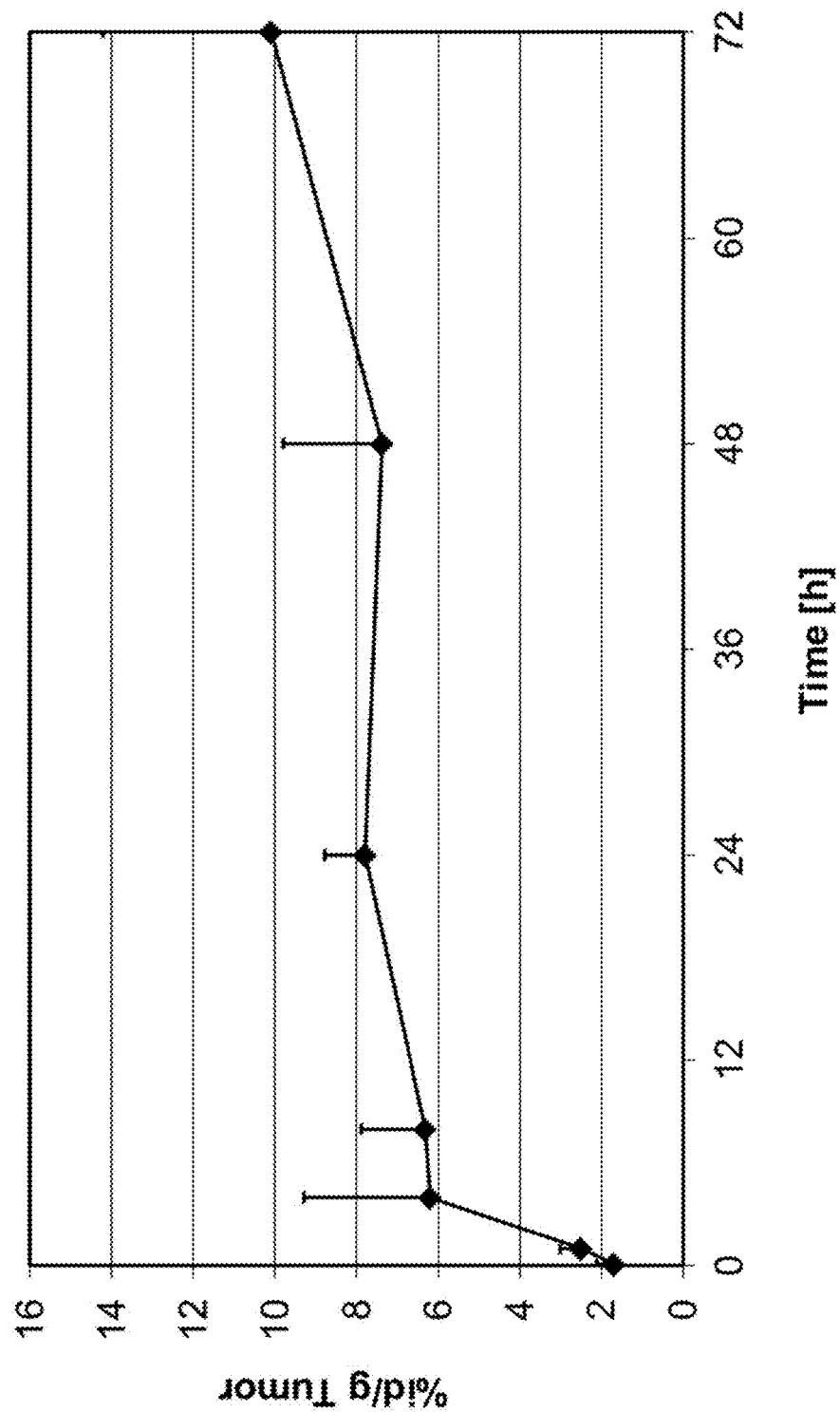
FIG. 12: Specific accumulation of the radiolabelled recognition molecule mIgG-Panko2 in a tumor in a mouse xenotransplant model. Each tumor-bearing mouse (n=5 per point in time) was administered i.v. with 5 µg of $^{111}$In-labelled mIgG-Panko2. The mice were sacrificed after the time as indicated, and accumulation in the tumor, relative to injected dose and tumor weight (% ID/g), was determined.
Figure 13:
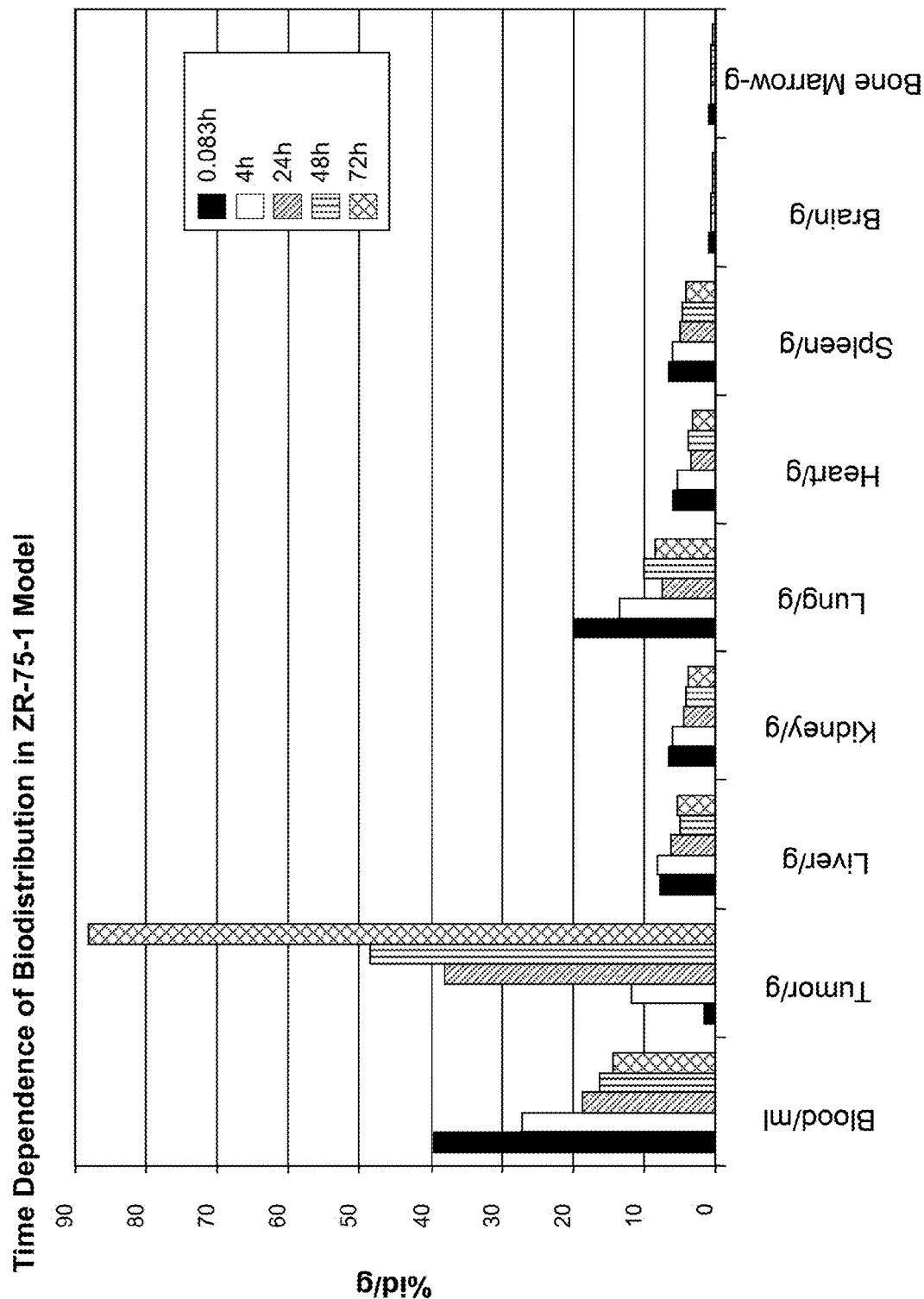
FIG. 13: High specific accumulation of the radiolabelled recognition molecule mIgG-Panko2 in a tumor in a mouse-ZR-75-1 tumor cell model. Each tumor-bearing mouse (n=6 per point in time) was administered i.v. with 5 μg of $^{111}$In-labelled mIgG-Panko2. The mice were sacrificed after the time as indicated, and accumulation in the tumor, in serum and organs, relative to injected dose and tumor or organ weight (% ID/g), was determined.
Figure 14A:
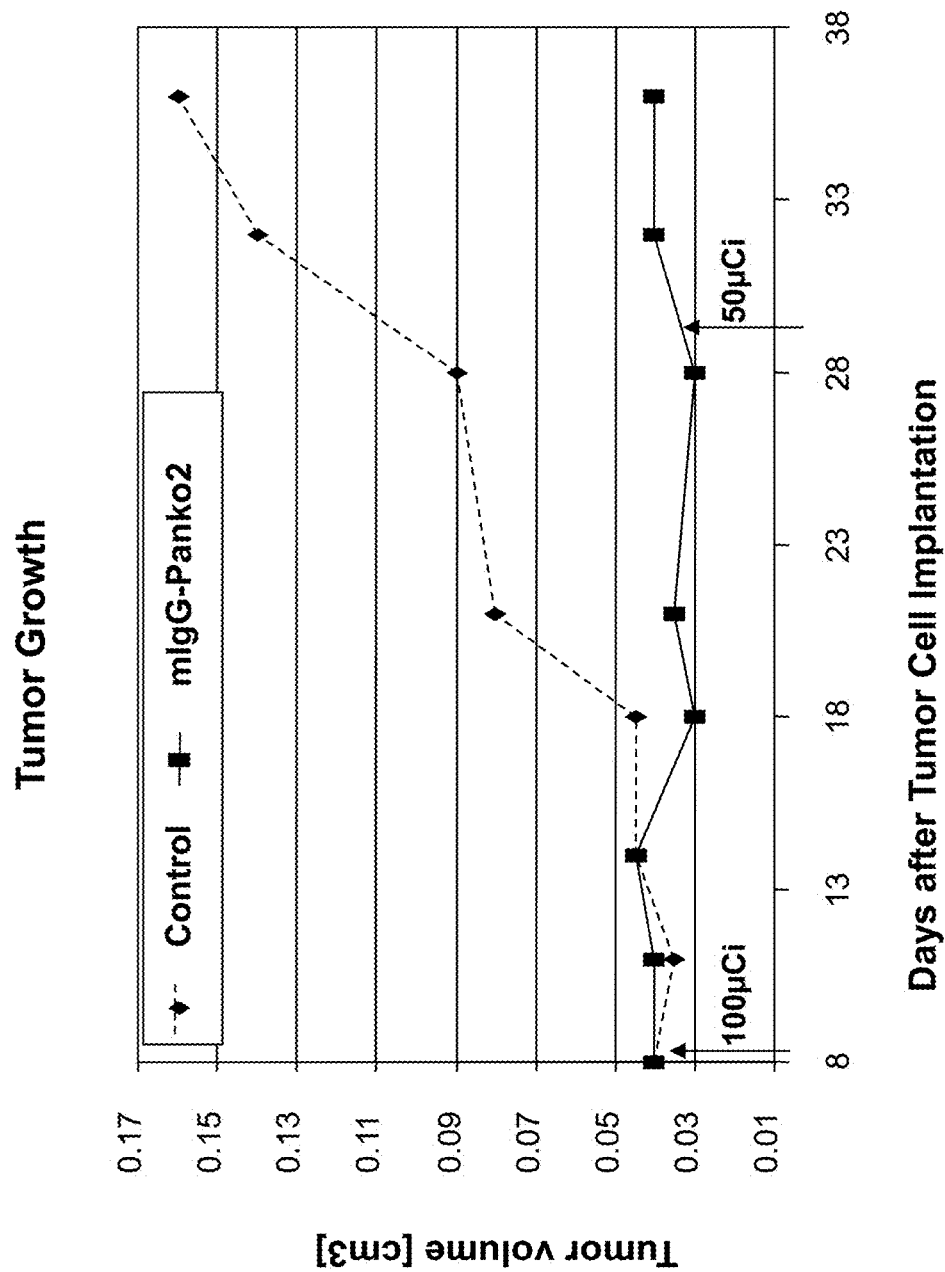
FIG. 14A-D: Inhibition of tumor growth in tumor-bearing mice after treatment with the radiolabelled recognition molecule mIgG-Panko2. On day 8 (14a; small tumors: <0.05 cm$^3$), on day 36 (14b; medium-sized tumors: about 0.3 cm$^3$) and on day 57 (14c; large tumors: >0.5 cm$^3$) after subcutaneous injection of the ZR-75-1 cells, the tumor-bearing mice were given 200 μl into the tail vein. The injection solution contained the $^{90}$Y-labelled mIgG-Panko2 (100 μCi per dose; specific activity: 3 mCi/mg antibody) in Ca/Mg-PBS with 4% fetal calf serum to protect from radiolysis. Control groups received the same injection with no radioactively labelled recognition molecule. In the event of small and medium-sized tumors, a second injection (50 μCi) was effected about 3 weeks later.
Figure 14B:
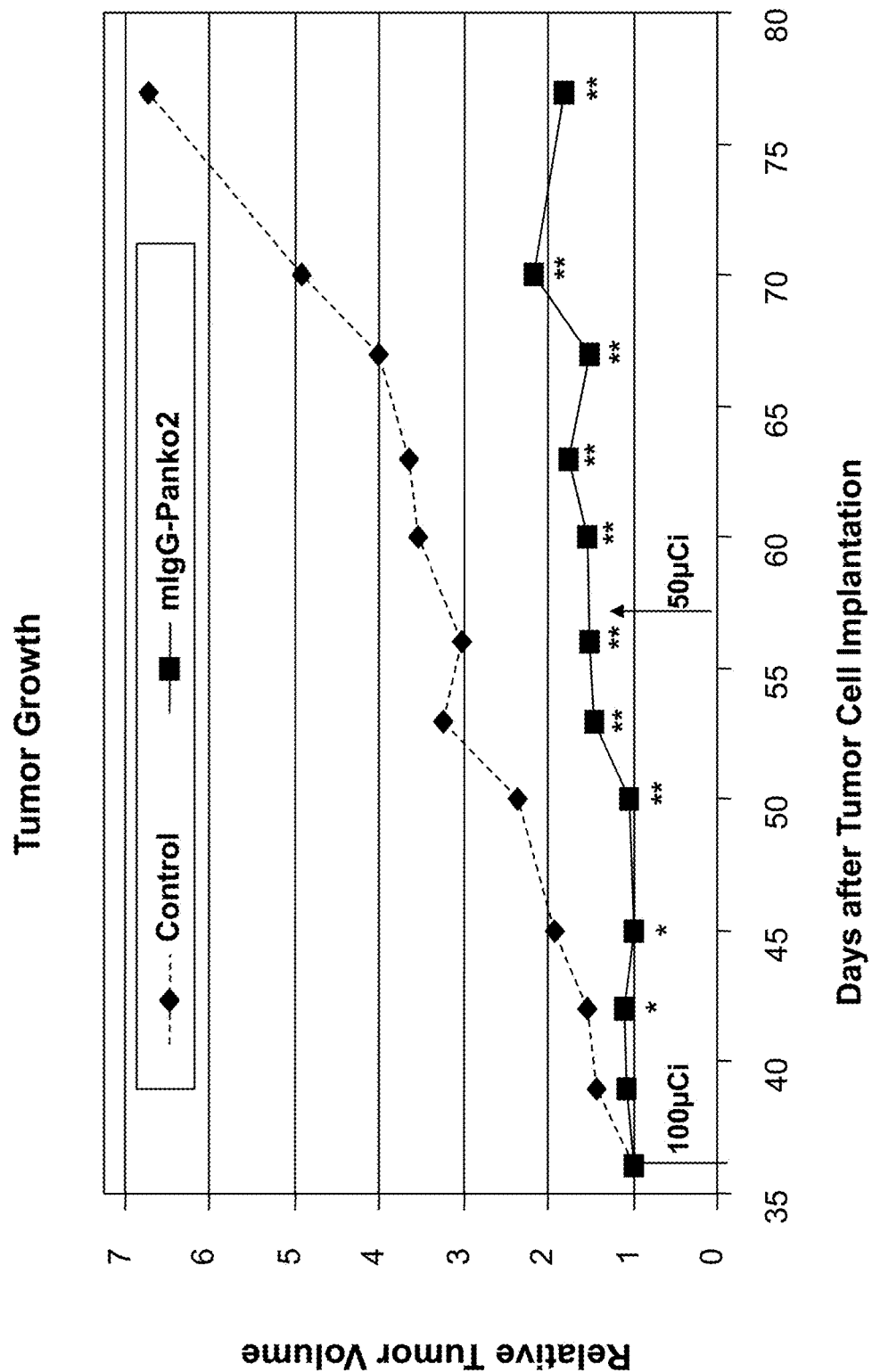
Figure 14C:
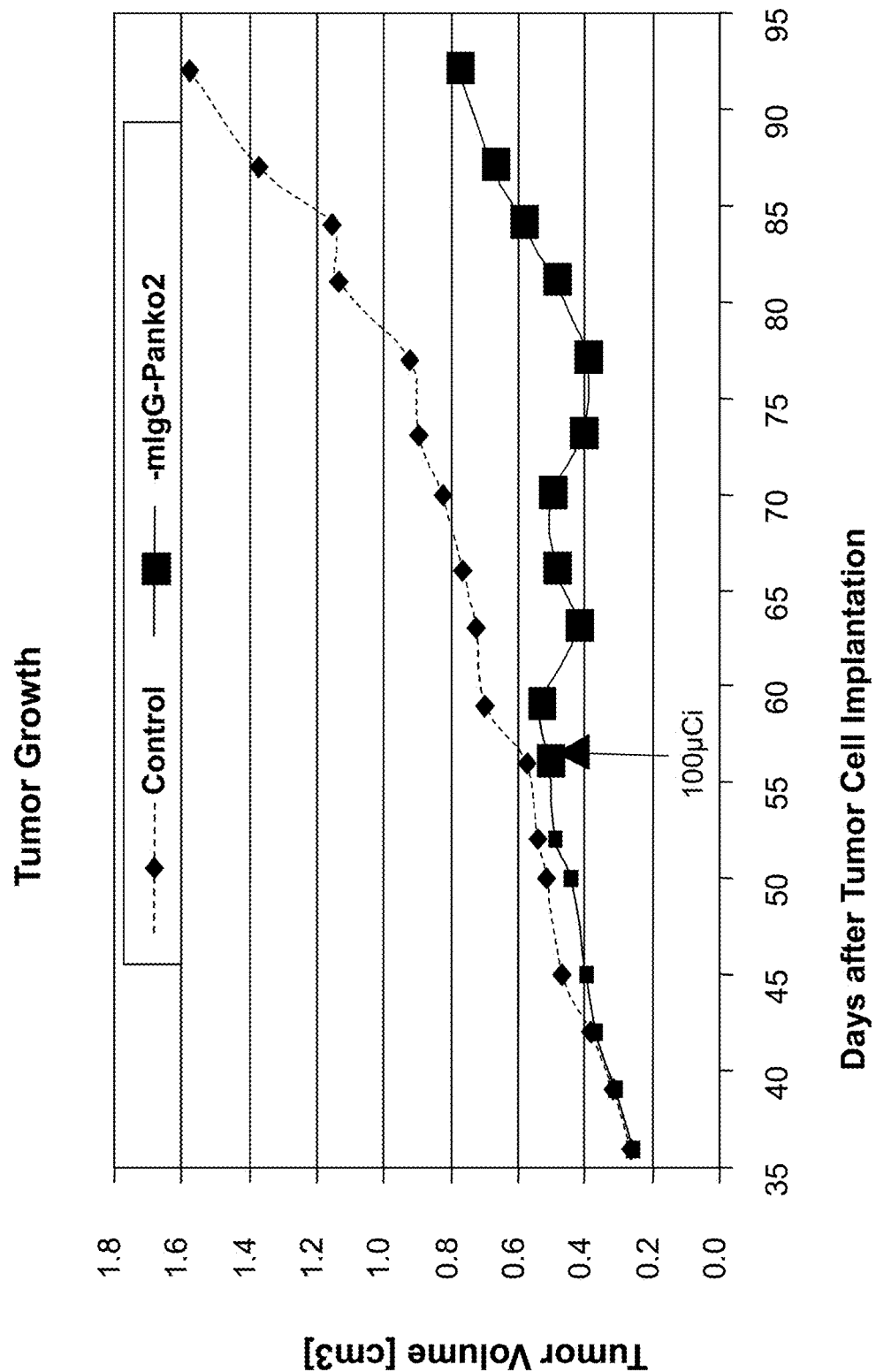
Figure 14D:
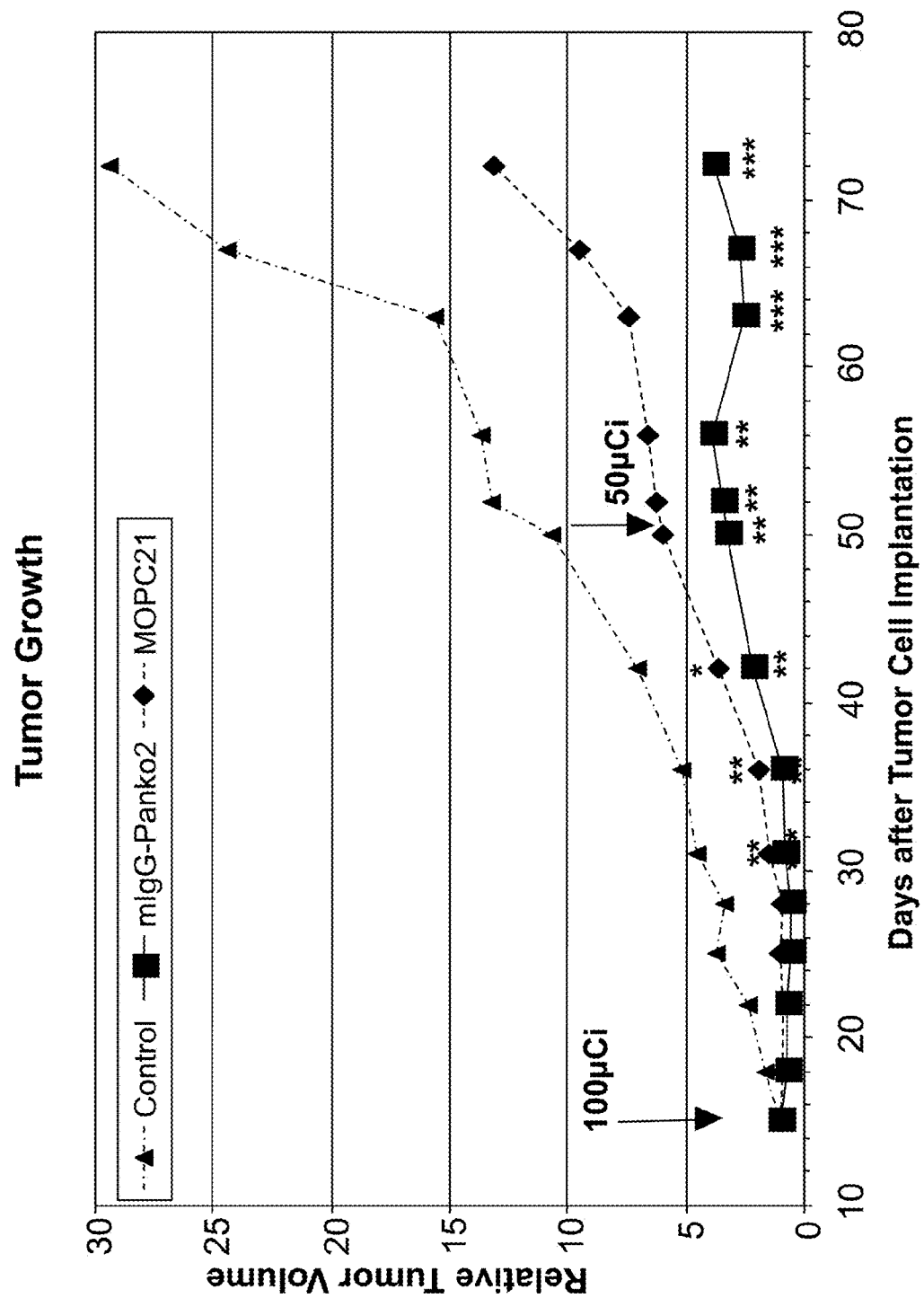
Figure 15A:
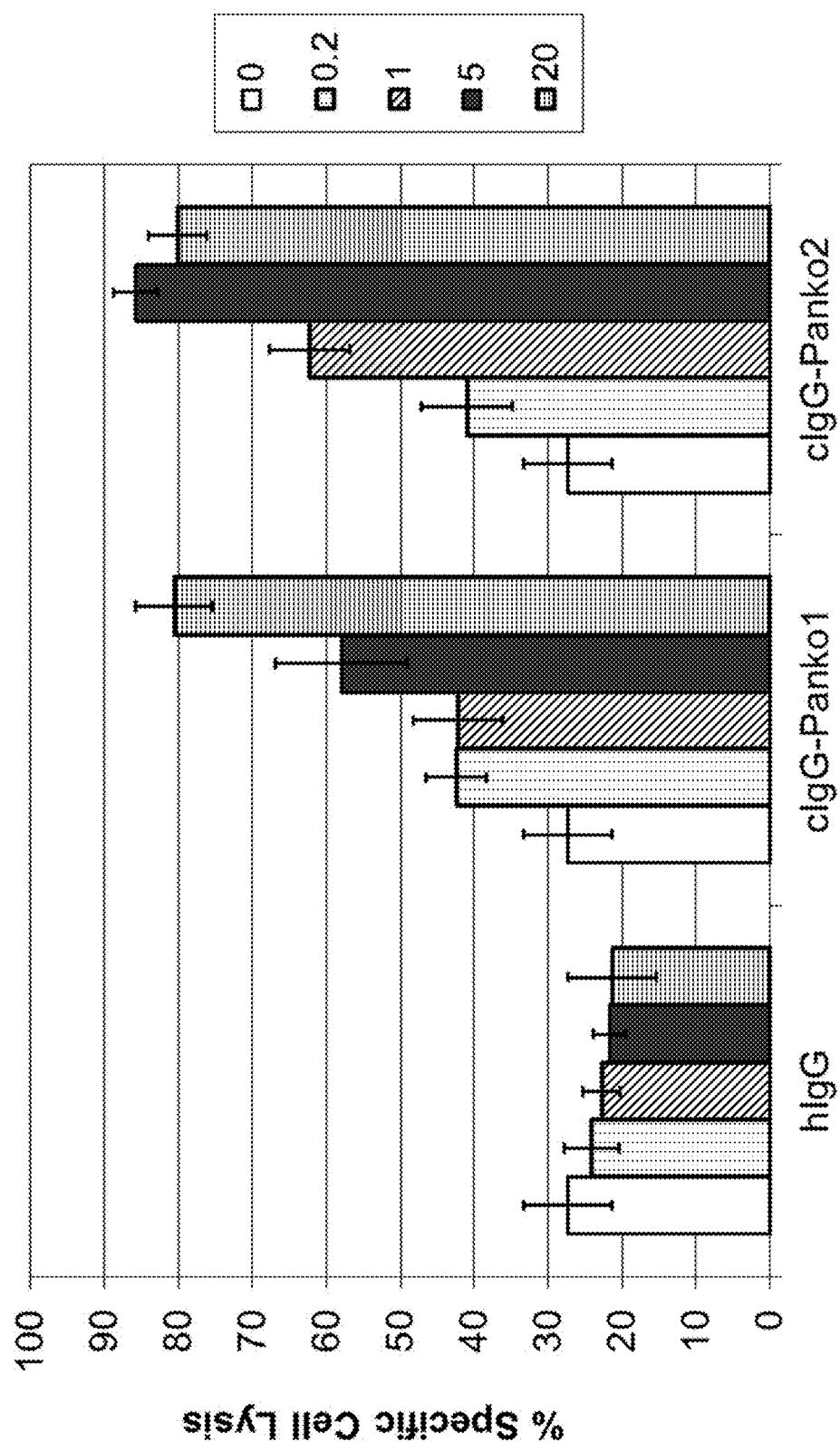
FIG. 15A-B: Specific mediation of antibody-dependent cellular cytotoxicity by the recognition molecules of the invention, Panko1 and Panko2. The antibodies were used at a concentration of 0.2 to 25 μg/ml. (a) The cIgG formats of Panko1 and Panko2 show high specific lysis of the MUC1-positive ZR-75-1 cells. (b) The mIgG Panko2 also mediates specific tumor cell lysis and shows a significantly greater effect than the murine anti-MUC1 antibody HMFG-1, with slight lysis being observed only at the highest tested concentration (25 μg/ml) for the latter.
Figure 15B:
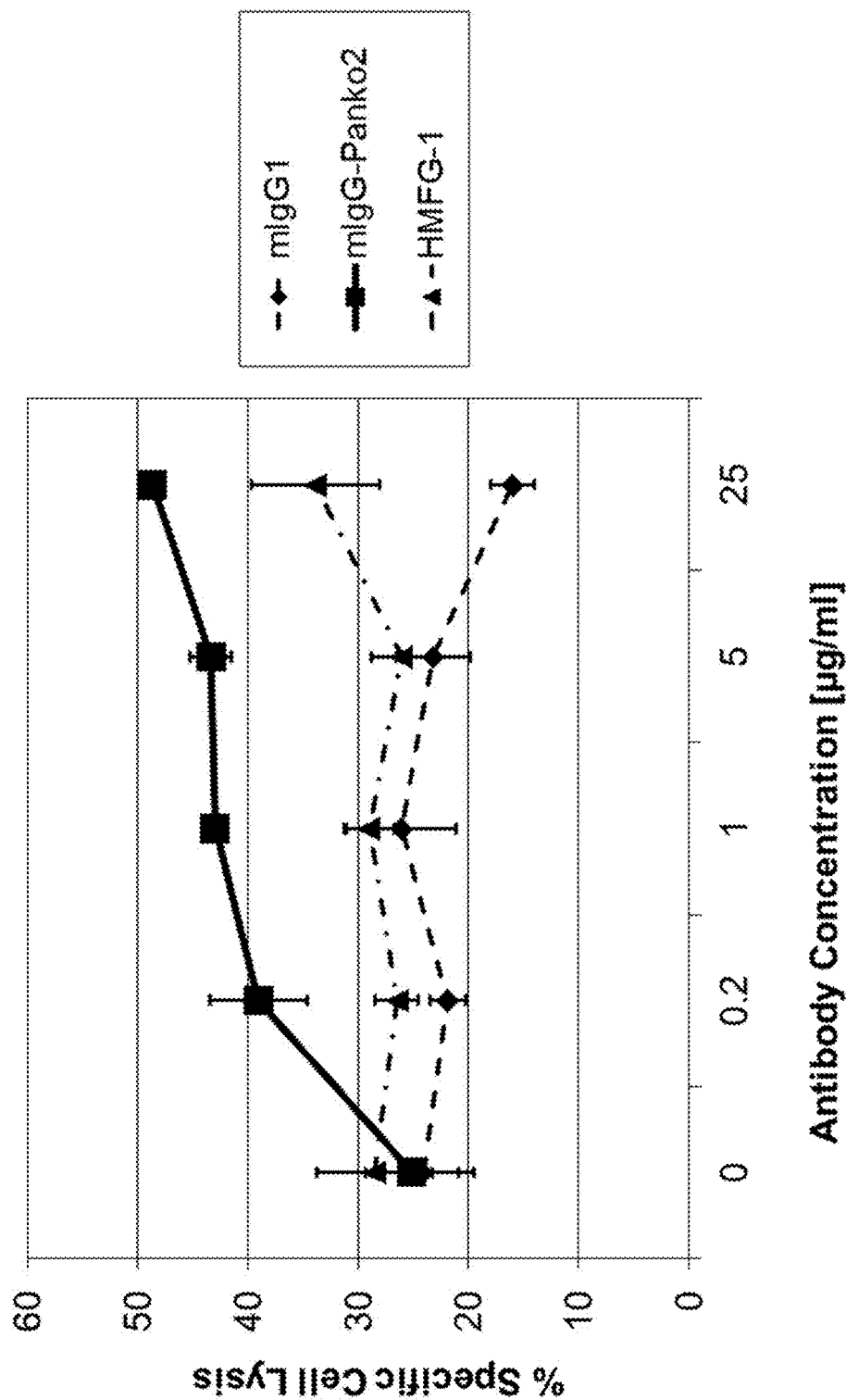
Figure 16:
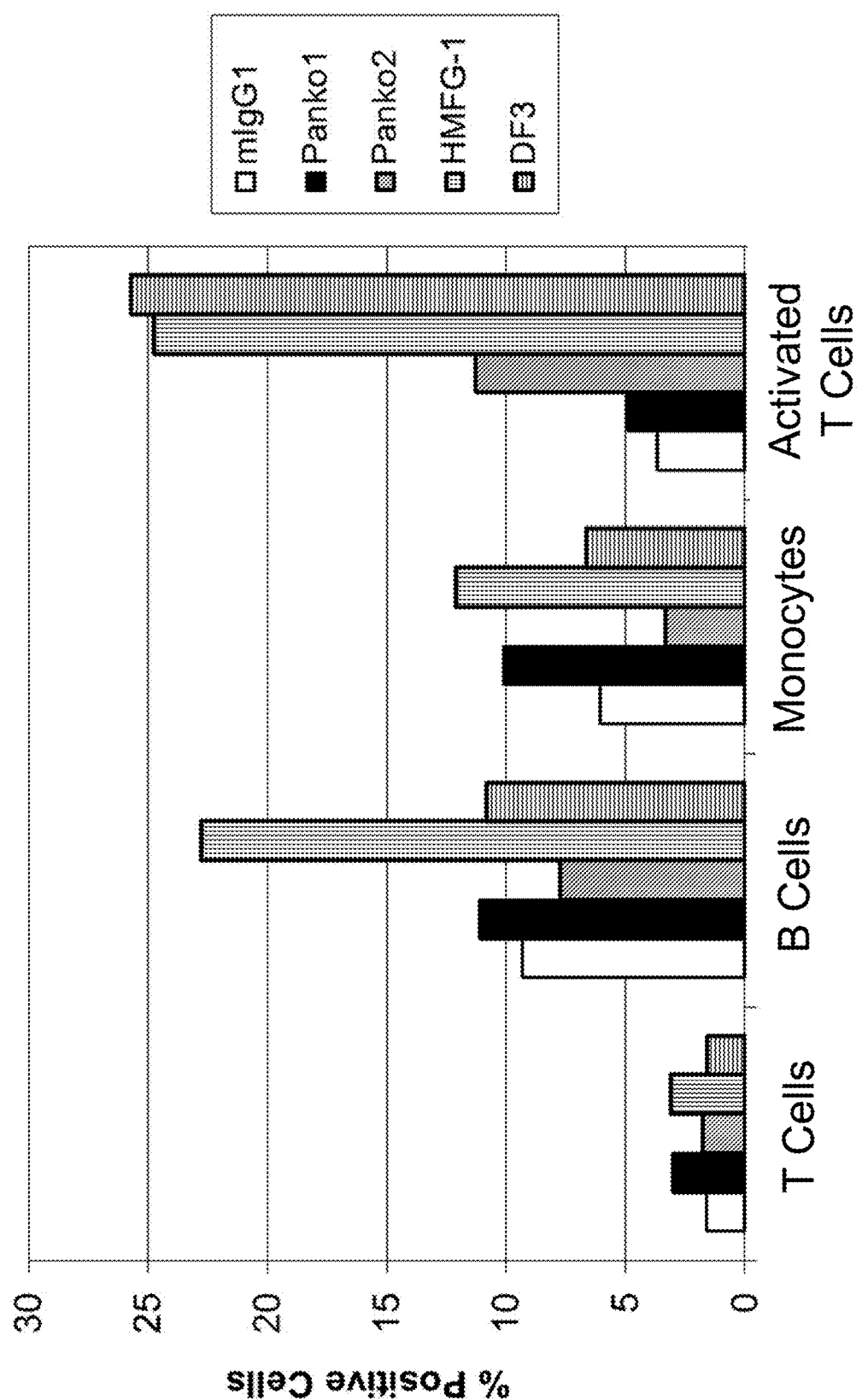
FIG. 16: Analysis of binding of recognition molecules of the invention to human blood cells. Human peripheral blood cells were obtained from the blood of healthy donors by means of density centrifugation. To stimulate human T cells, the isolated blood cells were incubated in RPMI/FCS+1 μg/ml PHA+60 U/ml hIL-2 in an incubator for 3 to 8 days. The isolated blood cells were incubated with mIgG-Panko1, mIgG-Panko2, HMFG1, DF3 or mIgG1 (control) and stained with Cy3-conjugated goat anti-mouse Ig (Dianova) and/or with a CD marker-specific (CD3, CD14, CD19), FITC-labelled antibody. Following washing, the cells were analyzed using flow cytometry.

The recognition molecules Panko1 and Panko2 show no or only low binding to human blood cells. In contrast, the MUC1-specific antibodies HMFG-1 and DF3 bind strongly to PHA-stimulated T cells, and HMFG-1 also binds to B cells and monocytes.

REFERENCES

Boel E. et al., J. Immunol. Methods 239, 153-66 (2000).
Brechbiel M. W. et al., Inorg. Chem. 25, 2772-2781 (1986).
Chothia C. et al., Science 233, 755-758 (1986).
Chothia C. et al., Nature 342, 877-883 (1989).
Chothia C. et al., J. Mol. Biol. 227, 799-817 (1992).
Chothia C. & Lesk A. M., J. Mol. Biol. 196, 901-917 (1987).
Dai J. et al., Tumor Biol. 19 (suppl. 1), 100-110 (1998).
Herrera A. M. et al., Biochem. Biophys. Res. Com. 273, 557-559 (2000).
Hinoda Y. et al. Gastroenterol. Jpn. 27, 390-395 (1992).
Jensen K. B. et al., Biochem. Biophys. Res. Com. 298, 566-573 (2002).
Kozak R. W. et al., Cancer Res. 49, 2639-2644 (1989).
Liao et al., Biotechnol. Bioeng. 73, 313-323 (2000).
Martin A. C. R. & Thornton J. M., J. Mol. Biol. 263, 800-815 (1996).
Nuttall S. D. et al., Proteins 36, 217-227 (1999).
Nygren P. A. & Uhlen M., Cur. Opin. Struc. Biol. 7, 463-469 (1997).
Rooman M. J. et al., Protein Eng. 3, 23-27 (1989).
Skerra A., J. Mol. Recog. 13, 167-187 (2000).
Stimmel J. B. et al., Bioconjug. Chem. 6, 219-225 (1995).
Tonye Libyh M. et al., Blood 90(10), 3978-83 (1997).
U.S. Pat. No. 5,506,343
U.S. Pat. No. 5,683,674
U.S. Pat. No. 5,804,187
U.S. Pat. No. 6,315,997
WO 02/44217
WO 93/20841
Wu S. & Cygler M., J. Mol. Biol. 229, 597-601 (1993).

DESCRIPTION OF SEQUENCES

| CDR sequences | |
|---|---|
| SEQ ID NO. 1 | DAWMD |
| SEQ ID NO. 2 | NYWMN |
| SEQ ID NO. 3 | EIRSKANNHATYYAESVKG |
| SEQ ID NO. 4 | EIRLKSNNYTTHYAESVKG |
| SEQ ID NO. 5 | GGYGFDY |
| SEQ ID NO. 6 | HYYFDY |
| SEQ ID NO. 7 | RSSQSIVHSNGNTYLE |
| SEQ ID NO. 8 | RSSKSLLHSNGITYFF |
| SEQ ID NO. 9 | KVSNRFS |
| SEQ ID NO. 10 | QMSNLAS |
| SEQ ID NO. 11 | FQGSHVPLT |
| SEQ ID NO. 12 | AQNLELPPT |
| CDR sequences (canonical structure variants) | |
| SEQ ID NO. 13 | NYWVN |
| SEQ ID NO. 14 | NYWIN |
| SEQ ID NO. 15 | NYWYN |
| SEQ ID NO. 16 | NYWWN |
| SEQ ID NO. 17 | DAWID |
| SEQ ID NO. 18 | DAWVD |
| SEQ ID NO. 19 | DAWYD |
| SEQ ID NO. 20 | DAWWD |
| SEQ ID NO. 21 | EIRSKANNYATYYAESVKG |
| SEQ ID NO. 22 | EIRLKSNKYTTHYAESVKG |
| SEQ ID NO. 23 | EIRLKSNSYTTHYAESVKG |
| SEQ ID NO. 24 | RPSQSIVHSNGNTYLE |
| SEQ ID NO. 25 | RSSQSIVHSNGNTYFE |

| SEQ ID NO. 26 | RPSQSIVHSNGNTYFE |
| SEQ ID NO. 27 | RPSKSLLHSNGITYFF |
| SEQ ID NO. 28 | RSSKSLLHSNGITYLF |
| SEQ ID NO. 29 | RPSKSLLHSNGITYLF |
| SEQ ID NO. 30 | FQGSHPPLT |
| SEQ ID NO. 31 | AQNLEPPPT | variable heavy chains

SEQ ID NO. 32
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSS

SEQ ID NO. 33
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSS variable light chains SEQ ID NO. 34
DIVLTQTPLSLPVSLGDQASISCRSSQSIVHSNGNTYLEWYLQKPGQSPK
LLIYKVSNRFSGVPDRFSGSGSGTDFTLKISRVEAEDLGVYYCFQGSHVP
LTFGDGTKLELKRA SEQ ID NO. 35
DIVMTQAAFSNPVTLGTSASISCRSSKSLLHSNGITYFFWYLQKPGLSPQ
LLIYQMSNLASGVPDRFSSSGSGTDFTLRISRVEAEDVGVYYCAQNLELP
PTFGGGTKLEIKRA $V_H/V_L$ pairs

| Panko1 | SEQ ID NO. 32 |
|        | SEQ ID NO. 34 |
| Panko2 | SEQ ID NO. 33 |
|        | SEQ ID NO. 35 | various single chain Fv formats

SEQ ID NO. 36
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSGGGGSGGGGSGGGGSGGSDIVLTQTPLSLPVS
LGDQASISCRSSQSIVHSNGNTYLEWYLQKPGQSPKLLIYKVSNRFSGVP
DRFSGSGSGTDFTLKISRVEAEDLGVYYCFQGSHVPLTFGDGTKLELKRA
AAHHHHHGAAEQKLISEEDLNGAA

SEQ ID NO. 37
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSASSGGGSADIVLTQTPLSLPVSLGDQASISC
RSSQSIVHSNGNTYLEWYLQKPGQSPKLLIYKVSNRFSGVPDRFSGSGSG
TDFTLKISRVEAEDLGVYYCFQGSHVPLTFGDGTKLELKRAAAHHHHHG
AAEQKLISEEDLNGAA

SEQ ID NO. 38
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSASSGGSADIVLTQTPLSLPVSLGDQASISCR
SSQSIVHSNGNTYLEWYLQKPGQSPKLLIYKVSNRFSGVPDRFSGSGSGT
DFTLKISRVEAEDLGVYYCFQGSHVPLTFGDGTKLELKRAAAHHHHHGA
AEQKLISEEDLNGAA

SEQ ID NO. 39
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSASSGSSADIVLTQTPLSLPVSLGDQASISCRS
SQSIVHSNGNTYLEWYLQKPGQSPKLLIYKVSNRFSGVPDRFSGSGSGTD
FTLKISRVEAEDLGVYYCFQGSHVPLTFGDGTKLELKRAAAHHHHHGAA
EQKLISEEDLNGAA

SEQ ID NO. 40
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSASSSSADIVLTQTPLSLPVSLGDQASISCRSS
QSIVHSNGNTYLEWYLQKPGQSPKLLIYKVSNRFSGVPDRFSGSGSGTDF
TLKISRVEAEDLGVYYCFQGSHVPLTFGDGTKLELKRAAAHHHHHGAAE
QKLISEEDLNGAA

SEQ ID NO. 41
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSASSSADIVLTQTPLSLPVSLGDQASISCRSSQ
SIVHSNGNTYLEWYLQKPGQSPKLLIYKVSNRFSGVPDRFSGSGSGTDFT
LKISRVEAEDLGVYYCFQGSHVPLTFGDGTKLELKRAAAHHHHHGAAEQ
KLISEEDLNGAA

SEQ ID NO. 42
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSASSADIVLTQTPLSLPVSLGDQASISCRSSQS
IVHSNGNTYLEWYLQKPGQSPKLLIYKVSNRFSGVPDRFSGSGSGTDFTL
KISRVEAEDLGVYYCFQGSHVPLTFGDGTKLELKRAAAHHHHHGAAEQK
LISEEDLNGAA

SEQ ID NO. 43
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSASADIVLTQTPLSLPVSLGDQASISCRSSQSI
VHSNGNTYLEWYLQKPGQSPKLLIYKVSNRFSGVPDRFSGSGSGTDFTLK
ISRVEAEDLGVYYCFQGSHVPLTFGDGTKLELKRAAAHHHHHGAAEQKL
ISEEDLNGAA

SEQ ID NO. 44
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSAADIVLTQTPLSLPVSLGDQASISCRSSQSIV
HSNGNTYLEWYLQKPGQSPKLLIYKVSNRFSGVPDRFSGSGSGTDFTLKI
SRVEAEDLGVYYCFQGSHVPLTFGDGTKLELKRAAAHHHHHGAAEQKLI
SEEDLNGAA

SEQ ID NO. 45
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSADIVLTQTPLSLPVSLGDQASISCRSSQSIVH
SNGNTYLEWYLQKPGQSPKLLIYKVSNRFSGVPDRFSGSGSGTDFTLKIS
RVEAEDLGVYYCFQGSHVPLTFGDGTKLELKRAAAHHHHHGAAEQKLIS
EEVHQ

SEQ ID NO. 46
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSSDIVLTQTPLSLPVSLGDQASISCRSSQSIVHS
NGNTYLEWYLQKPGQSPKLLIYKVSNRFSGVPDRFSGSGSGTDFTLKISR
VEAEDLGVYYCFQGSHVPLTFGDGTKLELKRAAAHHHHHGAAEQKLISE
EDLNGAA

SEQ ID NO. 47
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSDIVLTQTPLSLPVSLGDQASISCRSSQSIVHSN
GNTYLEWYLQKPGQSPKLLIYKVSNRFSGVPDRFSGSGSGTDFTLKISRV
EAEDLGVYYCFQGSHVPLTFGDGTKLELKRAAAHHHHHGAAEQKLISEE
DLNGAA

SEQ ID NO. 48
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSASSGGGGSGGGGSGGSARDIVMTQAAFSNPVTL
GTSASISCRSSKSLLHSNGITYFFWYLQKPGLSPQLLIYQMSNLASGVPD
RFSSSGSGTDFTLRISRVEAEDVGVYYCAQNLELPPTFGGGTKLEIKRAA
AHHHHHGAAEQKLISEEDLNGAA

SEQ ID NO. 49
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSASSGSGSSADIVMTQAAFSNPVTLGTSASISCR
SSKSLLHSNGITYFFWYLQKPGLSPQLLIYQMSNLASGVPDRFSSSGSGT

-continued

DFTLRISRVEAEDVGVYYCAQNLELPPTFGGGTKLEIKRAAAHHHHHGA
AEQKLISEEDLNGAA

SEQ ID NO. 50
EVKLVESGGGLVQPGGSMKLSCVASGFTFSNYWMNWVRQSPEKGLEWVA
EIRLKSNNYTTHYAESVKGRFTISRDDSKSSVSLQMNNLRVEDTGIYYCTR
HYYFDYWGQGTTLTVSSASSGGSSADIVMTQAAFSNPVTLGTSASISCRS
SKSLLHSNGITYFFWYLQKPGLSPQLLIYQMSNLASGVPDRFSSSGSGTD
FTLRISRVEAEDVGVYYCAQNLELPPTFGGGTKLEIKRAAAHHHHHGAA
EQKLISEEDLNGAA

SEQ ID NO. 51
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSASSGSSADIVMTQAAFSNPVTLGTSASISCRSS
KSLLHSNGITYFFWYLQKPGLSPQLLIYQMSNLASGVPDRFSSSGSGTDF
TLRISRVEAEDVGVYYCAQNLELPPTFGGGTKLEIKRAAAHHHHHGAAE
QKLISEEDLNGAA

SEQ ID NO. 52
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSASSSSADIVMTQAAFSNPVTLGTSASISCRSSK
SLLHSNGITYFFWYLQKPGLSPQLLIYQMSNLASGVPDRFSSSGSGTDFT
LRISRVEAEDVGVYYCAQNLELPPTFGGGTKLEIKRAAAHHHHHGAAEQ
KLISEEDLNGAA

SEQ ID NO. 53
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSASSSADIVMTQAAFSNPVTLGTSASISCRSSKS
LLHSNGITYFFWYLQKPGLSPQLLIYQMSNLASGVPDRFSSSGSGTDFTL
RISRVEAEDVGVYYCAQNLELPPTFGGGTKLEIKRAAAHHHHHGAAEQK
LISEEDLNGAA

SEQ ID NO. 54
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSASSADIVMTQAAFSNPVTLGTSASISCRSSKSL
LHSNGITYFFWYLQKPGLSPQLLIYQMSNLASGVPDRFSSSGSGTDFTLR
ISRVEAEDVGVYYCAQNLELPPTFGGGTKLEIKRAAAHHHHHGAAEQKL
ISEEDLNGAA

SEQ ID NO. 55
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSASADIVMTQAAFSNPVTLGTSASISCRSSKSLL
HSNGITYFFWYLQKPGLSPQLLIYQMSNLASGVPDRFSSSGSGTDFTLRI
SRVEAEDVGVYYCAQNLELPPTFGGGTKLEIKRAAAHHHHHGAAEQKLI
SEEDLNGAA

SEQ ID NO. 56
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSAADIVMTQAAFSNPVTLGTSASISCRSSKSLLH
SNGITYFFWYLQKPGLSPQLLIYQMSNLASGVPDRFSSSGSGTDFTLRIS
RVEAEDVGVYYCAQNLELPPTFGGGTKLEIKRAAAHHHHHGAAEQKLIS
EEDLNGAA

SEQ ID NO. 57
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSADIVMTQAAFSNPVTLGTSASISCRSSKSLLHS
NGITYFFWYLQKPGLSPQLLIYQMSNLASGVPDRFSSSGSGTDFTLRISR
VEAEDVGVYYCAQNLELPPTFGGGTKLEIKRAAAHHHHHGAAEQKLISE
EDLNGAA

SEQ ID NO. 58
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSSDIVMTQAAFSNPVTLGTSASISCRSSKSLLHSN
GITYFFWYLQKPGLSPQLLIYQMSNLASGVPDRFSSSGSGTDFTLRISRV
EAEDVGVYYCAQNLELPPTFGGGTKLEIKRAAAHHHHHGAAEQKLISEE
DLNGAA

SEQ ID NO. 59
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSDIVMTQAAFSNPVTLGTSASISCRSSKSLLHSNG

-continued

ITYFFWYLQKPGLSPQLLIYQMSNLASGVPDRFSSSGSGTDFTLRISRVE
AEDVGVYYCAQNLELPPTFGGGTKLEIKRAAAHHHHHGAAEQKLISEED
LNGAA

Murine Antibodies light chain of a murine IgG1 (kappa chain)

SEQ ID NO. 60
DIVLTQTPLSLPVSLGDQASISCRSSQSIVHSNGNTYLEWYLQKPGQSPK
LLIYKVSNRFSGVPDRFSGSGSGTDFTLKISRVEAEDLGVYYCFQGSHVP
LTFGDGTKLELKRADAAPTVSIFPPSSEQLTSGGASVVCFLNNFYPKDIN
VKWKIDGSERQNGVLNSWTDQDSKDSTYSMSSTLTLTKDEYERHNSYTCE
ATHKTSTSPIVKSFNRNEC

SEQ ID NO. 61
DIVMTQAAFSNPVTLGTSASISCRSSKSLLHSNGITYFFWYLQKPGLSPQ
LLIYQMSNLASGVPDRFSSSGSGTDFTLRISRVEAEDVGVYYCAQNLELP
PTFGGGTKLEIKRADAAPTVSIFPPSSEQLTSGGASVVCFLNNFYPKDIN
VKWKIDGSERQNGVLNSWTDQDSKDSTYSMSSTLTLTKDEYERHNSYTCE
ATHKTSTSPIVKSFNRNEC heavy chain of murine IgG1

SEQ ID NO. 62
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSAKTTPPSVYPLAPGSAAQTNSMVTLGCLVKGYF
PEPVTVTWNSGSLSSGVHTFPAVLESDLYTLSSSVTVPSSPRPSETVTCN
VAHPASSTKVDKKIVPRDCGCKPCICTVPEVSSVFIFPPKPKDVLTITLT
PKVTCVVVDISKDDPEVQFSWFVDDVEVHTAQTQPREEQFNSTFRSVSEL
PIMHQDWLNGKEFKCRVNSAAFPAPIEKTISKTKGRPKAPQVYTIPPPKE
QMAKDKVSLTCMITDFFPEDITVEWQWNGQPAENYKNTQPIMNTNGSYFV
YSKLNVQKSNWEAGNTFTCSVLHEGLHNHHTEKSLSHSPGK

SEQ ID NO. 63
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSAKTTPPSVYPLAPGSAAQTNSMVTLGCLVKGYFP
EPVTVTWNSGSLSSGVHTFPAVLESDLYTLSSSVTVPSSPRPSETVTCNV
AHPASSTKVDKKIVPRDCGCKPCICTVPEVSSVFIFPPKPKDVLTITLTP
KVTCVVVDISKDDPEVQFSWFVDDVEVHTAQTQPREEQFNSTFRSVSELP
IMHQDWLNGKEFKCRVNSAAFPAPIEKTISKTKGRPKAPQVYTIPPPKEQ
MAKDKVSLTCMITDFFPEDITVEWQWNGQPAENYKNTQPIMNTNGSYFVY
SKLNVQKSNWEAGNTFTCSVLHEGLHNHHTEKSLSHSPGK murine antibodies

| | |
|---|---|
| mIgG-Panko1 | SEQ ID NO. 60 |
| | SEQ ID NO. 62 |
| mIgG-Panko2 | SEQ ID NO. 61 |
| | SEQ ID NO. 63 |

Chimeric antibodies (mouse/human)

heavy chain of chimeric IgG1 (gamma chain)

SEQ ID NO. 64
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSGSTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

SEQ ID NO. 65
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSGSTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK

-continued heavy chain of a chimeric IgM (μ chain)

SEQ ID NO. 66
EVKLVESGGGLVQPGGSMKLSCAASGFTFSDAWMDWVRQSPEKGLEWVAE
IRSKANNHATYYAESVKGRFTISRDVSKSSVYLQMNNLRAEDTGIYYCTR
GGYGFDYWGQGTTLTVSGSASAPTLFPLVSCENSPSDTSSVAVGCLAQDF
LPDSITLSWKYKNNSDISSTRGFPSVLRGGKYAATSQVLLPSKDVMQGTD
EHVVCKVQHPNGNKEKNVPLPVIAELPPKVSVFVPPRDGFFGNPRKSKLI
CQATGFSPRQIQVSWLREGKQVGSGVTTDQVQAEAKESGPTTYKVTSTLT
IKESDWLGQSMFTCRVDHRGLTFQQNASSMCVPDQDTAIRVFAIPPSFAS
IFLTKSTKLTCLVTDLTTYDSVTISWTRQNGEAVKTHTNISESHPNATFS
AVGEASICEDDWNSGERFTCTVTHTDLPSPLKQTISRPKGVALHRPDVYL
LPPAREQLNLRESATITCLVTGFSPADVFVQWMQRGQPLSPEKYVTSAPM
PEPQAPGRYFAHSILTVSEEEWNTGETYTCVVAHEALPNRVTERTVDKST
GKPTLYNVSLVMSDTAGTCY

SEQ ID NO. 67
EVKLVESGGGLVQPGGSMKLSCVASGFTFSNYWMNWVRQSPEKGLEWVAE
IRLKSNNYTTHYAESVKGRFTISRDDSKSSVSLQMNNLRVEDTGIYYCTR
HYYFDYWGQGTTLTVSGSASAPTLFPLVSCENSPSDTSSVAVGCLAQDFL
PDSITLSWKYKNNSDISSTRGFPSVLRGGKYAATSQVLLPSKDVMQGTDE
HVVCKVQHPNGNKEKNVPLPVIAELPPKVSVFVPPRDGFFGNPRKSKLIC
QATGFSPRQIQVSWLREGKQVGSGVTTDQVQAEAKESGPTTYKVTSTLTI
KESDWLGQSMFTCRVDHRGLTFQQNASSMCVPDQDTAIRVFAIPPSFASI
FLTKSTKLTCLVTDLTTYDSVTISWTRQNEAVKTHTNISESHPNATFSA
VGEASICEDDWNSGERFTCTVTHTDLPSPLKQTISRPKGVALHRPDVYLL
PPAREQLNLRESATITCLVTGFSPADVFVQWMQRGQPLSPEKYVTSAPMP

-continued

EPQAPGRYFAHSILTVSEEEWNTGETYTCVVAHEALPNRVTERTVDKSTG
KPTLYNVSLVMSDTAGTCY light chain of a chimeric IgG1 or IgM (kappa chain)

SEQ ID NO. 68
DIVLTQTPLSLPVSLGDQASISCRSSQSIVHSNGNTYLEWYLQKPGQSPK
LLIYKVSNRFSGVPDRFSGSGSGTDFTLKISRVEAEDLGVYYCFQGSHVP
LTFGDGTKLELKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

SEQ ID NO. 69
DIVMTQAAFSNPVTLGTSASISCRSSKSLLHSNGITYFFWYLQKPGLSPQ
LLIYQMSNLASGVPDRFSSSGSGTDFTLRISRVEAEDVGVYYCAQNLELP
PTFGGGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

| chimeric antibodies | |
|---|---|
| cIgG-Panko1 | SEQ ID NO. 64 |
| | SEQ ID NO. 68 |
| cIgG-Panko2 | SEQ ID NO. 65 |
| | SEQ ID NO. 69 |
| cIgM-Panko1 | SEQ ID NO. 66 |
| | SEQ ID NO. 68 |
| cIgM-Panko1 | SEQ ID NO. 67 |
| | SEQ ID NO. 69 |

The invention claimed is:
1. A method of providing a molecule for tumor recognition comprising,
   a. providing a recombinant recognition molecule which comprises a variable heavy chain and a variable light chain and which specifically binds to a glycosylated MUC1 tumor epitope, wherein
   the variable heavy chain comprises (i) a CDRH1 region that comprises the amino acid sequence of SEQ ID NO: 1 or 2; (ii) a CDRH2 region that comprises the amino acid sequence of SEQ ID NO: 3 or 4; and (iii) a CDRH3 region that comprises the amino acid sequence of SEQ ID NO: 5 or 6; and
   the variable light chain comprises (i) a CDRL1 region that comprises the amino acid sequence of SEQ ID NO: 7 or 8; (ii) a CDRL2 region that comprises the amino acid sequence of SEQ ID NO: 9 or 10; and (iii) a CDRL3 region that comprises the amino acid sequence of SEQ ID NO: 11 or 12;
   b. modifying the recombinant recognition molecule by one or more mutations in one or more amino acid sequences set forth in step a., wherein single amino acids are replaced by amino acids having analogous physicochemical properties,
   c. selecting a recombinant recognition molecule modified in step b. that retains binding specificity towards the glycosylated MUC1 tumor epitope, and
   d. providing the modified recombinant recognition molecule selected in step c.

2. The method of claim 1, wherein the modification is a replacement by an equivalent canonical structure.

3. The method of claim 1, wherein the modified recombinant recognition molecule comprises a CDRH1 region variant comprising I, Y, W, or V substituted for M at position 4 of SEQ ID NO:1 or 2.

4. The method of claim 1, wherein the modified recombinant recognition molecule comprises a CDRH2 region variant selected from (a) a variant that has K or S substituted for N at position 8 of SEQ ID NO: 4; and (b) a variant that has Y substituted for H at position 9 of SEQ ID NO: 3.

5. The method of claim 1, wherein the modified recombinant recognition molecule comprises a CDRL1 region variant selected from (a) a variant that has P substituted for S at position 2 of SEQ ID NO: 7 or 8; (b) a variant that has F substituted for L at position 15 of SEQ ID NO: 7; and (c) a variant that has L substituted for F at position 15 of SEQ ID NO: 8.

6. The method of claim 1, wherein the modified recombinant recognition molecule comprises a CDRL3 region variant selected from (a) a variant that has P substituted for V at position 6 of SEQ ID NO: 11; and (b) a variant that has P substituted for L at position 6 of SEQ ID NO: 12.

7. The method of claim 1, wherein the recombinant recognition molecule comprises:
   (a) an FRH1 region comprising the following sequence, wherein the amino acid position corresponds to the numbering according to Kabat,

| | |
|---|---|
| 1 | E |
| 2 | V |
| 3 | K |
| 4 | L |
| 5 | V |
| 6 | E |
| 7 | S |
| 8 | G |
| 9 | G |
| 10 | G |
| 11 | L |
| 12 | V |
| 13 | Q |
| 14 | P |
| 15 | G |
| 16 | G |
| 17 | S |
| 18 | M |
| 19 | K |
| 20 | L |
| 21 | S |
| 22 | C |
| 23 | A or V |
| 24 | A, V, S or T |
| 25 | S |
| 26 | G |
| 27 | Y, F, S or D |
| 28 | T |
| 29 | F, L or I |
| 30 | S; |

(b) an FRH2 region comprising the following sequence, wherein the amino acid position corresponds to the numbering according to Kabat,

| | |
|---|---|
| 36 | W |
| 37 | V |
| 38 | R |
| 39 | Q |
| 40 | S |
| 41 | P |
| 42 | E |
| 43 | K |
| 44 | G |
| 45 | L |
| 46 | E |
| 47 | W |
| 48 | V |
| 49 | A; |

(c) an FRH3 region comprising the following sequence, wherein the amino acid position corresponds to the numbering according to Kabat,

| | |
|---|---|
| 66 | R |
| 67 | F |
| 68 | T |
| 69 | I |
| 70 | S |
| 71 | R |
| 72 | D |
| 73 | D or V |
| 74 | S |
| 75 | K |
| 76 | S |
| 77 | S |
| 78 | V |
| 79 | Y or S |
| 80 | L |
| 81 | Q |
| 82 | M |
| 82a | N |
| 82b | N |
| 82c | L |
| 83 | R |
| 84 | A or V |
| 85 | E |
| 86 | D |
| 87 | T |
| 88 | G |
| 89 | I |
| 90 | Y |

| | |
|---|---|
| 91 | Y |
| 92 | C |
| 93 | T |
| 94 | R, G, N, K or S. |

(d) an FRH4 region comprising the following sequence, wherein the amino acid position corresponds to the numbering according to Kabat,

| | |
|---|---|
| 103 | W |
| 104 | G |
| 105 | Q |
| 106 | G |
| 107 | T |
| 108 | T |
| 109 | L |
| 110 | T |
| 111 | V |
| 112 | S |
| 113 | S or A; |

(e) an FRL1 region comprising the following sequence, wherein the amino acid position corresponds to the numbering according to Kabat,

| | |
|---|---|
| 1 | D |
| 2 | I, V or L |
| 3 | V |
| 4 | M or L |
| 5 | T |
| 6 | Q |
| 7 | T or A |
| 8 | P or A |
| 9 | L or F |
| 10 | S |
| 11 | L or N |
| 12 | P |
| 13 | V |
| 14 | S or T |
| 15 | L |
| 16 | G |
| 17 | D or T |
| 18 | Q or S |
| 19 | A |
| 20 | S |
| 21 | I |
| 22 | S |
| 23 | C; |

(f) an FRL2 region comprising the following sequence, wherein the amino acid position corresponds to the numbering according to Kabat,

| | |
|---|---|
| 35 | W |
| 36 | Y |
| 37 | L |
| 38 | Q |
| 39 | K |
| 40 | P |
| 41 | G |
| 42 | Q or L |
| 43 | S |
| 44 | P |
| 45 | K or Q |
| 46 | L |
| 47 | L |
| 48 | I or V |
| 49 | Y; |

(g) an FRL3 region comprising the following sequence, wherein the amino acid position corresponds to the numbering according to Kabat,

| | |
|---|---|
| 57 | G |
| 58 | V |
| 59 | P |
| 60 | D |
| 61 | R |
| 62 | F |
| 63 | S |
| 64 | G or S |
| 65 | S |
| 66 | G |
| 67 | S |
| 68 | G |
| 69 | T |
| 70 | D |
| 71 | F |
| 72 | T |
| 73 | L |
| 74 | K or R |
| 75 | I |
| 76 | S |
| 77 | R |
| 78 | V |
| 79 | E |
| 80 | A |
| 81 | E |
| 82 | D |
| 83 | L or V |
| 84 | G |
| 85 | V |
| 86 | Y |
| 87 | Y |
| 88 | C; or |

(h) an FRL4 region comprising the following sequence, wherein the amino acid position to the numbering according to Kabat,

| | |
|---|---|
| 98 | F |
| 99 | G |
| 100 | G or D |
| 101 | G |
| 102 | T |
| 103 | K |
| 104 | L |
| 105 | E |
| 106 | I or L |
| 106a | K |
| 107 | R |
| 108 | A. |

\* \* \* \* \*

SEQUENCE LISTING

<160> NUMBER OF SEQ ID NOS: 84

<210> SEQ ID NO 1
<211> LENGTH: 5
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 1

Asp Ala Trp Met Asp
1               5

<210> SEQ ID NO 2
<211> LENGTH: 5
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 2

Asn Tyr Trp Met Asn
1               5

<210> SEQ ID NO 3
<211> LENGTH: 19
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 3

Glu Ile Arg Ser Lys Ala Asn Asn His Ala Thr Tyr Tyr Ala Glu Ser
1               5                   10                  15

Val Lys Gly

```
<210> SEQ ID NO 4
<211> LENGTH: 19
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 4

Glu Ile Arg Leu Lys Ser Asn Asn Tyr Thr Thr His Tyr Ala Glu Ser
1               5                   10                  15

Val Lys Gly

<210> SEQ ID NO 5
<211> LENGTH: 7
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 5

Gly Gly Tyr Gly Phe Asp Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 6

His Tyr Tyr Phe Asp Tyr
1               5

<210> SEQ ID NO 7
<211> LENGTH: 16
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 7

Arg Ser Ser Gln Ser Ile Val His Ser Asn Gly Asn Thr Tyr Leu Glu
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 8

Arg Ser Ser Lys Ser Leu Leu His Ser Asn Gly Ile Thr Tyr Phe Phe
1               5                   10                  15

<210> SEQ ID NO 9
<211> LENGTH: 7
<212> TYPE: PRT
<213> ORGANISM: Artificial Sequence
<220> FEATURE:
```

```
<223> OTHER INFORMATION: Recognition sequence that specifically bind to
      glycosylated MUC1 tumor epitiope

<400> SEQUENCE: 9

Lys Val Ser Asn Arg Phe Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 10

Gln Met Ser Asn Leu Ala Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 11

Phe Gln Gly Ser His Val Pro Leu Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Recognition sequence that specifically bind to
      glycosylated MUC1 tumor epitiope

<400> SEQUENCE: 12

Ala Gln Asn Leu Glu Leu Pro Pro Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Canonical structure variant CDR sequence

<400> SEQUENCE: 13

Asn Tyr Trp Val Asn
1               5

<210> SEQ ID NO 14
<211> LENGTH: 5
<212> TYPE: PRT
<213> ORGANISM: Artificial Sequence
<220> FEATURE:
<223> OTHER INFORMATION: Canonical structure variant CDR sequence

<400> SEQUENCE: 14

Asn Tyr Trp Ile Asn
1               5

<210> SEQ ID NO 15
<211> LENGTH: 5
```

```
<212> TYPE: PRT
<213> ORGANISM: Artificial Sequence
<220> FEATURE:
<223> OTHER INFORMATION: Canonical structure variant CDR sequence

<400> SEQUENCE: 15

Asn Tyr Trp Tyr Asn
 1               5

<210> SEQ ID NO 16
<211> LENGTH: 5
<212> TYPE: PRT
<213> ORGANISM: Artificial Sequence
<220> FEATURE:
<223> OTHER INFORMATION: Canonical structure variant CDR sequence

<400> SEQUENCE: 16

Asn Tyr Trp Trp Asn
 1               5

<210> SEQ ID NO 17
<211> LENGTH: 5
<212> TYPE: PRT
<213> ORGANISM: Artificial Sequence
<220> FEATURE:
<223> OTHER INFORMATION: Canonical structure variant CDR sequence

<400> SEQUENCE: 17

Asp Ala Trp Ile Asp
 1               5

<210> SEQ ID NO 18
<211> LENGTH: 5
<212> TYPE: PRT
<213> ORGANISM: Artificial Sequence
<220> FEATURE:
<223> OTHER INFORMATION: Canonical structure variant CDR sequence

<400> SEQUENCE: 18

Asp Ala Trp Val Asp
 1               5

<210> SEQ ID NO 19
<211> LENGTH: 5
<212> TYPE: PRT
<213> ORGANISM: Artificial Sequence
<220> FEATURE:
<223> OTHER INFORMATION: Canonical structure variant CDR sequence

<400> SEQUENCE: 19

Asp Ala Trp Tyr Asp
 1               5

<210> SEQ ID NO 20
<211> LENGTH: 5
<212> TYPE: PRT
<213> ORGANISM: Artificial Sequence
<220> FEATURE:
<223> OTHER INFORMATION: Canonical structure variant CDR sequence

<400> SEQUENCE: 20

Asp Ala Trp Trp Asp
 1               5

<210> SEQ ID NO 21
<211> LENGTH: 19
<212> TYPE: PRT
```

<213> ORGANISM: Artificial Sequence
<220> FEATURE:
<223> OTHER INFORMATION: Canonical structure variant CDR sequence

<400> SEQUENCE: 21

Glu Ile Arg Ser Lys Ala Asn Asn Tyr Ala Thr Tyr Tyr Ala Glu Ser
1               5                   10                  15
Val Lys Gly

<210> SEQ ID NO 22
<211> LENGTH: 19
<212> TYPE: PRT
<213> ORGANISM: Artificial Sequence
<220> FEATURE:
<223> OTHER INFORMATION: Canonical structure variant CDR sequence

<400> SEQUENCE: 22

Glu Ile Arg Leu Lys Ser Asn Lys Tyr Thr Thr His Tyr Ala Glu Ser
1               5                   10                  15
Val Lys Gly

<210> SEQ ID NO 23
<211> LENGTH: 19
<212> TYPE: PRT
<213> ORGANISM: Artificial Sequence
<220> FEATURE:
<223> OTHER INFORMATION: Canonical structure variant CDR sequence

<400> SEQUENCE: 23

Glu Ile Arg Leu Lys Ser Asn Ser Tyr Thr Thr His Tyr Ala Glu Ser
1               5                   10                  15
Val Lys Gly

<210> SEQ ID NO 24
<211> LENGTH: 16
<212> TYPE: PRT
<213> ORGANISM: Artificial Sequence
<220> FEATURE:
<223> OTHER INFORMATION: Canonical structure variant CDR sequence

<400> SEQUENCE: 24

Arg Pro Ser Gln Ser Ile Val His Ser Asn Gly Asn Thr Tyr Leu Glu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Canonical structure variant CDR sequence

<400> SEQUENCE: 25

Arg Ser Ser Gln Ser Ile Val His Ser Asn Gly Asn Thr Tyr Phe Glu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Canonical structure variant CDR sequence

<400> SEQUENCE: 26

Arg Pro Ser Gln Ser Ile Val His Ser Asn Gly Asn Thr Tyr Phe Glu
1               5                   10                  15

```
<210> SEQ ID NO 27
<211> LENGTH: 16
<212> TYPE: PRT
<213> ORGANISM: Artificial Sequence
<220> FEATURE:
<223> OTHER INFORMATION: Canonical structure variant CDR sequence

<400> SEQUENCE: 27

Arg Pro Ser Lys Ser Leu Leu His Ser Asn Gly Ile Thr Tyr Phe Phe
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Canonical structure variant CDR sequence

<400> SEQUENCE: 28

Arg Ser Ser Lys Ser Leu Leu His Ser Asn Gly Ile Thr Tyr Leu Phe
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Canonical structure variant CDR sequence

<400> SEQUENCE: 29

Arg Pro Ser Lys Ser Leu Leu His Ser Asn Gly Ile Thr Tyr Leu Phe
1               5                   10                  15

<210> SEQ ID NO 30
<211> LENGTH: 9
<212> TYPE: PRT
<213> ORGANISM: Artificial Sequence
<220> FEATURE:
<223> OTHER INFORMATION: Canonical structure variant CDR sequence

<400> SEQUENCE: 30

Phe Gln Gly Ser His Pro Pro Leu Thr
1               5

<210> SEQ ID NO 31
<211> LENGTH: 9
<212> TYPE: PRT
<213> ORGANISM: Artificial Sequence
<220> FEATURE:
<223> OTHER INFORMATION: Canonical structure variant CDR sequence

<400> SEQUENCE: 31

Ala Gln Asn Leu Glu Pro Pro Pro Thr
1               5

<210> SEQ ID NO 32
<211> LENGTH: 118
<212> TYPE: PRT
<213> ORGANISM: Artificial Sequence
<220> FEATURE:
<223> OTHER INFORMATION: Amino acid sequence with preferred framework
      for variable heavy chain.

<400> SEQUENCE: 32

Glu Val Lys Leu Val Glu Ser Gly Gly Gly Leu Val Gln Pro Gly Gly
1               5                   10                  15
```

```
Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
            100                 105                 110

Thr Leu Thr Val Ser Ser
        115

<210> SEQ ID NO 33
<211> LENGTH: 117
<212> TYPE: PRT
<213> ORGANISM: Artificial Sequence
<220> FEATURE:
<223> OTHER INFORMATION: Amino acid sequence with preferred framework
      for variable heavy chain.

<400> SEQUENCE: 33

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Ser
        115

<210> SEQ ID NO 34
<211> LENGTH: 114
<212> TYPE: PRT
<213> ORGANISM: Artificial Sequence
<220> FEATURE:
<223> OTHER INFORMATION: Amino acid sequence with preferred framework
      for variable light chain.

<400> SEQUENCE: 34

Asp Ile Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Asp Gly Thr Lys Leu Glu Leu Lys
            100                 105                 110

Arg Ala

<210> SEQ ID NO 35
<211> LENGTH: 114
<212> TYPE: PRT
<213> ORGANISM: Artificial Sequence
<220> FEATURE:
<223> OTHER INFORMATION: Amino acid sequence with preferred framework
      for variable light chain.

<400> SEQUENCE: 35

Asp Ile Val Met Thr Gln Ala Ala Phe Ser Asn Pro Val Thr Leu Gly
  1               5                  10                  15

Thr Ser Ala Ser Ile Ser Cys Arg Ser Ser Lys Ser Leu Leu His Ser
                 20                  25                  30

Asn Gly Ile Thr Tyr Phe Phe Trp Tyr Leu Gln Lys Pro Gly Leu Ser
            35                  40                  45

Pro Gln Leu Leu Ile Tyr Gln Met Ser Asn Leu Ala Ser Gly Val Pro
 50                  55                  60

Asp Arg Phe Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Pro Thr Phe Gly Gly Gly Thr Lys Leu Glu Ile Lys
            100                 105                 110

Arg Ala

<210> SEQ ID NO 36
<211> LENGTH: 275
<212> TYPE: PRT
<213> ORGANISM: Artificial Sequence
<220> FEATURE:
<223> OTHER INFORMATION: Single chain Fv format sequence

<400> SEQUENCE: 36

Glu Val Lys Leu Val Glu Ser Gly Gly Gly Leu Val Gln Pro Gly Gly
  1               5                  10                  15

Ser Met Lys Leu Ser Cys Ala Ala Ser Gly Phe Thr Phe Ser Asp Ala
                 20                  25                  30

Trp Met Asp Trp Val Arg Gln Ser Pro Glu Lys Gly Leu Glu Trp Val
            35                  40                  45

Ala Glu Ile Arg Ser Lys Ala Asn Asn His Ala Thr Tyr Tyr Ala Glu
 50                  55                  60

Ser Val Lys Gly Arg Phe Thr Ile Ser Arg Asp Val Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg Gly Gly Tyr Gly Phe Asp Tyr Trp Gly Gln Gly Thr
            100                 105                 110

Thr Leu Thr Val Ser Ser Ala Ser Ser Gly Gly Gly Ser Gly Gly
            115                 120                 125
```

```
Gly Gly Ser Gly Gly Ser Ala Arg Asp Ile Val Leu Thr Gln Thr Pro
            130                 135                 140

Leu Ser Leu Pro Val Ser Leu Gly Asp Gln Ala Ser Ile Ser Cys Arg
145                 150                 155                 160

Ser Ser Gln Ser Ile Val His Ser Asn Gly Asn Thr Tyr Leu Glu Trp
                165                 170                 175

Tyr Leu Gln Lys Pro Gly Gln Ser Pro Lys Leu Leu Ile Tyr Lys Val
            180                 185                 190

Ser Asn Arg Phe Ser Gly Val Pro Asp Arg Phe Ser Gly Ser Gly Ser
        195                 200                 205

Gly Thr Asp Phe Thr Leu Lys Ile Ser Arg Val Glu Ala Glu Asp Leu
210                 215                 220

Gly Val Tyr Tyr Cys Phe Gln Gly Ser His Val Pro Leu Thr Phe Gly
225                 230                 235                 240

Asp Gly Thr Lys Leu Glu Leu Lys Arg Ala Ala Ala His His His His
            245                 250                 255

His His Gly Ala Ala Glu Gln Lys Leu Ile Ser Glu Glu Asp Leu Asn
                260                 265                 270

Gly Ala Ala
        275

<210> SEQ ID NO 37
<211> LENGTH: 266
<212> TYPE: PRT
<213> ORGANISM: Artificial Sequence
<220> FEATURE:
<223> OTHER INFORMATION: Single chain Fv format sequence

<400> SEQUENCE: 37

Glu Val Lys Leu Val Glu Ser Gly Gly Gly Leu Val Gln Pro Gly Gly
  1               5                  10                  15

Ser Met Lys Leu Ser Cys Ala Ala Ser Gly Phe Thr Phe Ser Asp Ala
             20                  25                  30

Trp Met Asp Trp Val Arg Gln Ser Pro Glu Lys Gly Leu Glu Trp Val
         35                  40                  45

Ala Glu Ile Arg Ser Lys Ala Asn Asn His Ala Thr Tyr Tyr Ala Glu
 50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                 85                  90                  95

Tyr Cys Thr Arg Gly Gly Tyr Gly Phe Asp Tyr Trp Gly Gln Gly Thr
            100                 105                 110

Thr Leu Thr Val Ser Ser Ala Ser Gly Ser Gly Ser Gly Ser Ala Asp
        115                 120                 125

Ile Val Leu Thr Gln Thr Pro Leu Ser Leu Pro Val Ser Leu Gly Asp
    130                 135                 140

Gln Ala Ser Ile Ser Cys Arg Ser Ser Gln Ser Ile Val His Ser Asn
145                 150                 155                 160

Gly Asn Thr Tyr Leu Glu Trp Tyr Leu Gln Lys Pro Gly Gln Ser Pro
                165                 170                 175

Lys Leu Leu Ile Tyr Lys Val Ser Asn Arg Phe Ser Gly Val Pro Asp
            180                 185                 190

Arg Phe Ser Gly Ser Gly Ser Gly Thr Asp Phe Thr Leu Lys Ile Ser
        195                 200                 205
```

```
Arg Val Glu Ala Glu Asp Leu Gly Val Tyr Tyr Cys Phe Gln Gly Ser
    210                 215                 220

His Val Pro Leu Thr Phe Gly Asp Gly Thr Lys Leu Glu Leu Lys Arg
225                 230                 235                 240

Ala Ala Ala His His His His His Gly Ala Ala Glu Gln Lys Leu
                245                 250                 255

Ile Ser Glu Glu Asp Leu Asn Gly Ala Ala
            260                 265

<210> SEQ ID NO 38
<211> LENGTH: 265
<212> TYPE: PRT
<213> ORGANISM: Artificial Sequence
<220> FEATURE:
<223> OTHER INFORMATION: Single chain Fv format sequence

<400> SEQUENCE: 38

Glu Val Lys Leu Val Glu Ser Gly Gly Gly Leu Val Gln Pro Gly Gly
  1               5                  10                  15

Ser Met Lys Leu Ser Cys Ala Ala Ser Gly Phe Thr Phe Ser Asp Ala
                 20                  25                  30

Trp Met Asp Trp Val Arg Gln Ser Pro Glu Lys Gly Leu Glu Trp Val
             35                  40                  45

Ala Glu Ile Arg Ser Lys Ala Asn Asn His Ala Thr Tyr Tyr Ala Glu
 50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                 85                  90                  95

Tyr Cys Thr Arg Gly Gly Tyr Gly Phe Asp Tyr Trp Gly Gln Gly Thr
            100                 105                 110

Thr Leu Thr Val Ser Ser Ala Ser Ser Gly Gly Ser Ser Ala Asp Ile
        115                 120                 125

Val Leu Thr Gln Thr Pro Leu Ser Leu Pro Val Ser Leu Gly Asp Gln
130                 135                 140

Ala Ser Ile Ser Cys Arg Ser Ser Gln Ser Ile Val His Ser Asn Gly
145                 150                 155                 160

Asn Thr Tyr Leu Glu Trp Tyr Leu Gln Lys Pro Gly Gln Ser Pro Lys
                165                 170                 175

Leu Leu Ile Tyr Lys Val Ser Asn Arg Phe Ser Gly Val Pro Asp Arg
            180                 185                 190

Phe Ser Gly Ser Gly Ser Gly Thr Asp Phe Thr Leu Lys Ile Ser Arg
        195                 200                 205

Val Glu Ala Glu Asp Leu Gly Val Tyr Tyr Cys Phe Gln Gly Ser His
    210                 215                 220

Val Pro Leu Thr Phe Gly Asp Gly Thr Lys Leu Glu Leu Lys Arg Ala
225                 230                 235                 240

Ala Ala His His His His His Gly Ala Ala Glu Gln Lys Leu Ile
                245                 250                 255

Ser Glu Glu Asp Leu Asn Gly Ala Ala
            260                 265

<210> SEQ ID NO 39
<211> LENGTH: 264
<212> TYPE: PRT
<213> ORGANISM: Artificial Sequence
```

```
<220> FEATURE:
<223> OTHER INFORMATION: Single chain Fv format sequence

<400> SEQUENCE: 39
```

| Glu | Val | Lys | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Met | Lys | Leu | Ser | Cys | Ala | Ala | Ser | Gly | Phe | Thr | Phe | Ser | Asp | Ala |
|---|---|---|---|---|---|---|---|---|---|---|---|---|---|---|---|
| | | | 20 | | | | | 25 | | | | | 30 | | |

| Trp | Met | Asp | Trp | Val | Arg | Gln | Ser | Pro | Glu | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Glu | Ile | Arg | Ser | Lys | Ala | Asn | Asn | His | Ala | Thr | Tyr | Tyr | Ala | Glu |
|---|---|---|---|---|---|---|---|---|---|---|---|---|---|---|---|
| | 50 | | | | | 55 | | | | | 60 | | | | |

| Ser | Val | Lys | Gly | Arg | Phe | Thr | Ile | Ser | Arg | Asp | Val | Ser | Lys | Ser | Ser |
|---|---|---|---|---|---|---|---|---|---|---|---|---|---|---|---|
| 65 | | | | | 70 | | | | | 75 | | | | | 80 |

| Val | Tyr | Leu | Gln | Met | Asn | Asn | Leu | Arg | Ala | Glu | Asp | Thr | Gly | Ile | Tyr |
|---|---|---|---|---|---|---|---|---|---|---|---|---|---|---|---|
| | | | | 85 | | | | | 90 | | | | | 95 | |

| Tyr | Cys | Thr | Arg | Gly | Gly | Tyr | Gly | Phe | Asp | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Thr | Leu | Thr | Val | Ser | Ser | Ala | Ser | Ser | Gly | Ser | Ser | Ala | Asp | Ile | Val |
|---|---|---|---|---|---|---|---|---|---|---|---|---|---|---|---|
| | | 115 | | | | | 120 | | | | | 125 | | | |

| Leu | Thr | Gln | Thr | Pro | Leu | Ser | Leu | Pro | Val | Ser | Leu | Gly | Asp | Gln | Ala |
|---|---|---|---|---|---|---|---|---|---|---|---|---|---|---|---|
| | 130 | | | | | 135 | | | | | 140 | | | | |

| Ser | Ile | Ser | Cys | Arg | Ser | Ser | Gln | Ser | Ile | Val | His | Ser | Asn | Gly | Asn |
|---|---|---|---|---|---|---|---|---|---|---|---|---|---|---|---|
| 145 | | | | | 150 | | | | | 155 | | | | | 160 |

| Thr | Tyr | Leu | Glu | Trp | Tyr | Leu | Gln | Lys | Pro | Gly | Gln | Ser | Pro | Lys | Leu |
|---|---|---|---|---|---|---|---|---|---|---|---|---|---|---|---|
| | | | | 165 | | | | | 170 | | | | | 175 | |

| Leu | Ile | Tyr | Lys | Val | Ser | Asn | Arg | Phe | Ser | Gly | Val | Pro | Asp | Arg | Phe |
|---|---|---|---|---|---|---|---|---|---|---|---|---|---|---|---|
| | | | 180 | | | | | 185 | | | | | 190 | | |

| Ser | Gly | Ser | Gly | Ser | Gly | Thr | Asp | Phe | Thr | Leu | Lys | Ile | Ser | Arg | Val |
|---|---|---|---|---|---|---|---|---|---|---|---|---|---|---|---|
| | | 195 | | | | | 200 | | | | | 205 | | | |

| Glu | Ala | Glu | Asp | Leu | Gly | Val | Tyr | Tyr | Cys | Phe | Gln | Gly | Ser | His | Val |
|---|---|---|---|---|---|---|---|---|---|---|---|---|---|---|---|
| | 210 | | | | | 215 | | | | | 220 | | | | |

| Pro | Leu | Thr | Phe | Gly | Asp | Gly | Thr | Lys | Leu | Glu | Leu | Lys | Arg | Ala | Ala |
|---|---|---|---|---|---|---|---|---|---|---|---|---|---|---|---|
| 225 | | | | | 230 | | | | | 235 | | | | | 240 |

| Ala | His | His | His | His | His | Gly | Ala | Ala | Glu | Gln | Lys | Leu | Ile | Ser |
|---|---|---|---|---|---|---|---|---|---|---|---|---|---|---|
| | | | | 245 | | | | | 250 | | | | | 255 |

| Glu | Glu | Asp | Leu | Asn | Gly | Ala | Ala |
|---|---|---|---|---|---|---|---|
| | | | 260 | | | | |

```
<210> SEQ ID NO 40
<211> LENGTH: 263
<212> TYPE: PRT
<213> ORGANISM: Artificial Sequence
<220> FEATURE:
<223> OTHER INFORMATION: Single chain Fv format sequence

<400> SEQUENCE: 40
```

| Glu | Val | Lys | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Met | Lys | Leu | Ser | Cys | Ala | Ala | Ser | Gly | Phe | Thr | Phe | Ser | Asp | Ala |
|---|---|---|---|---|---|---|---|---|---|---|---|---|---|---|---|
| | | | 20 | | | | | 25 | | | | | 30 | | |

| Trp | Met | Asp | Trp | Val | Arg | Gln | Ser | Pro | Glu | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Glu | Ile | Arg | Ser | Lys | Ala | Asn | Asn | His | Ala | Thr | Tyr | Tyr | Ala | Glu |
|---|---|---|---|---|---|---|---|---|---|---|---|---|---|---|---|
| | 50 | | | | | 55 | | | | | 60 | | | | |

| Ser | Val | Lys | Gly | Arg | Phe | Thr | Ile | Ser | Arg | Asp | Val | Ser | Lys | Ser | Ser |

```
                65                  70                  75                  80
Val Tyr Leu Gln Met Asn Asn Leu Arg Ala Glu Asp Thr Gly Ile Tyr
                    85                  90                  95

Tyr Cys Thr Arg Gly Gly Tyr Gly Phe Asp Tyr Trp Gly Gln Gly Thr
                    100                 105                 110

Thr Leu Thr Val Ser Ser Ala Ser Ser Ser Ala Asp Ile Val Leu
                    115                 120                 125

Thr Gln Thr Pro Leu Ser Leu Pro Val Ser Leu Gly Asp Gln Ala Ser
                    130                 135                 140

Ile Ser Cys Arg Ser Ser Gln Ser Ile Val His Ser Asn Gly Asn Thr
145                 150                 155                 160

Tyr Leu Glu Trp Tyr Leu Gln Lys Pro Gly Gln Ser Pro Lys Leu Leu
                    165                 170                 175

Ile Tyr Lys Val Ser Asn Arg Phe Ser Gly Val Pro Asp Arg Phe Ser
                    180                 185                 190

Gly Ser Gly Ser Gly Thr Asp Phe Thr Leu Lys Ile Ser Arg Val Glu
                    195                 200                 205

Ala Glu Asp Leu Gly Val Tyr Tyr Cys Phe Gln Gly Ser His Val Pro
                    210                 215                 220

Leu Thr Phe Gly Asp Gly Thr Lys Leu Glu Leu Lys Arg Ala Ala Ala
225                 230                 235                 240

His His His His His His Gly Ala Ala Glu Gln Lys Leu Ile Ser Glu
                    245                 250                 255

Glu Asp Leu Asn Gly Ala Ala
                    260

<210> SEQ ID NO 41
<211> LENGTH: 262
<212> TYPE: PRT
<213> ORGANISM: Artificial Sequence
<220> FEATURE:
<223> OTHER INFORMATION: Single chain Fv format sequence

<400> SEQUENCE: 41

Glu Val Lys Leu Val Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                    20                  25                  30

Trp Met Asp Trp Val Arg Gln Ser Pro Glu Lys Gly Leu Glu Trp Val
                    35                  40                  45

Ala Glu Ile Arg Ser Lys Ala Asn Asn His Ala Thr Tyr Tyr Ala Glu
                    50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                    85                  90                  95

Tyr Cys Thr Arg Gly Gly Tyr Gly Phe Asp Tyr Trp Gly Gln Gly Thr
                    100                 105                 110

Thr Leu Thr Val Ser Ser Ala Ser Ser Ser Ala Asp Ile Val Leu Thr
                    115                 120                 125

Gln Thr Pro Leu Ser Leu Pro Val Ser Leu Gly Asp Gln Ala Ser Ile
                    130                 135                 140

Ser Cys Arg Ser Ser Gln Ser Ile Val His Ser Asn Gly Asn Thr Tyr
145                 150                 155                 160

Leu Glu Trp Tyr Leu Gln Lys Pro Gly Gln Ser Pro Lys Leu Leu Ile
```

```
            165                 170                 175

Tyr Lys Val Ser Asn Arg Phe Ser Gly Val Pro Asp Arg Phe Ser Gly
            180                 185                 190

Ser Gly Ser Gly Thr Asp Phe Thr Leu Lys Ile Ser Arg Val Glu Ala
            195                 200                 205

Glu Asp Leu Gly Val Tyr Tyr Cys Phe Gln Gly Ser His Val Pro Leu
            210                 215                 220

Thr Phe Gly Asp Gly Thr Lys Leu Glu Leu Lys Arg Ala Ala Ala His
225                 230                 235                 240

His His His His Gly Ala Ala Glu Gln Lys Leu Ile Ser Glu Glu
                245                 250                 255

Asp Leu Asn Gly Ala Ala
            260

<210> SEQ ID NO 42
<211> LENGTH: 261
<212> TYPE: PRT
<213> ORGANISM: Artificial Sequence
<220> FEATURE:
<223> OTHER INFORMATION: Single chain Fv format sequence

<400> SEQUENCE: 42

Glu Val Lys Leu Val Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
            100                 105                 110

Thr Leu Thr Val Ser Ser Ala Ser Ala Asp Ile Val Leu Thr Gln
        115                 120                 125

Thr Pro Leu Ser Leu Pro Val Ser Leu Gly Asp Gln Ala Ser Ile Ser
    130                 135                 140

Cys Arg Ser Ser Gln Ser Ile Val His Ser Asn Gly Asn Thr Tyr Leu
145                 150                 155                 160

Glu Trp Tyr Leu Gln Lys Pro Gly Gln Ser Pro Lys Leu Leu Ile Tyr
                165                 170                 175

Lys Val Ser Asn Arg Phe Ser Gly Val Pro Asp Arg Phe Ser Gly Ser
            180                 185                 190

Gly Ser Gly Thr Asp Phe Thr Leu Lys Ile Ser Arg Val Glu Ala Glu
        195                 200                 205

Asp Leu Gly Val Tyr Tyr Cys Phe Gln Gly Ser His Val Pro Leu Thr
    210                 215                 220

Phe Gly Asp Gly Thr Lys Leu Glu Leu Lys Arg Ala Ala Ala His His
225                 230                 235                 240

His His His His Gly Ala Ala Glu Gln Lys Leu Ile Ser Glu Glu Asp
                245                 250                 255

Leu Asn Gly Ala Ala
            260
```

-continued

```
                260

<210> SEQ ID NO 43
<211> LENGTH: 260
<212> TYPE: PRT
<213> ORGANISM: Artificial Sequence
<220> FEATURE:
<223> OTHER INFORMATION: Single chain Fv format sequence

<400> SEQUENCE: 43

Glu Val Lys Leu Val Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
            100                 105                 110

Thr Leu Thr Val Ser Ser Ala Ser Ala Asp Ile Val Leu Thr Gln Thr
        115                 120                 125

Pro Leu Ser Leu Pro Val Ser Leu Gly Asp Gln Ala Ser Ile Ser Cys
    130                 135                 140

Arg Ser Ser Gln Ser Ile Val His Ser Asn Gly Asn Thr Tyr Leu Glu
145                 150                 155                 160

Trp Tyr Leu Gln Lys Pro Gly Gln Ser Pro Lys Leu Leu Ile Tyr Lys
                165                 170                 175

Val Ser Asn Arg Phe Ser Gly Val Pro Asp Arg Phe Ser Gly Ser Gly
            180                 185                 190

Ser Gly Thr Asp Phe Thr Leu Lys Ile Ser Arg Val Glu Ala Glu Asp
        195                 200                 205

Leu Gly Val Tyr Tyr Cys Phe Gln Gly Ser His Val Pro Leu Thr Phe
    210                 215                 220

Gly Asp Gly Thr Lys Leu Glu Leu Lys Arg Ala Ala His His His His
225                 230                 235                 240

His His His Gly Ala Ala Glu Gln Lys Leu Ile Ser Glu Glu Asp Leu
                245                 250                 255

Asn Gly Ala Ala
            260

<210> SEQ ID NO 44
<211> LENGTH: 259
<212> TYPE: PRT
<213> ORGANISM: Artificial Sequence
<220> FEATURE:
<223> OTHER INFORMATION: Single chain Fv format sequence

<400> SEQUENCE: 44

Glu Val Lys Leu Val Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
            20                  25                  30
```

```
Trp Met Asp Trp Val Arg Gln Ser Pro Glu Lys Gly Leu Glu Trp Val
            35                  40                  45

Ala Glu Ile Arg Ser Lys Ala Asn Asn His Ala Thr Tyr Tyr Ala Glu
 50                  55                  60

Ser Val Lys Gly Arg Phe Thr Ile Ser Arg Asp Val Ser Lys Ser Ser
 65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
                100                 105                 110

Thr Leu Thr Val Ser Ser Ala Ala Asp Ile Val Leu Thr Gln Thr Pro
            115                 120                 125

Leu Ser Leu Pro Val Ser Leu Gly Asp Gln Ala Ser Ile Ser Cys Arg
130                 135                 140

Ser Ser Gln Ser Ile Val His Ser Asn Gly Asn Thr Tyr Leu Glu Trp
145                 150                 155                 160

Tyr Leu Gln Lys Pro Gly Gln Ser Pro Lys Leu Leu Ile Tyr Lys Val
                165                 170                 175

Ser Asn Arg Phe Ser Gly Val Pro Asp Arg Phe Ser Gly Ser Gly Ser
                180                 185                 190

Gly Thr Asp Phe Thr Leu Lys Ile Ser Arg Val Glu Ala Glu Asp Leu
            195                 200                 205

Gly Val Tyr Tyr Cys Phe Gln Gly Ser His Val Pro Leu Thr Phe Gly
        210                 215                 220

Asp Gly Thr Lys Leu Glu Leu Lys Arg Ala Ala His His His His His
225                 230                 235                 240

His His Gly Ala Ala Glu Gln Lys Leu Ile Ser Glu Glu Asp Leu Asn
                245                 250                 255

Gly Ala Ala

<210> SEQ ID NO 45
<211> LENGTH: 255
<212> TYPE: PRT
<213> ORGANISM: Artificial Sequence
<220> FEATURE:
<223> OTHER INFORMATION: Single chain Fv format sequence

<400> SEQUENCE: 45

Glu Val Lys Leu Val Glu Ser Gly Gly Gly Leu Val Gln Pro Gly Gly
 1               5                  10                  15

Ser Met Lys Leu Ser Cys Ala Ser Gly Phe Thr Phe Ser Asp Ala
            20                  25                  30

Trp Met Asp Trp Val Arg Gln Ser Pro Glu Lys Gly Leu Glu Trp Val
            35                  40                  45

Ala Glu Ile Arg Ser Lys Ala Asn Asn His Ala Thr Tyr Tyr Ala Glu
 50                  55                  60

Ser Val Lys Gly Arg Phe Thr Ile Ser Arg Asp Val Ser Lys Ser Ser
 65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
                100                 105                 110

Thr Leu Thr Val Ser Ser Ala Asp Ile Val Leu Thr Gln Thr Pro Leu
            115                 120                 125

Ser Leu Pro Val Ser Leu Gly Asp Gln Ala Ser Ile Ser Cys Arg Ser
```

```
                130                 135                 140
Ser Gln Ser Ile Val His Ser Asn Gly Asn Thr Tyr Leu Glu Trp Tyr
145                 150                 155                 160

Leu Gln Lys Pro Gly Gln Ser Pro Lys Leu Leu Ile Tyr Lys Val Ser
                165                 170                 175

Asn Arg Phe Ser Gly Val Pro Asp Arg Phe Ser Gly Ser Gly Ser Gly
                180                 185                 190

Thr Asp Phe Thr Leu Lys Ile Ser Arg Val Glu Ala Glu Asp Leu Gly
                195                 200                 205

Val Tyr Tyr Cys Phe Gln Gly Ser His Val Pro Leu Thr Phe Gly Asp
                210                 215                 220

Gly Thr Lys Leu Glu Leu Lys Arg Ala Ala Ala His His His His His
225                 230                 235                 240

His Gly Ala Ala Glu Gln Lys Leu Ile Ser Glu Glu Val His Gln
                245                 250                 255

<210> SEQ ID NO 46
<211> LENGTH: 257
<212> TYPE: PRT
<213> ORGANISM: Artificial Sequence
<220> FEATURE:
<223> OTHER INFORMATION: Single chain Fv format sequence

<400> SEQUENCE: 46

Glu Val Lys Leu Val Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
                35                  40                  45

Ala Glu Ile Arg Ser Lys Ala Asn Asn His Ala Thr Tyr Tyr Ala Glu
                50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
                100                 105                 110

Thr Leu Thr Val Ser Ser Asp Ile Val Leu Thr Gln Thr Pro Leu Ser
                115                 120                 125

Leu Pro Val Ser Leu Gly Asp Gln Ala Ser Ile Ser Cys Arg Ser Ser
                130                 135                 140

Gln Ser Ile Val His Ser Asn Gly Asn Thr Tyr Leu Glu Trp Tyr Leu
145                 150                 155                 160

Gln Lys Pro Gly Gln Ser Pro Lys Leu Leu Ile Tyr Lys Val Ser Asn
                165                 170                 175

Arg Phe Ser Gly Val Pro Asp Arg Phe Ser Gly Ser Gly Ser Gly Thr
                180                 185                 190

Asp Phe Thr Leu Lys Ile Ser Arg Val Glu Ala Glu Asp Leu Gly Val
                195                 200                 205

Tyr Tyr Cys Phe Gln Gly Ser His Val Pro Leu Thr Phe Gly Asp Gly
                210                 215                 220

Thr Lys Leu Glu Leu Lys Arg Ala Ala Ala His His His His His His
225                 230                 235                 240

Gly Ala Ala Glu Gln Lys Leu Ile Ser Glu Glu Asp Leu Asn Gly Ala
```

```
                    245                 250                 255

Ala

<210> SEQ ID NO 47
<211> LENGTH: 256
<212> TYPE: PRT
<213> ORGANISM: Artificial Sequence
<220> FEATURE:
<223> OTHER INFORMATION: Single chain Fv format sequence

<400> SEQUENCE: 47

Glu Val Lys Leu Val Glu Ser Gly Gly Gly Leu Val Gln Pro Gly Gly
  1               5                  10                  15

Ser Met Lys Leu Ser Cys Ala Ala Ser Gly Phe Thr Phe Ser Asp Ala
                 20                  25                  30

Trp Met Asp Trp Val Arg Gln Ser Pro Glu Lys Gly Leu Glu Trp Val
             35                  40                  45

Ala Glu Ile Arg Ser Lys Ala Asn Asn His Ala Thr Tyr Tyr Ala Glu
         50                  55                  60

Ser Val Lys Gly Arg Phe Thr Ile Ser Arg Asp Val Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg Gly Gly Tyr Gly Phe Asp Tyr Trp Gly Gln Gly Thr
            100                 105                 110

Thr Leu Thr Val Ser Asp Ile Val Leu Thr Gln Thr Pro Leu Ser Leu
        115                 120                 125

Pro Val Ser Leu Gly Asp Gln Ala Ser Ile Ser Cys Arg Ser Ser Gln
130                 135                 140

Ser Ile Val His Ser Asn Gly Asn Thr Tyr Leu Glu Trp Tyr Leu Gln
145                 150                 155                 160

Lys Pro Gly Gln Ser Pro Lys Leu Leu Ile Tyr Lys Val Ser Asn Arg
                165                 170                 175

Phe Ser Gly Val Pro Asp Arg Phe Ser Gly Ser Gly Ser Gly Thr Asp
            180                 185                 190

Phe Thr Leu Lys Ile Ser Arg Val Glu Ala Glu Asp Leu Gly Val Tyr
        195                 200                 205

Tyr Cys Phe Gln Gly Ser His Val Pro Leu Thr Phe Gly Asp Gly Thr
    210                 215                 220

Lys Leu Glu Leu Lys Arg Ala Ala Ala His His His His His His Gly
225                 230                 235                 240

Ala Ala Glu Gln Lys Leu Ile Ser Glu Glu Asp Leu Asn Gly Ala Ala
                245                 250                 255

<210> SEQ ID NO 48
<211> LENGTH: 274
<212> TYPE: PRT
<213> ORGANISM: Artificial Sequence
<220> FEATURE:
<223> OTHER INFORMATION: Single chain Fv format sequence

<400> SEQUENCE: 48

Glu Val Lys Leu Val Glu Ser Gly Gly Gly Leu Val Gln Pro Gly Gly
  1               5                  10                  15

Ser Met Lys Leu Ser Cys Val Ala Ser Gly Phe Thr Phe Ser Asn Tyr
                 20                  25                  30

Trp Met Asn Trp Val Arg Gln Ser Pro Glu Lys Gly Leu Glu Trp Val
```

```
                35                  40                  45
Ala Glu Ile Arg Leu Lys Ser Asn Asn Tyr Thr Thr His Tyr Ala Glu
 50                  55                  60

Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
                 85                  90                  95

Tyr Cys Thr Arg His Tyr Tyr Phe Asp Tyr Trp Gly Gln Gly Thr Thr
                100                 105                 110

Leu Thr Val Ser Ser Ala Ser Ser Gly Gly Gly Ser Gly Gly Gly
            115                 120                 125

Gly Ser Gly Gly Ser Ala Arg Asp Ile Val Met Thr Gln Ala Ala Phe
            130                 135                 140

Ser Asn Pro Val Thr Leu Gly Thr Ser Ala Ser Ile Ser Cys Arg Ser
145                 150                 155                 160

Ser Lys Ser Leu Leu His Ser Asn Gly Ile Thr Tyr Phe Phe Trp Tyr
                165                 170                 175

Leu Gln Lys Pro Gly Leu Ser Pro Gln Leu Leu Ile Tyr Gln Met Ser
            180                 185                 190

Asn Leu Ala Ser Gly Val Pro Asp Arg Phe Ser Ser Ser Gly Ser Gly
        195                 200                 205

Thr Asp Phe Thr Leu Arg Ile Ser Arg Val Glu Ala Glu Asp Val Gly
210                 215                 220

Val Tyr Tyr Cys Ala Gln Asn Leu Glu Leu Pro Pro Thr Phe Gly Gly
225                 230                 235                 240

Gly Thr Lys Leu Glu Ile Lys Arg Ala Ala Ala His His His His
                245                 250                 255

His Gly Ala Ala Glu Gln Lys Leu Ile Ser Glu Glu Asp Leu Asn Gly
            260                 265                 270

Ala Ala

<210> SEQ ID NO 49
<211> LENGTH: 265
<212> TYPE: PRT
<213> ORGANISM: Artificial Sequence
<220> FEATURE:
<223> OTHER INFORMATION: Single chain Fv format sequence

<400> SEQUENCE: 49

Glu Val Lys Leu Val Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Thr Thr His Tyr Ala Glu
 50                  55                  60

Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
                 85                  90                  95

Tyr Cys Thr Arg His Tyr Tyr Phe Asp Tyr Trp Gly Gln Gly Thr Thr
                100                 105                 110

Leu Thr Val Ser Ser Ala Ser Ser Gly Ser Gly Ser Ala Asp Ile
            115                 120                 125
```

```
Val Met Thr Gln Ala Ala Phe Ser Asn Pro Val Thr Leu Gly Thr Ser
    130                 135                 140

Ala Ser Ile Ser Cys Arg Ser Ser Lys Ser Leu Leu His Ser Asn Gly
145                 150                 155                 160

Ile Thr Tyr Phe Phe Trp Tyr Leu Gln Lys Pro Gly Leu Ser Pro Gln
                165                 170                 175

Leu Leu Ile Tyr Gln Met Ser Asn Leu Ala Ser Gly Val Pro Asp Arg
                180                 185                 190

Phe Ser Ser Ser Gly Ser Gly Thr Asp Phe Thr Leu Arg Ile Ser Arg
                195                 200                 205

Val Glu Ala Glu Asp Val Gly Val Tyr Tyr Cys Ala Gln Asn Leu Glu
    210                 215                 220

Leu Pro Pro Thr Phe Gly Gly Gly Thr Lys Leu Glu Ile Lys Arg Ala
225                 230                 235                 240

Ala Ala His His His His His His Gly Ala Ala Glu Gln Lys Leu Ile
                245                 250                 255

Ser Glu Glu Asp Leu Asn Gly Ala Ala
                260                 265

<210> SEQ ID NO 50
<211> LENGTH: 264
<212> TYPE: PRT
<213> ORGANISM: Artificial Sequence
<220> FEATURE:
<223> OTHER INFORMATION: Single chain Fv format sequence

<400> SEQUENCE: 50

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
                100                 105                 110

Leu Thr Val Ser Ser Ala Ser Ser Gly Gly Ser Ser Ala Asp Ile Val
            115                 120                 125

Met Thr Gln Ala Ala Phe Ser Asn Pro Val Thr Leu Gly Thr Ser Ala
    130                 135                 140

Ser Ile Ser Cys Arg Ser Ser Lys Ser Leu Leu His Ser Asn Gly Ile
145                 150                 155                 160

Thr Tyr Phe Phe Trp Tyr Leu Gln Lys Pro Gly Leu Ser Pro Gln Leu
                165                 170                 175

Leu Ile Tyr Gln Met Ser Asn Leu Ala Ser Gly Val Pro Asp Arg Phe
                180                 185                 190

Ser Ser Ser Gly Ser Gly Thr Asp Phe Thr Leu Arg Ile Ser Arg Val
            195                 200                 205

Glu Ala Glu Asp Val Gly Val Tyr Tyr Cys Ala Gln Asn Leu Glu Leu
    210                 215                 220
```

```
Pro Pro Thr Phe Gly Gly Gly Thr Lys Leu Glu Ile Lys Arg Ala Ala
225                 230                 235                 240

Ala His His His His His Gly Ala Ala Glu Gln Lys Leu Ile Ser
                    245                 250                 255

Glu Glu Asp Leu Asn Gly Ala Ala
                260

<210> SEQ ID NO 51
<211> LENGTH: 263
<212> TYPE: PRT
<213> ORGANISM: Artificial Sequence
<220> FEATURE:
<223> OTHER INFORMATION: Single chain Fv format sequence

<400> SEQUENCE: 51

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Thr Thr His Tyr Ala Glu
        50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Ser Ala Ser Ser Gly Ser Ser Ala Asp Ile Val Met
        115                 120                 125

Thr Gln Ala Ala Phe Ser Asn Pro Val Thr Leu Gly Thr Ser Ala Ser
130                 135                 140

Ile Ser Cys Arg Ser Ser Lys Ser Leu Leu His Ser Asn Gly Ile Thr
145                 150                 155                 160

Tyr Phe Phe Trp Tyr Leu Gln Lys Pro Gly Leu Ser Pro Gln Leu Leu
                165                 170                 175

Ile Tyr Gln Met Ser Asn Leu Ala Ser Gly Val Pro Arg Phe Ser
            180                 185                 190

Ser Ser Gly Ser Gly Thr Asp Phe Thr Leu Arg Ile Ser Arg Val Glu
        195                 200                 205

Ala Glu Asp Val Gly Val Tyr Tyr Cys Ala Gln Asn Leu Glu Leu Pro
210                 215                 220

Pro Thr Phe Gly Gly Gly Thr Lys Leu Glu Ile Lys Arg Ala Ala Ala
225                 230                 235                 240

His His His His His His Gly Ala Ala Glu Gln Lys Leu Ile Ser Glu
                245                 250                 255

Glu Asp Leu Asn Gly Ala Ala
                260

<210> SEQ ID NO 52
<211> LENGTH: 262
<212> TYPE: PRT
<213> ORGANISM: Artificial Sequence
<220> FEATURE:
<223> OTHER INFORMATION: Single chain Fv format sequence
```

<400> SEQUENCE: 52

```
Glu Val Lys Leu Val Glu Ser Gly Gly Gly Leu Val Gln Pro Gly Gly
  1               5                  10                  15

Ser Met Lys Leu Ser Cys Val Ala Ser Gly Phe Thr Phe Ser Asn Tyr
             20                  25                  30

Trp Met Asn Trp Val Arg Gln Ser Pro Glu Lys Gly Leu Glu Trp Val
         35                  40                  45

Ala Glu Ile Arg Leu Lys Ser Asn Asn Tyr Thr Thr His Tyr Ala Glu
     50                  55                  60

Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
                 85                  90                  95

Tyr Cys Thr Arg His Tyr Tyr Phe Asp Tyr Trp Gly Gln Gly Thr Thr
             100                 105                 110

Leu Thr Val Ser Ser Ala Ser Ser Ser Ala Asp Ile Val Met Thr
         115                 120                 125

Gln Ala Ala Phe Ser Asn Pro Val Thr Leu Gly Thr Ser Ala Ser Ile
    130                 135                 140

Ser Cys Arg Ser Ser Lys Ser Leu Leu His Ser Asn Gly Ile Thr Tyr
145                 150                 155                 160

Phe Phe Trp Tyr Leu Gln Lys Pro Gly Leu Ser Pro Gln Leu Leu Ile
                165                 170                 175

Tyr Gln Met Ser Asn Leu Ala Ser Gly Val Pro Asp Arg Phe Ser Ser
            180                 185                 190

Ser Gly Ser Gly Thr Asp Phe Thr Leu Arg Ile Ser Arg Val Glu Ala
        195                 200                 205

Glu Asp Val Gly Val Tyr Tyr Cys Ala Gln Asn Leu Glu Leu Pro Pro
    210                 215                 220

Thr Phe Gly Gly Gly Thr Lys Leu Glu Ile Lys Arg Ala Ala Ala His
225                 230                 235                 240

His His His His His Gly Ala Ala Glu Gln Lys Leu Ile Ser Glu Glu
                245                 250                 255

Asp Leu Asn Gly Ala Ala
            260
```

<210> SEQ ID NO 53
<211> LENGTH: 261
<212> TYPE: PRT
<213> ORGANISM: Artificial Sequence
<220> FEATURE:
<223> OTHER INFORMATION: Single chain Fv format sequence

<400> SEQUENCE: 53

```
Glu Val Lys Leu Val Glu Ser Gly Gly Gly Leu Val Gln Pro Gly Gly
  1               5                  10                  15

Ser Met Lys Leu Ser Cys Val Ala Ser Gly Phe Thr Phe Ser Asn Tyr
             20                  25                  30

Trp Met Asn Trp Val Arg Gln Ser Pro Glu Lys Gly Leu Glu Trp Val
         35                  40                  45

Ala Glu Ile Arg Leu Lys Ser Asn Asn Tyr Thr Thr His Tyr Ala Glu
     50                  55                  60

Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
```

85                  90                  95

Tyr Cys Thr Arg His Tyr Tyr Phe Asp Tyr Trp Gly Gln Gly Thr Thr
                100                 105                 110

Leu Thr Val Ser Ser Ala Ser Ser Ala Asp Ile Val Met Thr Gln
            115                 120                 125

Ala Ala Phe Ser Asn Pro Val Thr Leu Gly Thr Ser Ala Ser Ile Ser
        130                 135                 140

Cys Arg Ser Ser Lys Ser Leu Leu His Ser Asn Gly Ile Thr Tyr Phe
145                 150                 155                 160

Phe Trp Tyr Leu Gln Lys Pro Gly Leu Ser Pro Gln Leu Leu Ile Tyr
                165                 170                 175

Gln Met Ser Asn Leu Ala Ser Gly Val Pro Asp Arg Phe Ser Ser Ser
            180                 185                 190

Gly Ser Gly Thr Asp Phe Thr Leu Arg Ile Ser Arg Val Glu Ala Glu
        195                 200                 205

Asp Val Gly Val Tyr Tyr Cys Ala Gln Asn Leu Glu Leu Pro Pro Thr
    210                 215                 220

Phe Gly Gly Gly Thr Lys Leu Glu Ile Lys Arg Ala Ala Ala His His
225                 230                 235                 240

His His His His Gly Ala Ala Glu Gln Lys Leu Ile Ser Glu Glu Asp
                245                 250                 255

Leu Asn Gly Ala Ala
            260

<210> SEQ ID NO 54
<211> LENGTH: 260
<212> TYPE: PRT
<213> ORGANISM: Artificial Sequence
<220> FEATURE:
<223> OTHER INFORMATION: Single chain Fv format sequence

<400> SEQUENCE: 54

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
                100                 105                 110

Leu Thr Val Ser Ser Ala Ser Ser Ala Asp Ile Val Met Thr Gln Ala
            115                 120                 125

Ala Phe Ser Asn Pro Val Thr Leu Gly Thr Ser Ala Ser Ile Ser Cys
        130                 135                 140

Arg Ser Ser Lys Ser Leu Leu His Ser Asn Gly Ile Thr Tyr Phe Phe
145                 150                 155                 160

Trp Tyr Leu Gln Lys Pro Gly Leu Ser Pro Gln Leu Leu Ile Tyr Gln
                165                 170                 175

Met Ser Asn Leu Ala Ser Gly Val Pro Asp Arg Phe Ser Ser Ser Gly

```
                180                 185                 190
Ser Gly Thr Asp Phe Thr Leu Arg Ile Ser Arg Val Glu Ala Glu Asp
                195                 200                 205

Val Gly Val Tyr Tyr Cys Ala Gln Asn Leu Glu Leu Pro Pro Thr Phe
        210                 215                 220

Gly Gly Gly Thr Lys Leu Glu Ile Lys Arg Ala Ala His His His
225                 230                 235                 240

His His His Gly Ala Ala Glu Gln Lys Leu Ile Ser Glu Glu Asp Leu
                245                 250                 255

Asn Gly Ala Ala
        260

<210> SEQ ID NO 55
<211> LENGTH: 259
<212> TYPE: PRT
<213> ORGANISM: Artificial Sequence
<220> FEATURE:
<223> OTHER INFORMATION: Single chain Fv format sequence

<400> SEQUENCE: 55

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Ser Ala Ser Ala Asp Ile Val Met Thr Gln Ala Ala
        115                 120                 125

Phe Ser Asn Pro Val Thr Leu Gly Thr Ser Ala Ser Ile Ser Cys Arg
    130                 135                 140

Ser Ser Lys Ser Leu Leu His Ser Asn Gly Ile Thr Tyr Phe Phe Trp
145                 150                 155                 160

Tyr Leu Gln Lys Pro Gly Leu Ser Pro Gln Leu Leu Ile Tyr Gln Met
                165                 170                 175

Ser Asn Leu Ala Ser Gly Val Pro Asp Arg Phe Ser Ser Ser Gly Ser
            180                 185                 190

Gly Thr Asp Phe Thr Leu Arg Ile Ser Arg Val Glu Ala Glu Asp Val
        195                 200                 205

Gly Val Tyr Tyr Cys Ala Gln Asn Leu Glu Leu Pro Pro Thr Phe Gly
    210                 215                 220

Gly Gly Thr Lys Leu Glu Ile Lys Arg Ala Ala Ala His His His His
225                 230                 235                 240

His His Gly Ala Ala Glu Gln Lys Leu Ile Ser Glu Glu Asp Leu Asn
                245                 250                 255

Gly Ala Ala

<210> SEQ ID NO 56
```

<211> LENGTH: 258
<212> TYPE: PRT
<213> ORGANISM: Artificial Sequence
<220> FEATURE:
<223> OTHER INFORMATION: Single chain Fv format sequence

<400> SEQUENCE: 56

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Ser Ala Ala Asp Ile Val Met Thr Gln Ala Ala Phe
        115                 120                 125

Ser Asn Pro Val Thr Leu Gly Thr Ser Ala Ser Ile Ser Cys Arg Ser
    130                 135                 140

Ser Lys Ser Leu Leu His Ser Asn Gly Ile Thr Tyr Phe Phe Trp Tyr
145                 150                 155                 160

Leu Gln Lys Pro Gly Leu Ser Pro Gln Leu Leu Ile Tyr Gln Met Ser
                165                 170                 175

Asn Leu Ala Ser Gly Val Pro Asp Arg Phe Ser Ser Gly Ser Gly
            180                 185                 190

Thr Asp Phe Thr Leu Arg Ile Ser Arg Val Glu Ala Glu Asp Val Gly
        195                 200                 205

Val Tyr Tyr Cys Ala Gln Asn Leu Glu Leu Pro Pro Thr Phe Gly Gly
    210                 215                 220

Gly Thr Lys Leu Glu Ile Lys Arg Ala Ala Ala His His His His
225                 230                 235                 240

His Gly Ala Ala Glu Gln Lys Leu Ile Ser Glu Glu Asp Leu Asn Gly
                245                 250                 255

Ala Ala

<210> SEQ ID NO 57
<211> LENGTH: 257
<212> TYPE: PRT
<213> ORGANISM: Artificial Sequence
<220> FEATURE:
<223> OTHER INFORMATION: Single chain Fv format sequence

<400> SEQUENCE: 57

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

```
Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
                 85                  90                  95

Tyr Cys Thr Arg His Tyr Tyr Phe Asp Tyr Trp Gly Gln Gly Thr Thr
            100                 105                 110

Leu Thr Val Ser Ser Ala Asp Ile Val Met Thr Gln Ala Ala Phe Ser
        115                 120                 125

Asn Pro Val Thr Leu Gly Thr Ser Ala Ser Ile Ser Cys Arg Ser Ser
    130                 135                 140

Lys Ser Leu Leu His Ser Asn Gly Ile Thr Tyr Phe Phe Trp Tyr Leu
145                 150                 155                 160

Gln Lys Pro Gly Leu Ser Pro Gln Leu Leu Ile Tyr Gln Met Ser Asn
                165                 170                 175

Leu Ala Ser Gly Val Pro Asp Arg Phe Ser Ser Gly Ser Gly Thr
                180                 185                 190

Asp Phe Thr Leu Arg Ile Ser Arg Val Glu Ala Glu Asp Val Gly Val
            195                 200                 205

Tyr Tyr Cys Ala Gln Asn Leu Glu Leu Pro Pro Thr Phe Gly Gly Gly
        210                 215                 220

Thr Lys Leu Glu Ile Lys Arg Ala Ala Ala His His His His His His
225                 230                 235                 240

Gly Ala Ala Glu Gln Lys Leu Ile Ser Glu Glu Asp Leu Asn Gly Ala
                245                 250                 255

Ala

<210> SEQ ID NO 58
<211> LENGTH: 256
<212> TYPE: PRT
<213> ORGANISM: Artificial Sequence
<220> FEATURE:
<223> OTHER INFORMATION: Single chain Fv format sequence

<400> SEQUENCE: 58

Glu Val Lys Leu Val Glu Ser Gly Gly Gly Leu Val Gln Pro Gly Gly
  1               5                  10                  15

Ser Met Lys Leu Ser Cys Val Ala Ser Gly Phe Thr Phe Ser Asn Tyr
                 20                  25                  30

Trp Met Asn Trp Val Arg Gln Ser Pro Glu Lys Gly Leu Glu Trp Val
             35                  40                  45

Ala Glu Ile Arg Leu Lys Ser Asn Asn Tyr Thr Thr His Tyr Ala Glu
 50                  55                  60

Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
                 85                  90                  95

Tyr Cys Thr Arg His Tyr Tyr Phe Asp Tyr Trp Gly Gln Gly Thr Thr
            100                 105                 110

Leu Thr Val Ser Ser Asp Ile Val Met Thr Gln Ala Ala Phe Ser Asn
        115                 120                 125

Pro Val Thr Leu Gly Thr Ser Ala Ser Ile Ser Cys Arg Ser Ser Lys
    130                 135                 140

Ser Leu Leu His Ser Asn Gly Ile Thr Tyr Phe Phe Trp Tyr Leu Gln
145                 150                 155                 160
```

```
Lys Pro Gly Leu Ser Pro Gln Leu Leu Ile Tyr Gln Met Ser Asn Leu
                165                 170                 175

Ala Ser Gly Val Pro Asp Arg Phe Ser Ser Gly Ser Gly Thr Asp
            180                 185                 190

Phe Thr Leu Arg Ile Ser Arg Val Glu Ala Glu Asp Val Gly Val Tyr
            195                 200                 205

Tyr Cys Ala Gln Asn Leu Glu Leu Pro Pro Thr Phe Gly Gly Gly Thr
            210                 215                 220

Lys Leu Glu Ile Lys Arg Ala Ala Ala His His His His His His Gly
225                 230                 235                 240

Ala Ala Glu Gln Lys Leu Ile Ser Glu Glu Asp Leu Asn Gly Ala Ala
                245                 250                 255

<210> SEQ ID NO 59
<211> LENGTH: 255
<212> TYPE: PRT
<213> ORGANISM: Artificial Sequence
<220> FEATURE:
<223> OTHER INFORMATION: Single chain Fv format sequence

<400> SEQUENCE: 59

Glu Val Lys Leu Val Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Thr Thr His Tyr Ala Glu
50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Asp Ile Val Met Thr Gln Ala Ala Phe Ser Asn Pro
            115                 120                 125

Val Thr Leu Gly Thr Ser Ala Ser Ile Ser Cys Arg Ser Ser Lys Ser
130                 135                 140

Leu Leu His Ser Asn Gly Ile Thr Tyr Phe Phe Trp Tyr Leu Gln Lys
145                 150                 155                 160

Pro Gly Leu Ser Pro Gln Leu Leu Ile Tyr Gln Met Ser Asn Leu Ala
                165                 170                 175

Ser Gly Val Pro Asp Arg Phe Ser Ser Gly Ser Gly Thr Asp Phe
            180                 185                 190

Thr Leu Arg Ile Ser Arg Val Glu Ala Glu Asp Val Gly Val Tyr Tyr
            195                 200                 205

Cys Ala Gln Asn Leu Glu Leu Pro Pro Thr Phe Gly Gly Gly Thr Lys
            210                 215                 220

Leu Glu Ile Lys Arg Ala Ala Ala His His His His His His Gly Ala
225                 230                 235                 240

Ala Glu Gln Lys Leu Ile Ser Glu Glu Asp Leu Asn Gly Ala Ala
                245                 250                 255

<210> SEQ ID NO 60
<211> LENGTH: 219
```

```
<212> TYPE: PRT
<213> ORGANISM: Artificial Sequence
<220> FEATURE:
<223> OTHER INFORMATION: Recognition seuqenc of light chain of murine
      IgG1

<400> SEQUENCE: 60

Asp Ile Val Leu Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Asp Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 61
<211> LENGTH: 219
<212> TYPE: PRT
<213> ORGANISM: Artificial Sequence
<220> FEATURE:
<223> OTHER INFORMATION: Recognition seuqenc of light chain of murine
      IgG1

<400> SEQUENCE: 61

Asp Ile Val Met Thr Gln Ala Ala Phe Ser Asn Pro Val Thr Leu Gly
 1               5                  10                  15

Thr Ser Ala Ser Ile Ser Cys Arg Ser Ser Lys Ser Leu Leu His Ser
             20                  25                  30

Asn Gly Ile Thr Tyr Phe Phe Trp Tyr Leu Gln Lys Pro Gly Leu Ser
         35                  40                  45

Pro Gln Leu Leu Ile Tyr Gln Met Ser Asn Leu Ala Ser Gly Val Pro
     50                  55                  60

Asp Arg Phe Ser Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95
```

```
Leu Glu Leu Pro Pro Thr Phe Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 62
<211> LENGTH: 441
<212> TYPE: PRT
<213> ORGANISM: Artificial Sequence
<220> FEATURE:
<223> OTHER INFORMATION: Recognition seuqenc of heavy chain of murine
      IgG1

<400> SEQUENCE: 62

```
Glu Val Lys Leu Val Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
            100                 105                 110

Thr Leu Thr Val Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175

Asp Leu Tyr Thr Leu Ser Ser Ser Val Thr Val Pro Ser Ser Pro Arg
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240
```

-continued

```
Pro Lys Asp Val Leu Thr Ile Thr Leu Thr Pro Lys Val Thr Cys Val
                245                 250                 255

Val Val Asp Ile Ser Lys Asp Pro Glu Val Gln Phe Ser Trp Phe
            260                 265                 270

Val Asp Asp Val Glu Val His Thr Ala Gln Thr Gln Pro Arg Glu Glu
            275                 280                 285

Gln Phe Asn Ser Thr Phe Arg Ser Val Ser Glu Leu Pro Ile Met His
        290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asn Thr Asn Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440

<210> SEQ ID NO 63
<211> LENGTH: 440
<212> TYPE: PRT
<213> ORGANISM: Artificial Sequence
<220> FEATURE:
<223> OTHER INFORMATION: Recognition seuqenc of heavy chain of murine
      IgG1

<400> SEQUENCE: 63

Glu Val Lys Leu Val Glu Ser Gly Gly Gly Leu Val Gln Pro Gly Gly
  1               5                  10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Thr Thr His Tyr Ala Glu
        50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
```

```
                145                 150                 155                 160
            Ser Leu Ser Ser Gly Val His Thr Phe Pro Ala Val Leu Glu Ser Asp
                            165                 170                 175

Leu Tyr Thr Leu Ser Ser Val Thr Val Pro Ser Ser Pro Arg Pro
                        180                 185                 190

Ser Glu Thr Val Thr Cys Asn Val Ala His Pro Ala Ser Ser Thr Lys
                            195                 200                 205

Val Asp Lys Lys Ile Val Pro Arg Asp Cys Gly Cys Lys Pro Cys Ile
                210                 215                 220

Cys Thr Val Pro Glu Val Ser Ser Val Phe Ile Phe Pro Pro Lys Pro
            225                 230                 235                 240

Lys Asp Val Leu Thr Ile Thr Leu Thr Pro Lys Val Thr Cys Val Val
                            245                 250                 255

Val Asp Ile Ser Lys Asp Asp Pro Glu Val Gln Phe Ser Trp Phe Val
                        260                 265                 270

Asp Asp Val Glu Val His Thr Ala Gln Thr Gln Pro Arg Glu Glu Gln
                        275                 280                 285

Phe Asn Ser Thr Phe Arg Ser Val Ser Glu Leu Pro Ile Met His Gln
                        290                 295                 300

Asp Trp Leu Asn Gly Lys Glu Phe Lys Cys Arg Val Asn Ser Ala Ala
            305                 310                 315                 320

Phe Pro Ala Pro Ile Glu Lys Thr Ile Ser Lys Thr Lys Gly Arg Pro
                            325                 330                 335

Lys Ala Pro Gln Val Tyr Thr Ile Pro Pro Lys Glu Gln Met Ala
                        340                 345                 350

Lys Asp Lys Val Ser Leu Thr Cys Met Ile Thr Asp Phe Phe Pro Glu
                        355                 360                 365

Asp Ile Thr Val Glu Trp Gln Trp Asn Gly Gln Pro Ala Glu Asn Tyr
                        370                 375                 380

Lys Asn Thr Gln Pro Ile Met Asn Thr Asn Gly Ser Tyr Phe Val Tyr
            385                 390                 395                 400

Ser Lys Leu Asn Val Gln Lys Ser Asn Trp Glu Ala Gly Asn Thr Phe
                            405                 410                 415

Thr Cys Ser Val Leu His Glu Gly Leu His Asn His Thr Glu Lys
                        420                 425                 430

Ser Leu His Ser Pro Gly Lys
                        435                 440

<210> SEQ ID NO 64
<211> LENGTH: 447
<212> TYPE: PRT
<213> ORGANISM: Artificial Sequence
<220> FEATURE:
<223> OTHER INFORMATION: Sequence for expression of heavy chain of
      chimeric IgG1

<400> SEQUENCE: 64

Glu Val Lys Leu Val Glu Ser Gly Gly Gly Leu Val Gln Pro Gly Gly
  1               5                  10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ser Lys Ala Asn Asn His Ala Thr Tyr Tyr Ala Glu
        50                  55                  60
```

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
            100                 105                 110

Thr Leu Thr Val Ser Gly Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 65
<211> LENGTH: 446
<212> TYPE: PRT
<213> ORGANISM: Artificial Sequence
<220> FEATURE:
<223> OTHER INFORMATION: Sequence for expression of heavy chain of -continued chimeric IgG1

<400> SEQUENCE: 65

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Gly Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 66
<211> LENGTH: 570
<212> TYPE: PRT
<213> ORGANISM: Artificial Sequence
<220> FEATURE:
<223> OTHER INFORMATION: Sequence for expression of heavy chain of
      chimeric IgM

<400> SEQUENCE: 66

Glu Val Lys Leu Val Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Val Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
            100                 105                 110

Thr Leu Thr Val Ser Gly Ser Ala Ser Ala Pro Thr Leu Phe Pro Leu
        115                 120                 125

Val Ser Cys Glu Asn Ser Pro Ser Asp Thr Ser Ser Val Ala Val Gly
    130                 135                 140

Cys Leu Ala Gln Asp Phe Leu Pro Asp Ser Ile Thr Leu Ser Trp Lys
145                 150                 155                 160

Tyr Lys Asn Asn Ser Asp Ile Ser Ser Thr Arg Gly Phe Pro Ser Val
                165                 170                 175

Leu Arg Gly Gly Lys Tyr Ala Ala Thr Ser Gln Val Leu Leu Pro Ser
            180                 185                 190

Lys Asp Val Met Gln Gly Thr Asp Glu His Val Val Cys Lys Val Gln
        195                 200                 205

His Pro Asn Gly Asn Lys Glu Lys Asn Val Pro Leu Pro Val Ile Ala
    210                 215                 220

Glu Leu Pro Pro Lys Val Ser Val Phe Val Pro Pro Arg Asp Gly Phe
225                 230                 235                 240

Phe Gly Asn Pro Arg Lys Ser Lys Leu Ile Cys Gln Ala Thr Gly Phe
                245                 250                 255

Ser Pro Arg Gln Ile Gln Val Ser Trp Leu Arg Glu Gly Lys Gln Val
            260                 265                 270

Gly Ser Gly Val Thr Thr Asp Gln Val Gln Ala Glu Ala Lys Glu Ser
        275                 280                 285

Gly Pro Thr Thr Tyr Lys Val Thr Ser Thr Leu Thr Ile Lys Glu Ser
    290                 295                 300

Asp Trp Leu Gly Gln Ser Met Phe Thr Cys Arg Val Asp His Arg Gly
305                 310                 315                 320

```
Leu Thr Phe Gln Gln Asn Ala Ser Ser Met Cys Val Pro Asp Gln Asp
                325                 330                 335

Thr Ala Ile Arg Val Phe Ala Ile Pro Pro Ser Phe Ala Ser Ile Phe
            340                 345                 350

Leu Thr Lys Ser Thr Lys Leu Thr Cys Leu Val Thr Asp Leu Thr Thr
        355                 360                 365

Tyr Asp Ser Val Thr Ile Ser Trp Thr Arg Gln Asn Gly Glu Ala Val
    370                 375                 380

Lys Thr His Thr Asn Ile Ser Glu Ser His Pro Asn Ala Thr Phe Ser
385                 390                 395                 400

Ala Val Gly Glu Ala Ser Ile Cys Glu Asp Asp Trp Asn Ser Gly Glu
                405                 410                 415

Arg Phe Thr Cys Thr Val Thr His Thr Asp Leu Pro Ser Pro Leu Lys
            420                 425                 430

Gln Thr Ile Ser Arg Pro Lys Gly Val Ala Leu His Arg Pro Asp Val
        435                 440                 445

Tyr Leu Leu Pro Pro Ala Arg Glu Gln Leu Asn Leu Arg Glu Ser Ala
    450                 455                 460

Thr Ile Thr Cys Leu Val Thr Gly Phe Ser Pro Ala Asp Val Phe Val
465                 470                 475                 480

Gln Trp Met Gln Arg Gly Gln Pro Leu Ser Pro Glu Lys Tyr Val Thr
                485                 490                 495

Ser Ala Pro Met Pro Glu Pro Gln Ala Pro Gly Arg Tyr Phe Ala His
            500                 505                 510

Ser Ile Leu Thr Val Ser Glu Glu Glu Trp Asn Thr Gly Glu Thr Tyr
        515                 520                 525

Thr Cys Val Val Ala His Glu Ala Leu Pro Asn Arg Val Thr Glu Arg
    530                 535                 540

Thr Val Asp Lys Ser Thr Gly Lys Pro Thr Leu Tyr Asn Val Ser Leu
545                 550                 555                 560

Val Met Ser Asp Thr Ala Gly Thr Cys Tyr
                565                 570

<210> SEQ ID NO 67
<211> LENGTH: 569
<212> TYPE: PRT
<213> ORGANISM: Artificial Sequence
<220> FEATURE:
<223> OTHER INFORMATION: Sequence for expression of heavy chain of
      chimeric IgM

<400> SEQUENCE: 67

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
```

```
                100                 105                 110
Leu Thr Val Ser Gly Ser Ala Ser Ala Pro Thr Leu Phe Pro Leu Val
            115                 120                 125

Ser Cys Glu Asn Ser Pro Ser Asp Thr Ser Ser Val Ala Val Gly Cys
            130                 135             140

Leu Ala Gln Asp Phe Leu Pro Asp Ser Ile Thr Leu Ser Trp Lys Tyr
145                 150                 155                 160

Lys Asn Asn Ser Asp Ile Ser Ser Thr Arg Gly Phe Pro Ser Val Leu
            165                 170                 175

Arg Gly Gly Lys Tyr Ala Ala Thr Ser Gln Val Leu Leu Pro Ser Lys
            180                 185                 190

Asp Val Met Gln Gly Thr Asp Glu His Val Val Cys Lys Val Gln His
            195                 200                 205

Pro Asn Gly Asn Lys Glu Lys Asn Val Pro Leu Pro Val Ile Ala Glu
            210                 215                 220

Leu Pro Pro Lys Val Ser Val Phe Val Pro Pro Arg Asp Gly Phe Phe
225                 230                 235                 240

Gly Asn Pro Arg Lys Ser Lys Leu Ile Cys Gln Ala Thr Gly Phe Ser
            245                 250                 255

Pro Arg Gln Ile Gln Val Ser Trp Leu Arg Glu Gly Lys Gln Val Gly
            260                 265                 270

Ser Gly Val Thr Thr Asp Gln Val Gln Ala Glu Ala Lys Glu Ser Gly
            275                 280                 285

Pro Thr Thr Tyr Lys Val Thr Ser Thr Leu Thr Ile Lys Glu Ser Asp
            290                 295                 300

Trp Leu Gly Gln Ser Met Phe Thr Cys Arg Val Asp His Arg Gly Leu
305                 310                 315                 320

Thr Phe Gln Gln Asn Ala Ser Ser Met Cys Val Pro Asp Gln Asp Thr
            325                 330                 335

Ala Ile Arg Val Phe Ala Ile Pro Pro Ser Phe Ala Ser Ile Phe Leu
            340                 345                 350

Thr Lys Ser Thr Lys Leu Thr Cys Leu Val Thr Asp Leu Thr Thr Tyr
            355                 360                 365

Asp Ser Val Thr Ile Ser Trp Thr Arg Gln Asn Gly Glu Ala Val Lys
            370                 375                 380

Thr His Thr Asn Ile Ser Glu Ser His Pro Asn Ala Thr Phe Ser Ala
385                 390                 395                 400

Val Gly Glu Ala Ser Ile Cys Glu Asp Asp Trp Asn Ser Gly Glu Arg
            405                 410                 415

Phe Thr Cys Thr Val Thr His Thr Asp Leu Pro Ser Pro Leu Lys Gln
            420                 425                 430

Thr Ile Ser Arg Pro Lys Gly Val Ala Leu His Arg Pro Asp Val Tyr
            435                 440                 445

Leu Leu Pro Pro Ala Arg Glu Gln Leu Asn Leu Arg Glu Ser Ala Thr
450                 455                 460

Ile Thr Cys Leu Val Thr Gly Phe Ser Pro Ala Asp Val Phe Val Gln
465                 470                 475                 480

Trp Met Gln Arg Gly Gln Pro Leu Ser Pro Glu Lys Tyr Val Thr Ser
            485                 490                 495

Ala Pro Met Pro Glu Pro Gln Ala Pro Gly Arg Tyr Phe Ala His Ser
            500                 505                 510

Ile Leu Thr Val Ser Glu Glu Glu Trp Asn Thr Gly Glu Thr Tyr Thr
            515                 520                 525
```

Cys Val Val Ala His Glu Ala Leu Pro Asn Arg Val Thr Glu Arg Thr
        530                 535                 540

Val Asp Lys Ser Thr Gly Lys Pro Thr Leu Tyr Asn Val Ser Leu Val
545                 550                 555                 560

Met Ser Asp Thr Ala Gly Thr Cys Tyr
                565

<210> SEQ ID NO 68
<211> LENGTH: 219
<212> TYPE: PRT
<213> ORGANISM: Artificial Sequence
<220> FEATURE:
<223> OTHER INFORMATION: Sequence for expression of light chain of
      chimeric of IgG1 or IgM

<400> SEQUENCE: 68

Asp Ile Val Leu Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Asp Gly Thr Lys Leu Glu Leu Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 69
<211> LENGTH: 219
<212> TYPE: PRT
<213> ORGANISM: Artificial Sequence
<220> FEATURE:
<223> OTHER INFORMATION: Sequence for expression of light chain of
      chimeric of IgG1 or IgM

<400> SEQUENCE: 69

Asp Ile Val Met Thr Gln Ala Ala Phe Ser Asn Pro Val Thr Leu Gly
  1               5                  10                  15

Thr Ser Ala Ser Ile Ser Cys Arg Ser Ser Lys Ser Leu Leu His Ser
             20                  25                  30

```
Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 70
<211> LENGTH: 30
<212> TYPE: PRT
<213> ORGANISM: Artificial Sequence
<220> FEATURE:
<223> OTHER INFORMATION: Synthetic peptide used as antigen

<400> SEQUENCE: 70

Ala Pro Pro Ala His Gly Val Thr Ser Ala Pro Asp Thr Arg Pro Ala
1               5                   10                  15

Pro Gly Ser Thr Ala Pro Pro Ala His Gly Val Thr Ser Ala
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: Synthetic peptide used as antigen
<220> FEATURE:
<221> NAME/KEY: MOD_RES
<222> LOCATION: (13)...(13)
<223> OTHER INFORMATION: Glycosylated

<400> SEQUENCE: 71

Ala Pro Pro Ala His Gly Val Thr Ser Ala Pro Asp Thr Arg Pro Ala
1               5                   10                  15

Pro Gly Ser Thr Ala Pro Pro Ala His Gly Val Thr Ser Ala
            20                  25                  30

<210> SEQ ID NO 72
<211> LENGTH: 20
<212> TYPE: PRT
<213> ORGANISM: Artificial Sequence
<220> FEATURE:
```

<223> OTHER INFORMATION: Synthetic peptide used as antigen

<400> SEQUENCE: 72

Val Thr Ser Ala Pro Asp Thr Arg Pro Ala Pro Gly Ser Thr Ala Pro
1               5                   10                  15

Pro Ala His Gly
            20

<210> SEQ ID NO 73
<211> LENGTH: 60
<212> TYPE: PRT
<213> ORGANISM: Artificial Sequence
<220> FEATURE:
<223> OTHER INFORMATION: Synthetic peptide used as antigen

<400> SEQUENCE: 73

Val Thr Ser Ala Pro Asp Thr Arg Pro Ala Pro Gly Ser Thr Ala Pro
1               5                   10                  15

Pro Ala His Gly Val Thr Ser Ala Pro Asp Thr Arg Pro Ala Pro Gly
            20                  25                  30

Ser Thr Ala Pro Pro Ala His Gly Val Thr Ser Ala Pro Asp Thr Arg
        35                  40                  45

Pro Ala Pro Gly Ser Thr Ala Pro Pro Ala His Gly
    50                  55                  60

<210> SEQ ID NO 74
<211> LENGTH: 100
<212> TYPE: PRT
<213> ORGANISM: Artificial Sequence
<220> FEATURE:
<223> OTHER INFORMATION: Synthetic peptide used as antigen

<400> SEQUENCE: 74

Val Thr Ser Ala Pro Asp Thr Arg Pro Ala Pro Gly Ser Thr Ala Pro
1               5                   10                  15

Pro Ala His Gly Val Thr Ser Ala Pro Asp Thr Arg Pro Ala Pro Gly
            20                  25                  30

Ser Thr Ala Pro Pro Ala His Gly Val Thr Ser Ala Pro Asp Thr Arg
        35                  40                  45

Pro Ala Pro Gly Ser Thr Ala Pro Pro Ala His Gly Val Thr Ser Ala
    50                  55                  60

Pro Asp Thr Arg Pro Ala Pro Gly Ser Thr Ala Pro Pro Ala His Gly
65                  70                  75                  80

Val Thr Ser Ala Pro Asp Thr Arg Pro Ala Pro Gly Ser Thr Ala Pro
                85                  90                  95

Pro Ala His Gly
            100

<210> SEQ ID NO 75
<211> LENGTH: 21
<212> TYPE: PRT
<213> ORGANISM: Artificial Sequence
<220> FEATURE:
<223> OTHER INFORMATION: Synthetic peptide used as antigen
<220> FEATURE:
<221> NAME/KEY: MOD_RES
<222> LOCATION: (10)...(10)
<223> OTHER INFORMATION: Glycosylated

<400> SEQUENCE: 75

Ala His Gly Val Thr Ser Ala Pro Asp Thr Arg Pro Ala Pro Gly Ser
1               5                   10                  15

Thr Ala Pro Pro Ala
            20

<210> SEQ ID NO 76
<211> LENGTH: 61
<212> TYPE: PRT
<213> ORGANISM: Artificial Sequence
<220> FEATURE:
<223> OTHER INFORMATION: Synthetic peptide used as antigen
<220> FEATURE:
<221> NAME/KEY: MOD_RES
<222> LOCATION: 10, 30, 50
<223> OTHER INFORMATION: Glycosylated

<400> SEQUENCE: 76

Ala His Gly Val Thr Ser Ala Pro Asp Thr Arg Pro Ala Pro Gly Ser
1               5                   10                  15

Thr Ala Pro Pro Ala His Gly Val Thr Ser Ala Pro Asp Thr Arg Pro
            20                  25                  30

Ala Pro Gly Ser Thr Ala Pro Pro Ala His Gly Val Thr Ser Ala Pro
        35                  40                  45

Asp Thr Arg Pro Ala Pro Gly Ser Thr Ala Pro Pro Ala
    50                  55                  60

<210> SEQ ID NO 77
<211> LENGTH: 101
<212> TYPE: PRT
<213> ORGANISM: Artificial Sequence
<220> FEATURE:
<223> OTHER INFORMATION: Synthetic peptide used as antigen
<220> FEATURE:
<221> NAME/KEY: MOD_RES
<222> LOCATION: 10,30,50,70,90
<223> OTHER INFORMATION: Glycosylated

<400> SEQUENCE: 77

Ala His Gly Val Thr Ser Ala Pro Asp Thr Arg Pro Ala Pro Gly Ser
1               5                   10                  15

Thr Ala Pro Pro Ala His Gly Val Thr Ser Ala Pro Asp Thr Arg Pro
            20                  25                  30

Ala Pro Gly Ser Thr Ala Pro Pro Ala His Gly Val Thr Ser Ala Pro
        35                  40                  45

Asp Thr Arg Pro Ala Pro Gly Ser Thr Ala Pro Pro Ala His Gly Val
    50                  55                  60

Thr Ser Ala Pro Asp Thr Arg Pro Ala Pro Gly Ser Thr Ala Pro Pro
65                  70                  75                  80

Ala His Gly Val Thr Ser Ala Pro Asp Thr Arg Pro Ala Pro Gly Ser
                85                  90                  95

Thr Ala Pro Pro Ala
            100

<210> SEQ ID NO 78
<211> LENGTH: 29
<212> TYPE: PRT
<213> ORGANISM: Artificial Sequence
<220> FEATURE:
<223> OTHER INFORMATION: Synthetic peptide used as antigen

<400> SEQUENCE: 78

Ala Pro Pro Ala His Gly Val Thr Ser Ala Pro Asp Thr Arg Pro Ala
1               5                   10                  15

Pro Gly Ser Thr Ala Pro Pro Ala His Gly Val Thr Ser

```
                   20                 25
```

<210> SEQ ID NO 79
<211> LENGTH: 27
<212> TYPE: DNA
<213> ORGANISM: Artificial Sequence
<220> FEATURE:
<223> OTHER INFORMATION: forward primer

<400> SEQUENCE: 79
aattggatcc gagcccagac actggac                                          27

<210> SEQ ID NO 80
<211> LENGTH: 27
<212> TYPE: DNA
<213> ORGANISM: Artificial Sequence
<220> FEATURE:
<223> OTHER INFORMATION: reverse primer

<400> SEQUENCE: 80
accgtctaga cgcactcatt tacccgg                                          27

<210> SEQ ID NO 81
<211> LENGTH: 28
<212> TYPE: DNA
<213> ORGANISM: Artificial Sequence
<220> FEATURE:
<223> OTHER INFORMATION: forward primer

<400> SEQUENCE: 81
atcgggatcc gatagccatg acagtctg                                         28

<210> SEQ ID NO 82
<211> LENGTH: 26
<212> TYPE: DNA
<213> ORGANISM: Artificial Sequence
<220> FEATURE:
<223> OTHER INFORMATION: reverse primer

<400> SEQUENCE: 82
agcgtctaga cagggtcagt agcagg                                           26

<210> SEQ ID NO 83
<211> LENGTH: 30
<212> TYPE: DNA
<213> ORGANISM: Artificial Sequence
<220> FEATURE:
<223> OTHER INFORMATION: forward primer

<400> SEQUENCE: 83
acctggatcc gctaggaaga aactcaaaac                                       30

<210> SEQ ID NO 84
<211> LENGTH: 30
<212> TYPE: DNA
<213> ORGANISM: Artificial Sequence
<220> FEATURE:
<223> OTHER INFORMATION: reverse primer

<400> SEQUENCE: 84
accgtctaga ccctctaaca ctctcccctg                                       30